US012742180B2

(12) United States Patent
Han et al.

(10) Patent No.: US 12,742,180 B2
(45) Date of Patent: Sep. 22, 2026

(54) METHOD FOR PRODUCING GENETICALLY EDITED BIRDS HAVING RESISTANCE TO AVIAN INFLUENZA VIRUSES

(71) Applicant: SEOUL NATIONAL UNIVERSITY R&DB FOUNDATION, Seoul (KR)

(72) Inventors: Jae Yong Han, Seoul (KR); Young Hyun Park, Seoul (KR); Jeong Yong Suh, Seoul (KR); Jeong Mook Lim, Gyeonggi-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 1033 days.

(21) Appl. No.: 17/776,141

(22) PCT Filed: Jan. 7, 2021

(86) PCT No.: PCT/KR2021/000216
§ 371 (c)(1),
(2) Date: May 11, 2022

(87) PCT Pub. No.: WO2021/141421
PCT Pub. Date: Jul. 15, 2021

(65) Prior Publication Data
US 2022/0380797 A1 Dec. 1, 2022

(30) Foreign Application Priority Data
Jan. 7, 2020 (KR) ........................ 10-2020-0002154

(51) Int. Cl.
*C12N 15/85* (2006.01)
*A01K 67/0275* (2024.01)
*C12N 9/22* (2006.01)
*C12N 15/11* (2006.01)

(52) U.S. Cl.
CPC ...... *C12N 15/8509* (2013.01); *A01K 67/0275* (2013.01); *C12N 9/22* (2013.01); *C12N 15/11* (2013.01); *A01K 2227/30* (2013.01); *A01K 2267/02* (2013.01); *C12N 2310/20* (2017.05); *C12N 2800/80* (2013.01)

(58) Field of Classification Search
CPC ...... C12N 15/8509; C12N 9/22; C12N 15/11; A01K 67/0275
See application file for complete search history.

(56) References Cited

U.S. PATENT DOCUMENTS 11,597,948 B2 * 3/2023 Wang ...................... A61P 31/16
2002/0138864 A1 9/2002 Han et al.

FOREIGN PATENT DOCUMENTS

KR 10-0267633 B1 10/2000
KR 10-0305715 B1 11/2001
KR 10-2019-0093171 A 8/2019

OTHER PUBLICATIONS

Long et al. (Nature. Jan. 7, 2016;529(7584): 101-4. doi: 10.1038/nature16474., see IDS) (Year: 2016).*
Han et al. (J Anim Sci Biotechnol. Jan. 31, 2018:9:19. doi: 10.1186/s40104-018-0234-4. eCollection 2018.) (Year: 2018).*
Park et al. (J Infect Dis. Jan. 1, 2020;221(1):71-80. doi: 10.1093/infdis/jiz506.) (Year: 2020).*
Long et al. (Nature. Jan. 7, 2016;529(7584):101-4., see IDS) (Year: 2016).*
Park et al. (J Infect Dis. Oct. 19, 2019; 221(1):71-80., see IDS) (Year: 2019).*
Han et al. (J Anim Sci Biotechnol. Jan. 31, 2018 :9: 19. eCollection 2018., see IDS) (Year: 2018).*
Soh et al., Elife. Apr. 30, 2019:8:e45079. doi: 10.7554/eLife.45079. (Year: 2019).*
International Search Report from corresponding PCT Application No. PCT/KR2021/000216, dated Apr. 16, 2021.
Long, Jason S et al. Species specific differences in use of ANP32 proteins by influenza A vims. eLIFE. 2019, vol. 8, e45066, pp. 1-22.
Park, Young Hyun et al. Host-specific restriction of avian influenza vims caused by differential dynamics of ANP32 family members. The Journal offufectious Diseases. Jan. 1, 2020, vol. 221, No. I.
Domingues, Patricia et al. Profiling host ANP32A splicing landscapes to predict influenza A vims polymerase adaptation. Nature Communications. 2019, vol. 10, article No. 3396, pp. 1-12.
Zhang, Haili et al. Fundamental contribution and host range determination of ANP32A and ANP32B in influenza A vims polymerase activity. Journal of Virology. 2019, vol. 93, No. 13, e00174-19, pp. 1-17.

(Continued)

*Primary Examiner* — Fereydoun G Sajjadi
*Assistant Examiner* — Joel D Levin
(74) *Attorney, Agent, or Firm* — Harness, Dickey & Pierce, P.L.C.

(57) ABSTRACT

Provided is a method of producing a genome-edited bird having resistance to avian influenza viruses. A method according to an aspect may enable precise inhibition of interaction between virus proteins while maintaining the original function of an ANP32A gene in a host by substituting only key amino acids of the ANP32A gene. When the method is used, by including cell lines having resistance to avian influenza viruses, new poultry and bird breeds that may not pose any biological safety issues may be efficiently developed. Thus, it is expected that the potential for industrial application is high.

16 Claims, 21 Drawing Sheets

Specification includes a Sequence Listing.

(56) References Cited

OTHER PUBLICATIONS

Te Velthuis, A. J. W., et al.; "Influenza virus RNA polymerase: insights into the mechanisms of viral RNA synthesis", Nat Rev Microbiol. Aug. 2016 ; 14(8): 479-493.
Hutchinson, E. C., et al.; "Transport of the Influenza Virus Genome from Nucleus to Nucleus" Viruses 2013, 5, 2424-2446.
Jackson, D. A., et al.; "Influenza virus RNA is synthesized at fixed sites in the nucleus", Nature, vol. 296, Mar. 25, 1982, pp. 366-368.
Takizawa, N., et al.; "Association of functional influenza viral proteins and RNAs with nuclear chromatin and sub-chromatin structure", Microbes and Infection 8 (2006) 823e833.
Sugiyama, K., et al.; "pp32 and APRIL are host cell-derived regulators of influenza virus RNA synthesis from cRNA", eLife 2015; 4: pp. 1-19.
Staller, E., et al.; "ANP32 proteins are essential for influenza virus replication in human cells", Journal of Virology, 2019, pp. 1-34.
Long, U.S., et al.; "Species difference in ANP32A underlies influenza A virus polymerase host restriction", Nature, vol. 529, Jan. 7, 2016, pp. 101-116.
Domingues, P., et al.; "Functional Insights into ANP32A-Dependent Influenza A Virus Polymerase Host Restriction", 2017, Cell Reports 20, 2538-2546.
Baker, S. F., et al.; "Differential Splicing of ANP32A in Birds Alters Its Ability to Stimulate RNA Synthesis by Restricted Influenza Polymerase", Cell Rep. Sep. 4, 2018; 24(10): 2581-2588.
Long, J. S., et al.; "Species specific differences in use of ANP32 proteins by influenza A virus", eLife 2019;8, pp. 1-22.
Domingues, P., et al.; "Profiling host ANP32A splicing landscapes to predict influenza A virus polymerase adaptation", Nature Communications, 2019, 10; 3396; pp. 1-12.
Atkinson, G. F., et al.; "The Spear.man-Karber Method of Estimating 50% Endpoints", 1952, pp. 1-5.
Han, J. Y., et al.; "Primordial germ cell-mediated transgenesis and genome editing in birds", Journal of Animal Science and Biotechnology (2018) 9:19.
Krammer, F., et al.; "Advances in the development of influenza virus vaccines", Nature Reviews, Drug Discovery, vol. 14, Mar. 2015, pp. 167-182.
Lee, H. J., et al.; "Precise gene editing of chicken Na+/H+ exchange type 1 (chNHE1) confers resistance to avian leukosis virus subgroup J (Alv-J)", *Developmental and Comparative Immunology* (2017), p. 1-38.
Long, J. S., et al.; "Host and viral determinants of influenza A virus species specificity", Nature Reviews, Microbiology, vol. 17, Feb. 2019, pp. 67-80.
Matilla, A., et al.; "The Anp32 family of proteins containing leucine-rich repeats", The Cerebellum. 2005; 4: 7-18.
Park, Y. H., et al.; "Host-specific restriction of avian influenza virus caused by differential dynamics of ANP32 family members", 2019, pp. 1-17.
Reilly, P T., et al.; "Cracking the ANP32 whips: Important functions, unequal requirement, and hints at disease implications", Bioessays 36: 1062-1071, 2014.
Shinya, K., et al.; "Ostrich Involvement in the Selection of H5N1 Influenza Virus Possessing Mammalian-Type Amino Acids in the PB2 Protein", Journal of Virology, Dec. 2009, p. 13015-13018.
Sid, H., et al.; "Applications of Gene Editing in Chickens: A New Era Is on the Horizon", Front. Genet. 9:456, pp. 1-12.
Watanabe, T., et al.; "Influenza virus-host interactome screen as a platform for antiviral drug development", Cell Host Microbe. Dec. 10, 2014; 16(6): 795-805.
Wei, X., et al.; "The interaction of cellular protein ANP32A with influenza A virus polymerase component PB2 promotes vRNA synthesis", Archives of Virology, 2018, pp. 1-12.
Zhang, H., et al.; "Fundamental Contribution and Host Range Determination of ANP32A and ANP32B in Influenza A Virus Polymerase Activity", Journal of Virology, vol. 93, Issue 13, Jul. 2019, pp. 1-17.
Zhang, J-P., et al.; "Efficient precise knockin with a double cut HDR donor after CRISPR/Cas9-mediated double-stranded DNA cleavage", Genome Biology (2017) 18:35, pp. 1-18.
Park, Y. H., et al.; "Asp149 and Asp152 in chicken and human ANP32A play an essential role in the interaction with influenza viral polymerase", The FASEB Journal. 2021;35, pp. 1-11.

* cited by examiner

FIG. 1B (in-del, frequency)

*ATG* GACATGAAGA AAAGGATCCACTTAGAGCTG CGGAACAGGACG (wild type, 2x)
*ATG* GACATGAAGA AAAGGATCCACTTAGAG CTG CGGAACAGGACG (4nt del, 1x)
*ATG* GACATGAAGA AAAGGATCCACTTAGAGCTG CGGAACAGGACG (1nt del, 1x)
*ATG* GACATGAAGA AAAGGATCCACTTA GAGCTG CGGAACAGGACG (4nt del, 1x)
*ATG* GACATGAAGA AAAGGATCCACTTAGAGCTGCGGAACAGGA CG (13nt del, 1x)
*ATG* GACATGAAGA AAAGGATCCACTTAGAGTGCCTG CGGAACAGG (3nt ins, 1x)
*ATG* GACATGAAGA AAAGGATCCACTTAGAGCT G CGGAACAGGACG (3nt del, 1x)
*ATG* GACATGAAGA AAAGGATCCACTTAGAGCTG CGGAACAGGACG (4nt del, 1x)
*ATG* GACATGAAGA AAA GGATCCACTTAGAG CTG CGGAACAGGACG (14nt del, 1x)
*ATG* GACATGAAGA AAAGGATCCACTTAGAGCTG CGGAACAGGACG (2nt del, 1x)

| | 149 | | | | | | | | | | | | 161 |
|---|---|---|---|---|---|---|---|---|---|---|---|---|---|
| WT | D | R | D | D | K | E | A | P | D | S | D | A | E |
| D149Y | Y | R | D | D | K | E | A | P | D | S | D | A | E |
| R150W | D | W | D | D | K | E | A | P | D | S | D | A | E |
| D152H | D | R | D | H | K | E | A | P | D | S | D | A | E |
| D157Y | D | R | D | D | K | E | A | P | Y | S | D | A | E |
| A160I | D | R | D | D | K | E | A | P | D | S | D | I | E |

Non-polar
Polar, basic
Polar, acidic
Polar, uncharged

FIG. 5C (in-del, frequency)

CTCCTC CCACAACTCACATACCTCGATGG CTACGATCGGGATGACAAAG (wildtype, 2x)
CTCCTC CCACAACTCACATACCTCGATGG CTACGATCGGGATGACAAAG (6nt del, 2x)
CTCCTC CCACAACTCACATACCTCGATGG CTACGATCGGGATGACAAAG (2nt del, 2x)
CTCCTC CCACAACTCACATACCTCGATGG CTACGATCGGGATGACAAAG (2nt del, 2x)
CTCCTC CCACAACTCACATACCTCGATGG CTACGATCGGGATGACAAAG (15nt del, 1x)
CTCCTCCCACAACTCACATACCTCGATGG CTACGATCGGGATGACAAAG (26nt del, 1x)
CTCCTC CCACAACTCACATACCTCGATGGCTACGATCGGGATGACAAAG (30nt del, 1x)
CTCCTC CCACAACTCACATACCTTCGATGG CTACGATCGGGATGACAAAG (1nt ins, 1x)
CTCCTC CCACAACTCACATACCTCTCGATGG CTACGATCGGGATGACAAAG (2nt ins, 1x)

FIG. 7B

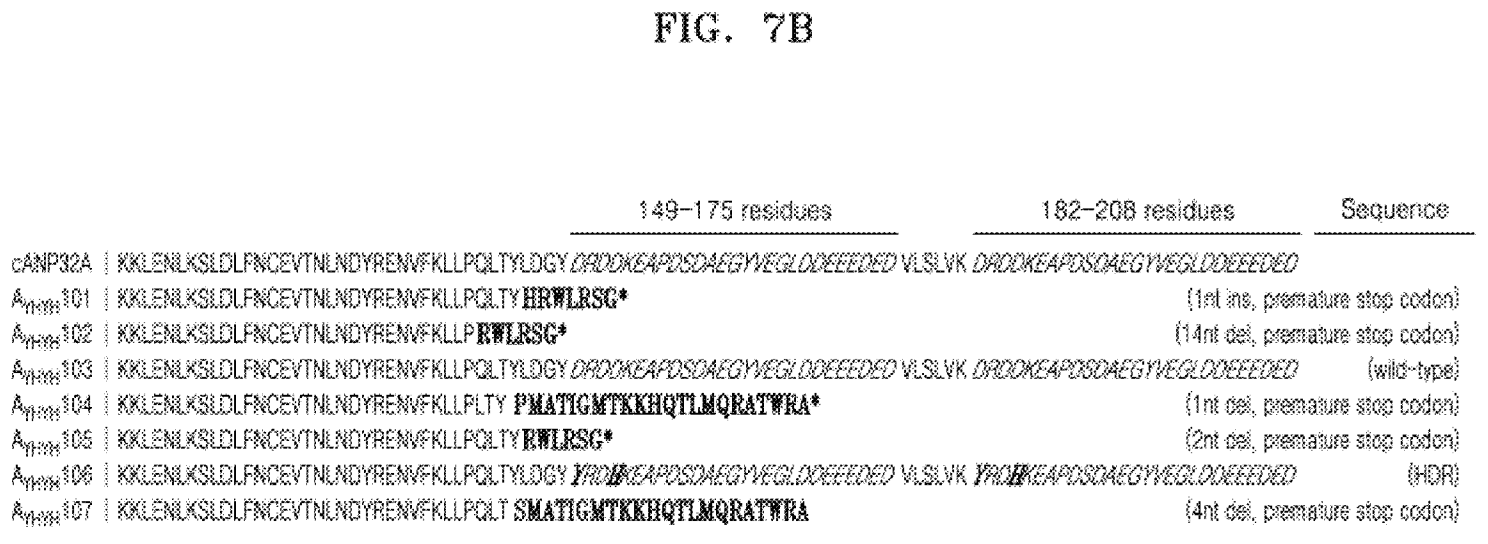

| | 149-175 residues | | 182-208 residues | Sequence |
|---|---|---|---|---|
| cANP32A | KKLENLKSLDLFNCEVTNLNDYRENVFKLLPQLTYLDGY *DRDDKEAPDSDAEGYVEGLDDEEEDED* | VLSLVK | *DRDDKEAPDSDAEGYVEGLDDEEEDED* | |
| A[illegible]101 | KKLENLKSLDLFNCEVTNLNDYRENVFKLLPQLTY **HRWLRSG*** | | | (1nt ins, premature stop codon) |
| A[illegible]102 | KKLENLKSLDLFNCEVTNLNDYRENVFKLLP **RWLRSG*** | | | (14nt del, premature stop codon) |
| A[illegible]103 | KKLENLKSLDLFNCEVTNLNDYRENVFKLLPQLTYLDGY *DRDDKEAPDSDAEGYVEGLDDEEEDED* | VLSLVK | *DRDDKEAPDSDAEGYVEGLDDEEEDED* | (wild-type) |
| A[illegible]104 | KKLENLKSLDLFNCEVTNLNDYRENVFKLLPLTY **PMATIGMTKKHQTLMQRATWRA*** | | | (1nt del, premature stop codon) |
| A[illegible]105 | KKLENLKSLDLFNCEVTNLNDYRENVFKLLPQLTY **RWLRSG*** | | | (2nt del, premature stop codon) |
| A[illegible]106 | KKLENLKSLDLFNCEVTNLNDYRENVFKLLPQLTYLDGY *YRDHKEAPDSDAEGYVEGLDDEEEDED* | VLSLVK | *YRDHKEAPDSDAEGYVEGLDDEEEDED* | (HDR) |
| A[illegible]107 | KKLENLKSLDLFNCEVTNLNDYRENVFKLLPQLT **SMATIGMTKKHQTLMQRATWRA** | | | (4nt del, premature stop codon) |

METHOD FOR PRODUCING GENETICALLY EDITED BIRDS HAVING RESISTANCE TO AVIAN INFLUENZA VIRUSES

CROSS-REFERENCE TO RELATED APPLICATIONS

This application is a national phase application of PCT Application No. PCT/KR2021/000216, filed on Jan. 7, 2021, which claims priority to Korean Patent Application No. 10-2020-0002154, filed on Jan. 7, 2020. The entire disclosure of the applications identified in this paragraph is incorporated herein by references.

TECHNICAL FIELD

The present invention relates to a method of producing a genome-edited bird having resistance to avian influenza viruses.

BACKGROUND ART

Avian influenza viruses (AIVs) cause huge economic losses in the poultry industry and are highly likely to cause infection and death in humans. To develop new antiviral drugs, recent studies have focused on targeting host cell factors that are inevitably necessary for virus proliferation (Korean Patent Publication No. 10-2013-0126243). During a virus life cycle, viruses and their viral polymerase (vPol) efficiently replicate and transcribe viral RNA in host cells by selecting cell mechanisms (cell machinery) of host cells including DNA-dependent RNA polymerase, splicing factors, and other RNA treatment factors. After viral infection, a virus ribonucleoprotein is released into the cytoplasm and transported to a nucleus of the host for viral RNA replication. AIV replication from a positive-sense complementary RNA to a negative-sense single-stranded viral RNA occurs in the nucleus of the host by cell DNA-dependent RNA polymerase II, where vPol actively selects cell machinery of the host cell.

The Acidic Nuclear Phosphoprotein 32 Family Member A (ANP32A) gene was reported to be involved in replication of viral RNA of AIV. However, because the ANP32A gene performs a variety of functions within a cell in addition to its role in helping replication of viruses, complete destruction or modification of the ANP32A gene may be likely to cause side effects. Therefore, there is a need for a technique to develop AIV-resistant poultry and animals with few side effects by performing only a small number of corrections to a specific host factor involved in the replication of the virus.

SUMMARY

Technical Problem

The present inventors identified a key amino acid of an ANP32A involved in virus replication, and induced only modification of the key amino acid through genetically precise correction based on CRISPR/Cas9 system to efficiently transform the ANP32A gene. Therefore, it was confirmed that a cell line and an avian model had resistance to avian influenza, thereby completing the present invention.

An aspect may provide a recombinant vector including a guide RNA (gRNA) or a polynucleotide encoding the gRNA, wherein the guide RNA (gRNA) may target at least one residue selected from the group consisting of Asp149, Asp152, Asp182, and Asp185 in ANP32A gene.

Another aspect may provide a genome-editing composition including the recombinant vector and at least one nuclease encoding sequence selected from the group consisting of CRISPR associated protein 9 (Cas9), CRISPR from *Prevotella* and *Francisella* 1 (Cpf1), a transcription activator-like effector nuclease (TALEN), and a zinc finger nuclease (ZFN).

Still another aspect may provide a transformed cell introduced with the recombinant vector or the genome-editing composition and a method of the same.

Still another aspect may provide a method of producing a genome-edited bird including transplanting the transformed cell into an embryo of a bird and a genome-edited bird having resistance to avian influenza viruses produced according to the method.

However, the technical problems to be achieved by the present invention are not limited to the problems above, and other problems not mentioned herein will be clearly understood to one of the ordinary skills in the art from the following descriptions.

Solution to Problem

The term "vector" as used herein is DNA that enables the introduction of a desired DNA fragment into a host bacteria to be proliferated. The vector is also known as a cloning vehicle, and vector DNA is cut by a restriction enzyme to open the ring so that a desired DNA fragment is inserted and connected thereto and introduced into the host bacteria. A vector DNA linked to the desired DNA fragment is replicated as the host bacteria proliferates and is distributed to each daughter cell along with the division of the bacteria, thereby maintaining the desired DNA fragment from generation to generation. A plasmid or a phage chromosome mainly used as a vector DNA.

The term "recombinant vector" as used herein may be used as a vector to efficiently transform a target gene in appropriate host cells by using CRISPR/Cas9 system or the like to induce double strand break in a base sequence at a specific gene site to perform gene-editing. The host cells may preferably be eukaryotic cells, depending on the type of host cells, expression regulatory sequences, such as promoters, terminators, enhancers, or the like, or sequences for membrane targeting or for secretion or the like may be appropriately selected, and various combinations thereof may be prepared according to the purpose.

The term "guide RNA (guide RNA or gRNA)" as used herein refers to an RNA specific to a target DNA. The guide RNA may be, for example, at least one selected from the group consisting of CRISPR RNA (crRNA), trans-activating crRNA (tracrRNA), and single guide RNA (sgRNA). For example, the guide RNA may be a double-stranded RNA including crRNA and tracrRNA as a component or a single-stranded guide RNA (sgRNA) where crRNA or a part thereof is connected with tracrRNA or a part thereof by an oligonucleotide linker. The guide RNA may be any RNA that may show activity of an (RNA-guide) nuclease in a target sequence.

The term "nuclease (or enzyme endonuclease)" as used herein refers to an enzyme that cuts a specific sequence of genes. The nuclease may be, for example, a transcription activator-like effector nuclease (TALEN), a zink finger nuclease (ZFN) or an RNA-guide nuclease.

The term "RNA-guide nuclease" as used herein refers to a nuclease capable of cutting in recognition of a specific position on a target genome, especially having a target specificity by a guide RNA. The RNA-guided nuclease is not limited thereto, but the RNA-guided nuclease may include, specifically, Cas9 protein derived from CRISPR, which is a microbial immune system, specifically, CRISPR Associated Protein 9 (Cas9), and Cpf1

The nuclease may cause double strand break (DSB) by recognizing certain base sequences in the genome of flora and fauna cells, including human cells, and the nuclease may form a nick. The double strand break may include both a blunt end or an adhesive end formed by cutting the double helix of a DNA. The double strand break may be efficiently repaired by homologous recombination or non-homologous end-joining (NHEJ) mechanism in a cell, at which time a desired variation may be introduced into the target site. The nuclease may be an artificial nuclease or a non-naturally occurring nuclease that is manipulated.

The term "CRISPR/Cas9" or "CRISPR/Cas9 system" as used herein refers to a genome-editing method called CRISPR (clustered regularly interspaced short palindromic repeat) gene scissors. The CRISPR/Cas9 system consists of RNA (gRNA) that specifically binds to a particular base sequence and Cas9 proteins serving as a scissors that cuts the particular base sequence. When the CRISPR/Cas9 system is used, it is possible to knock-out particular gene to inhibit its function by introducing a plasmid DNA into cells or animals.

The term "CRISPR associated protein 9 (Cas9) protein" as used herein refers to an essential protein element in the CRISPR/Cas9 system. The Cas9 protein may form an active endonuclease or nickase when forming a complex with two RNAs called CRISPR RNA (crRNA) and trans-activating crRNA (tracrRNA).

The Cas protein or genetic information may be obtained from a known database such as GenBank of National Center for Biology Information (NCBI). In particular, the Cas protein may be Cas9 protein. In addition, the Cas protein is not limited thereto, but may be derived from *Streptococcus* genus, *Neisseria* genus, *Pasteurella* genus, *Francisella* genus, and *Campylobacter* genus.

The term "CRISPR from *Prevotella* and *Francisella* 1 (Cpf1) protein" as used herein refers to a nuclease of a novel CRISPR system distinguished from the CRISP R/Cas system. The Cpf1 protein may be driven by a single RNA, may not require a tracrRNA, and have a characteristic of a relatively small size, as compared with Cas9.

An aspect may provide a recombinant vector including a guide RNA (gRNA) or a polynucleotide encoding the gRNA, wherein the guide RNA (gRNA) may target at least one residue selected from the group consisting of Asp149, Asp152, Asp182, and Asp185 in ANP32A gene.

The ANP32A gene may be a chicken ANP32A gene (cANP32A; NCBI gene ID: 415562) or a human ANP32A gene (hANP32A; NCBI gene ID: 8125). The genes may each consist of a nucleotide sequence of SEQ ID NO: 1 or a nucleotide sequence of SEQ ID NO: 2, but is not limited thereto.

In addition, the ANP32A protein may be a chicken ANP32A protein (NCBI accession No. XP 413932) or a human ANP32A protein (NCBI accession No. NP_006296). The proteins may each consist of an amino acid sequence of SEQ ID NO: 3 or an amino acid sequence of SEQ ID NO: 4, but is not limited thereto.

It is apparent to one of ordinary skill in the art that the sequence of the ANP32A gene herein is only an example and is not limited thereto. Sequences having substantial sequence identity or substantial sequence homogeneity (sequence identity) for sequences may also be included in the scope of the present invention. The term "substantial sequence identity" or "substantial sequence homogeneity" as used herein means that a sequence may exhibit substantial structural or functional identity with another sequence.

The ANP32A gene is involved in transcription activity and replication of avian influenza viruses, as well as cell proliferation and differentiation, caspase dependency or caspase non-dependent cell death, tumor suppressor, modulation of mRNA stability and migration in relation to ELAVL1, E4F1 mediated transcription inhibition, and various functions in a cell.

The guide RNA may be represented by SEQ ID NO: 14, and a polynucleotide encoding the guide RNA may include a protospacer adjacent motif (PAM).

The PAM sequence may be 5'-TGG'-3' or 5'-TTN-3' (wherein N is A, T, C, or G), but is not limited thereto.

In an embodiment, a polynucleotide including a PAM sequence and a guide RNA targeting exons 4 and 5 was produced to induce modification to a specific amino acid residue in a cANP32A gene.

The polynucleotide sequence may be as follows:

```
                                  (SEQ ID NO: 15)
          5'-CCACAACTCACATACCTCGATGG-3'
```

In an embodiment, a double-cut donor-mediated HDR was performed by using a donor plasmid including the polynucleotide for accurate genome-editing.

Another aspect may provide a genome-editing composition including the recombinant vector and at least one nuclease encoding sequence selected from the group consisting of CRISPR associated protein 9 (Cas9), CRISPR from *Prevotella* and *Francisella* 1 (Cpf1), a transcription activator-like effector nuclease (TALEN), and a zinc finger nuclease (ZFN).

The term "genome editing" as used herein, unless otherwise stated, refers to inducing loss, change, and/or recovery (modification) of genetic function by deletion, insertion, or substitution of a nucleic acid (at least one, for example, 1 bp to 100,000 bp, 1 bp to 10,000 bp, 1 by to 1,000 bp, 1 by to 100 bp, 1 by to 70 bp, 1 bp to 50 bp, 1 bp to 30 bp, 1 bp to 20 bp, or 1 bp to 10 bp) of a target gene at a target site by cleavage.

The nuclease encoding sequence may be used in a form contained in a separate recombinant vector distinguished from the donor plasmid.

The genome-editing composition may induce substitution of at least one selected from the group consisting of D149Y, D152H, D182Y, and D185H in an ANP32A gene.

In addition the composition may be for inducing resistance to avian influenza viruses.

In an embodiment, a donor plasmid including a guide RNA targeting exons 4 and 5 of the cANP32A gene and CRISPR/Cas9 vector may be co-transfected in DF-1 cells, and the transfected cells harbor precise substitution from the cANP32A gene to D149Y, D152H, D182Y, and D185H, thereby inducing resistance to avian influenza viruses in chicken host cells.

Still another aspect may provide a transformed cell into which the recombinant vector or the genome-editing composition of claim 4 is introduced.

The term "transformation" as used herein refers to a change in genetic properties due to DNA given from the outside. That is, transformation refers to a change in genetic traits of a cell caused by a DNA, i.e., a type of an extracted nucleic acid, of a cell of a biotype injected into a living cell of another system. The transformation may also be referred to as transgenic. That is, "transformation" refers to expression of a gene into a host cell by injection.

A method of transforming by introducing the recombinant vector according to an aspect into a cell line may be a method known in the art, for example, but is not limited to, transformation by introducing into eukaryotic cells by transient transfection using lipofectamine, microscopy, transduction, cell fusion, calcium phosphate precipitation, liposome-mediated transfection, DEAE dextran-mediated transfection, polybrene-mediated transfection, or electroporation. The method of transforming may be performed by, preferably, using Lipofectamine 2000 reagent.

Screening of transformed cells may be performed by a known method of identifying whether a gene is edited. Preferably, the screening may be performed by using genes resistant to antibiotics such as G418, neomycin, or puromycin, but is not limited thereto.

The transformation may be performed in vitro, ex vivo, or in vivo. The transformed cells may be cultured for about 1 hour to about 2 years, from about 6 hours to about 1 year, from about 1 day to about 200 days, from about 15 days to about 200 days, or from about 1 month to about 1 year in vitro or ex vivo.

In an embodiment, key amino acid residues essential for viral proliferation were found, and it was identified that transformed cells, in which Asp149, Asp152, Asp182, and Asp185 in the ANP32A gene were modified (substituted), had resistance to avian influenza.

The cell may be selected from the group consisting of stem cells, somatic cells, germ cells, fertilized eggs, and embryos, of a bird. Preferably, the cell may be a somatic cell or a germ cell. More preferably, the germ cells may be primordial germ cells (PGCs), but is not limited thereto.

The recombinant vector or the genome-editing composition may be introduced to an avian primordial germ cell by a method known in the art. For example, gene transfer to a primordial germ cell may be carried out with reference to electroporation, liposome-mediated transfer method, and retrovirus-mediated transfer method.

The primordial germ cell as used herein may be obtained from various sources. Most preferably, the primordial germ cell may be separated from an embryonic gonad of a bird. When an embryo is used as a source of a primordial germ cell, the donor embryo used in the present invention may be in various stages. 1 day to 10 days old embryos may be used. Preferably, the donor embryo may be in an embryonic development stage of about 24 to 36 (about 4 days to 8 days old). Most preferably, the donor embryo may be in an embryonic development stage of about 28 (about 5.5 days old). A method of obtaining a primordial germ cell from a primordial gonad may be performed in various manners, disclosed particularly in Korean Pat. Nos. 0305715 and 0267633 filed by the present inventors. For example, primordial gonads are retrieved from embryos of removed yolk and isolated by the treatment of protease (e.g., trypsin) on the primordial gonads. The gonadal cell is a population of several cell species including stroma cells as well as primordial germ cells. The term "gonadal cells" as used herein refers to a population of all cell species existing in primordial gonad. In addition, the term "gonadal primordial germ cells" as used herein refers to one type of gonadal cells to develop germ cells, abbreviated as "gPGCs" or "PGC".

Still another aspect may provide a method of producing a transformed cell including introducing the recombinant vector or the genome-editing composition to an avian somatic cell.

Still another aspect may provide a method of producing a genome-edited bird including transplanting the transformed cell into an embryo of a bird.

For example, a transformed cell of which a gene is edited (for example, a primordial germ cell) may be injected into a recipient embryo. The injection of cultured primordial germ cells into a recipient embryo may be according to a variety of procedures, preferably, by injecting primordial germ cells into the dorsal aorta of the recipient embryo. For example, a cell suspension containing the suitable number of primordial germ cells is injected into the dorsal aorta of a recipient embryo using a micropipette, and the egg containing the embryo is sealed, followed by incubating fora suitable period of time. Then, the egg containing the recipient embryo may be cultured and incubated, and a gene-edited bird may be produced through a test cross for the recipient that has reached sexual maturity. The confirmation of a genome-edited bird may be, for example, performed by identifying whether a sequence is edited by polymerase-chain reaction (PCR), real-time PCR method, or base sequence analysis using genomic DNA as a template obtained from feather pulp or blood of the genome-edited bird.

The method may further include selecting a homozygous gene variant by test-crossing the gene variant produced by the method.

In addition, the method may further include introducing a nucleic acid encoding a fluorescent protein into an avian primordial germ cell for selection of the primordial germ cell in which gene modification has occurred. The fluorescent protein is not particularly limited as long as the fluorescent protein may be expressed in an avian cell, for example, the fluorescent protein may be green fluorescent protein (GFP). Such a protein may be introduced into a vector that may act in a bird and may be introduced together into a PGC. After introduction, cells expressing the fluorescent protein may be selected by a method such as FACS, and only these cells may be introduced into the recipient embryo to increase production efficiency of transformed bird.

The bird may be selected from the group consisting of, but not limited to, chickens, ducks, geese, quails, pheasants, and turkeys. The bird may be, preferably, chicken.

The genome-edited bird may have resistance to avian influenza viruses.

Still another aspect may provide a genome-edited bird having resistance to avian influenza viruses produced according to the method.

Advantageous Effects of Disclosure

A method according to an aspect may enable precise modification of interaction between virus proteins while maintaining the original function of an ANP32A gene in a host by correcting only key amino acids of the ANP32A gene. When the method is used, by including cell lines having resistance to avian influenza viruses, new poultry and bird breeds that may not pose any biological safety issues may be efficiently developed. Thus, it is expected that the potential for industrial application is high.

BRIEF DESCRIPTION OF THE DRAWINGS

FIGS. 1A, 1B and 1C shows results of establishing a chicken ANP32A knockout DF-1 clone through CRISPR/Cas9-mediated genome editing. (1A) shows T7E1 analysis results of DF-1 cells transfected with a CRISPR/Cas9 vector including A #1 guide RNA (gRNA) targeting exon 1 of chicken ANP32A (cANP32A). Wild-type DF-1 cells were used as a control. (1B) shows results of mutational analysis of transfected DF-1 cells by Sanger sequencing. Insertion-deletion (in-del) mutation frequency is indicated in parentheses. Characters with strikethrough (thickest boldface) indicate deleted nucleotides, and characters without strikethrough (thickest boldface) indicate inserted nucleotides. 'AAAGGATCCACTTAGAGCTG' indicates a gRNA-binding site sequence, and 'CGG' indicates a protospacer adjacent motif (PAM) sequence, and ATG codons are indicated in italics at the beginning of the sequences. (1C) shows sequencing results using chromatography of a cANP32A-knockout clone (A112).

FIGS. 5A, 5B and 5C shows results of genome editing by CRISPR/Cas9 of exon 4 of chicken ANP32A. (5A) shows the chicken ANP32A (cANP32A) gene structure and target genetic locus (exon 4) of A #4 guide RNA (gRNA). (5B) shows results of T7E1 analysis of DF-1 cells transfected with A #4 CRISPR/Cas9 vector. Wild-type DF-1 cells were used as a control. (5C) shows results of mutational analysis of transfected DF-1 cells by Sanger sequencing. In-del mutation frequency is indicated in parentheses. Characters with strikethrough (thickest boldface) indicate deleted nucleotides, and characters without strikethrough (thickest boldface) indicate inserted nucleotides. Characters in bold indicate gRNA binding sites, and 'TGG' indicates a protospacer adjacent motif (PAM) sequence.

FIGS. 7A, 7B and 7C show results of confirming acquisition of AIV resistance through precise correction of chicken ANP32A gene in DF-1 cells. (7A) is a schematic view of an HDR-mediated precise correction process of exons 4 and 5 of chicken ANP32A. The donor plasmid includes D149Y, D152H, D182Y, and D185H-modified cANP32A having homology arms (HAs) on both sides. (7B) is a protein sequence of a cANP32A-modified DF-1 clone through cDNA sequencing from exon 4 to exon 5 of cANP32A. (7C) shows virus titers measured after infecting a premature stop codon ($A_{YHYH}$101), a wild-type ($A_{YHYH}$103), and HDR ($A_{YHYH}$106) DF-1 clones with PR8-H5N8 PB2-627E or PB2-627K influenza virus (MOI 0.1). Data are expressed as mean±standard deviation (n=3). *P<0.05, P<0.01, *P<0.001, and ****P<0.0001. ns=non-significant.

DETAILED DESCRIPTION

Figure 1A:
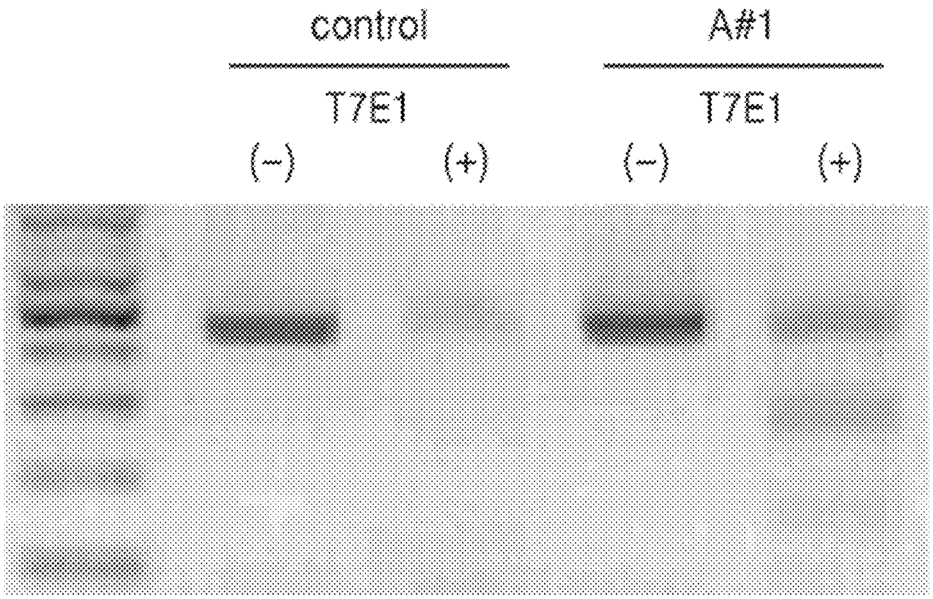

Hereinafter, the present disclosure will be described in more detail with reference to Examples. However, these Examples are for illustrative purposes only, and the present disclosure is not intended to be limited by these Examples.

Experiment Method

Sequence Analysis of ANP32 Family Gene

To find key genes involved in proliferation of avian influenza viruses, human and chicken ANP32 family genes (ANP32A, ANP32B, ANP32C, ANP32D, and ANP32E) were analyzed. In particular, sequence information of cANP32A (XP_413932), cANP32B (NP_001026105), cANP32E (NP_001006564), hANP32A (NP_006296), hANP32B (NP_006392), hANP32C (NP_036535), hANP11232D (NP_036536), and hANP32D (NP_036536) provided from NCBI database was obtained. Then, pairwise sequence alignment and multiple sequence alignment analysis were performed. The protein sequences were aligned by using Geneious R6 software (Biomatters Ltd., Auckland, New Zealand) using Blosum62 scoring matrix, and 12 gap open penalty and 3 gap extension penalty were used.

Production of Recombinant Avian Influenza Viruses

Recombinant avian influenza viruses PR8-H5N8 PB2-627E and -627K were produced using reverse genetics approach from 8 bidirectional PHW2000 plasm ids in the same method as in the previous study (Park et al., J Infect Dis, 2019). Briefly, 8 bidirectional plasmids were co-transfected with co-cultured Madin-Darby canine kidney cells (MDCK; ATCC, CCL-34) and human 293T embryonic kidney cells (HEK293T; ATCC, CRL-11268) to obtain virus. The obtained virus was grown in MDCK infection medium consisting of DMEM supplemented with 0.3% bovine serum albumin (BSA), 1×ABAM, and 1 μg/mL TPCK-treated trypsin (Sigma-Aldrich, MO, USA), and then the obtained virus was cultured for 48 hours at 37° C. The virus stock was further propagated in 10-day-old incubated eggs, and an aliquot of the infectious virus was stored at −80° C. for further experiments.

Virus Titration $TCID_{50}$ was determined by performing virus titration of infected cells in MDCK cells. Briefly, a confluent layer of MDCK cells cultured in serum-free DMEM supplemented with 0.3% BSA, 1% penicillin/streptomycin, and 1 μg/mL TPCK-trypsin in 96-well plates, i.e., a supernatant of the infected cells was used for infection. Serial dilutions of the supernatant were added in triplicate to 5 wells of a 96-well plate. After 72 hours to 96 hours, the cell denaturation effect was observed and quantified through crystal violet (Sigma-Aldrich) staining. The $TCID_{50}$ per mL was calculated using Spearman-Karber formula (Gilles, Eur J Toxicol Environ Hyg, 1974).

RT-qPCR

Total RNA was extracted using RNeasy mini kit (Qiagen), and reverse transcription was performed using Superscript IV First-strand Synthesis System (Thermo Fisher Scientific). RT-qPCR based on EvaGreen qPCR dye (Biotium, CA, USA) was performed three times using the StepOnePlus real-time PCR system (Thermo Fisher Scientific). The target gene-specific forward and reverse primers are shown in Table 1. Relative quantification of target gene expression was calculated using the $2^{-\Delta\Delta ct}$ formula (here, $^{\Delta\Delta Ct}$=(Ct of target gene—Ct of ACTB) group—(Ct of target gene—Ct of ACTB) control.

Co-Immunoprecipitation

Total protein was prepared from cell lysates of transfected cells using immunoprecipitation lysis buffer (Thermo Fisher Scientific). For immunoprecipitation, target antibody-conjugated magnetic beads were prepared using Dynabeads Protein G kit (Thermo Fisher Scientific) according to the manufacturer's instructions. Briefly, non-specific binding proteins were removed in advance by incubating with unbound magnetic beads with gentle rotation at 4° C. for 30 minutes. Then, the previously removed cell lysate was cultured with target antibody-conjugated magnetic beads at 4° C. overnight while gently rotating. Magnetic beads were collected using a magnetic field, and then washed 4 times for unbound protein with a wash buffer. The immunoprecipitated protein was eluted for 5 minutes using an elution buffer and denatured at 95° C. for 5 minutes using 2×Laemmli sample buffer (BioRad). Magnetic beads were collected using a magnetic field, and then the supernatant was used for subsequent experiments.

Western Blotting

The total protein or immunoprecipitated protein was separated by 10% SDS-PAGE. The separated protein was transferred to a PVDF membrane and blocked for 1 hour. The membrane was incubated with an appropriate primary antibody and then incubated with an appropriate HRP-conjugated secondary antibody (Thermo Fisher Scientific). The antibodies used in the experiment are as follows: anti-ACTB (sc-47778, Santa Cruz, TX, USA), anti-ANP32A (sc-100767, Santa Cruz), anti-FLAG (F1804, Sigma-Aldrich), anti-PA (GTX125932, GeneTex, CA, USA), anti-PB1 (GTX125923, GeneTex), anti-PB2 (GTX125926, GeneTex), and anti-NP (GTX125989, GeneTex). Immunoreactive proteins were visualized using ECL select Western blotting detection reagent (GE Healthcare Bio-Sciences, NJ, USA), and signals were detected using BioRad ChemiDoc XRS imaging system (BioRad, CA, USA).

Statistical Analysis

For statistical analysis, GraphPad Prism (GraphPad Software, CA, USA) was used. Significance between groups was determined through one-way ANOVA analysis using Bonferni's multiple comparisons. $P<0.05$ indicates statistical significance.

Experimental Results

Example 1. Sequence Analysis of ANP32 Family Gene

As compared with human ANP32A (hANP32A), chicken ANP32A (cANP32A) contains additional amino acid residues 176 to 208, which are duplicated from amino acid residues 149 to 175 (27 residues). However, the functional role of the 27 amino acid residues of hANP32A has not yet been studied. Therefore, based on the comparison between hANP32A family members, it was attempted to find key amino acid residues contributing to viral polymerase activity through modification of 27 residues. As a result of investigating the sequence identity of the amino acid residues 149-175 of hANP32 family members through pairwise sequence alignment, it was found that the percent of identity of hANP32A with hANP32B, hANP32C, hANP32D, and hANP32E was approximately 68.3%, 86.1%, 89.3% and 56.6%, respectively. Next, as a result of investigating the sequence identity of N-terminal leucine rich repeat (LRR) and C-terminal low complexity acidic region (LCAR) domain through pairwise sequence alignment, it was found that the percent of identity of LRR and LCAR domains of hANP32A with LRR and LCAR domains of hANP32B, hANP32C, hANP32D, and hANP32E was 81.1%, 87.2%, 89.3%, and 71.6%, respectively. In the LCAR domain, the percent of identity of hANP32A with hANP32B, hANP32C, and hANP32E was about 4.7%, 84.4%, and 43.7%, respectively (hANP32D was excepted because the LCAR domain is not present in hANP32D).

Example 2. Construction of Recombinant Vector Targeting cANP32A Through CRISPR/Cas9 System A CRISPR/Cas9 vector targeting the cANP32A gene was produced using a pX459 vector in the same method as in the previous study (Lee et al., Dev Comp Immunol, 2017). The sequences of all oligonucleotides used for PCR analysis and CRISPR/Cas9 vector production are shown in Table 1.

TABLE 1

| ID | Sequence (5'-3') | Use | Sequence ID No. |
|---|---|---|---|
| ANP32A ex1-F | CACCGGCGACGATGGACGGGACGAG | Sequencing | 5 |
| ANP32A ex1-R | AAACCTCGTCCCGTCCATCGTCGCC | Sequencing | 6 |
| ANP32A ex4/5-F | CTGTCTGTCCTGTAGAGGTTTA | Sequencing | 7 |
| ANP32A ex4/5-R | GTCTTCCTCCTTCCAGTCTCT | Sequencing | 8 |
| ACTB qRT-F | AGGAGATCACAGCCCTGGCA | RT-qPCR | 9 |
| ACTB qRT-R | CAATGGAGG GTCCGG ATTCA | RT-qPCR | 10 |
| viral M qRT-F | AACCGAGGTCGAAACGTACG | RT-qPCR | 11 |
| viral M qRT-R | CGGTGAGCGTGA ACACAAAT | RT-qPCR | 12 |
| A#1 gRNA | AAAGGATCCACTTAGAGCTG | gRNA sequence | 13 |
| A#4 gRNA | CCACAACTCACATACCTCGA | gRNA sequence | 14 |

Briefly, the annealed oligonucleotide for each gRNA was ligated to the pX459 vector through the Golden Gate assembly method, and the prepared CRISPR/Cas9 vector was analyzed through Sanger sequencing. For homology directed repair (HDR)-mediated precise gene editing of cANP32A, double-cut donor-mediated HDR was performed using a donor plasmid (Bionics, Seoul, Korea) in the same method as in the previous study (Park et al., J Infect Dis, 2019). The HDR donor plasm id for amino acid residue substitution of D149Y, D152H, D182Y, and D185H is a target genetic locus with two gRNA-PAM sequences on flanking, and 400 bp of homology arms on the right and left are included. The gRNA sequence targeting cANP32A exon 4 (A #4) between the homology arms of the donor plasmid on right and left was modified to prevent further cleavage after HDR.

Example 3. Transfection of Fibroblast Cells Using Recombinant Vector

The CRISPR/Cas9 recombinant vector produced in Example 2 was mixed with Lipofectamine 2000 reagent (Thermo Fisher-Invitrogen) in Opti-MEM (Thermo Fisher-Invitrogen), and the mixture was introduced and transfected to chicken fibroblast cell line DF-1 (CRL-12203; ATCC, VA, USA). DF-1 used at this time was maintained in DMEM (Hyclone, Logan, Utah, USA) medium to which 10% fetal bovine serum (FBS; Hyclone) and 1× antibiotic-antimycotic (ABAM; Thermo Fisher-Invitrogen, Carlsbad, CA, USA) were added. After transfection, puromycin (Thermo Fisher Scientific) was added to the culture medium for 4 days to select transfected cells. The puromycin-selected single DF-1 cells were inoculated into individual wells of a 96-well plate. After clonal expansion of each single DF-1 cell, genomic DNA was extracted from the clone and used for sequence analysis.

Example 4. T7E1 Analysis and Genome DNA Sequence Analysis

To evaluate the target efficiency of CRISPR/Cas9 in the transfected DF-1 cells produced in Example 3, T7 endonuclease 1 (T7E1) analysis was performed. The primer sets used for amplification of the genomic region including the CRISPR/Cas9 target site are shown in Table 1. To form heteroduplex DNA, amplicons were reannealed after denaturation, and the reannealed heteroduplex amplicons were digested with T7E1 (New England Biolabs) enzyme at 37° C. for 20 minutes. The product digested with T7E1 was analyzed by 1% agarose gel electrophoresis. For sequence analysis, the PCR product containing the target site was cloned into pGEM-T Easy vector (Promega, WI, USA), followed by sequencing using an ABI Prism 3730 XL DNA analyzer (Thermo Fisher-Applied BLAST Biosystems, CA, USA). For sequence analysis, (blast.ncbi.nlm.nih.gov) and Geneious R6 software (Biomatters Ltd.) were used.

Figure 1C:
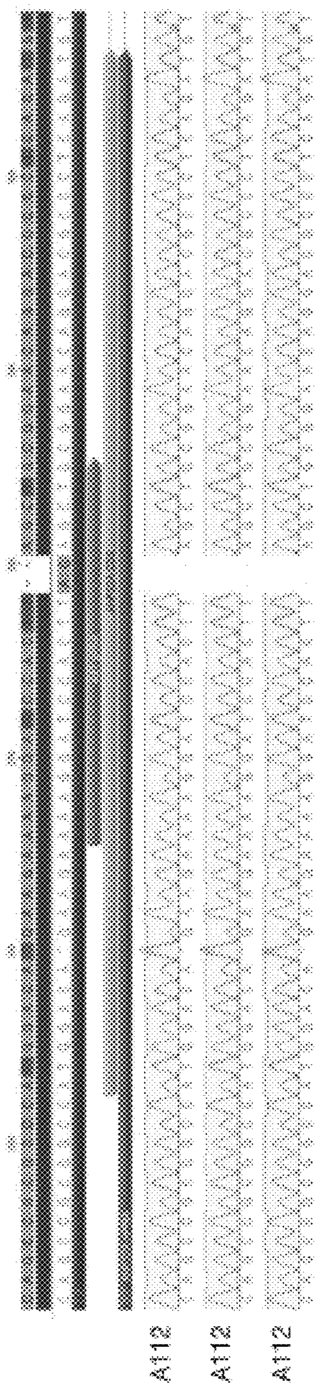

Specifically, the CRISPR/Cas9 vector targeting exon 1 of cANP32A (A #1 vector) was prepared to investigate whether hANP32 family members may be involved in replication of avian influenza in cANP32A-knockout DF-1 cells (A_KO) (FIG. 1A). The A #1 vector was transfected into DF-1 cells, genomic DNA was isolated from the transfected cells, and T7E1 analysis was performed. As a result, it was confirmed that the DF-1 cells transfected with the A #1 vector had an in-del (indel) mutation in exon 1 of cANP32A (FIG. 1B). In addition, as a result of genomic DNA sequencing, it was confirmed that the mutation rate was 81.8% (9/11) (FIG. 1C). After culturing individual DF-1 clones, the A_KO112 DF-1 clone in which 2nt was deleted from exon 1 of cANP32A was used as a representative A_KO cell in subsequent experiments.

Figure 2A:
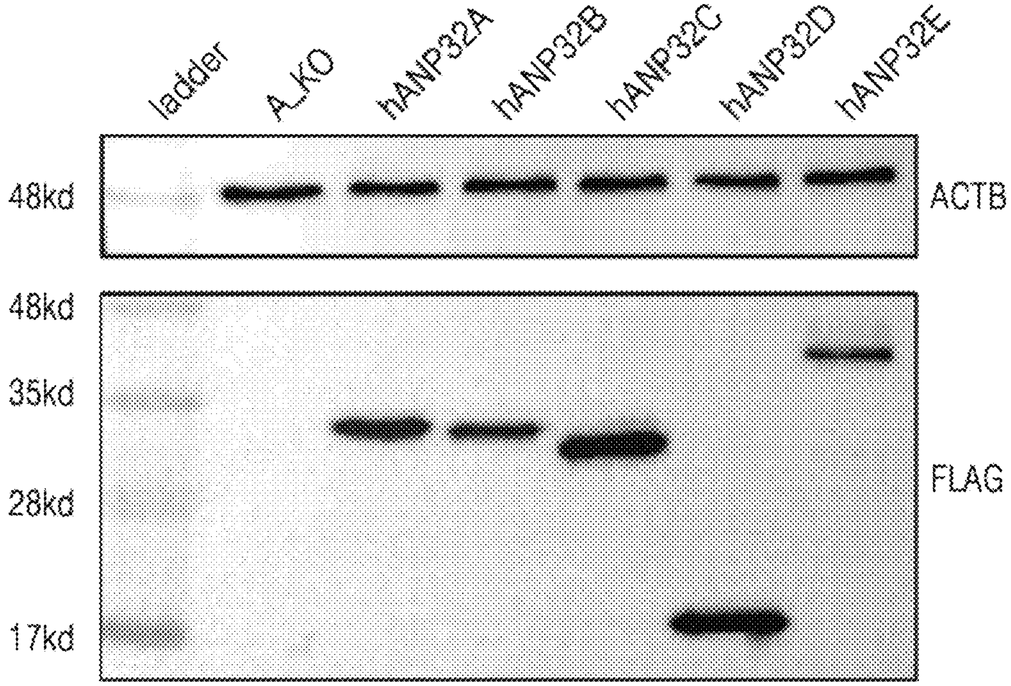
FIGS. 2A, 2B, 2C and 2D shows results of analysis of functional significance of amino acid residues 149 to 175 of human ANP32 family members for viral replication and viral polymerase (vPol). (2A) shows results of Western blot analysis using an anti-FLAG antibody, in which overexpression of human ANP32 family members including hANP32A, hANP32B, hANP32C, hANP32D, and hANP32E were confirmed in ANP32A-deficient (A_KO) chicken DF-1 cells. (2B) shows results of determining viral titers by $TCID_{50}$ analysis after infecting each A_KO cell expressing hANP32 protein with PR8-H5N8 (PB2-627E, or PB2-627K) influenza virus (MOI 0.1). (2C) shows results of multiple sequence alignment of amino acid residues 149 to 175 of hANP32 and chicken ANP32 (cANP32) family members. The percentage of identity to amino acid residues 149 to 175 of cANP32A is indicated. All protein sequences are sorted using Blosum62 scoring matrix in Geneious software (black: 100%; dark gray: 80% to 100%; and light gray: 60% to 80%; white: <60%). (2D) shows the forced expression effect of hANP32A, hANP32A_27 del, hANP32A_27 C, hANP32C, hANP32C_27 A, hANP32E, or hANP32E 27A on viral gene expression in A_KO cells after infection with PR8-H5N8 (PB2-627E). A_KO cells (empty) transfected with an empty vector were used as a control. Data are expressed as mean±standard deviation (n=3). *P<0.05, P<0.01, *P<0.001, and ****P<0.0001. ns=non-significant.

Example 5. Functional Effects of ANP32 Family and Effects of ANP32 Mutations on vPol Activity In order to identify whether mutations induced at residues 149 to 175 in an ANP32 protein may affect viral polymerase (vPol) activity of avian influenza, an overexpression vector carrying the cANP32A or codon-optimized hANP32A, hANP32C, or hANP32E sequence expressed by a cytomegalovirus (CMV) promoter was constructed in the same method as in the previous study (Park et al., J Infect Dis, 2019). Modification or gene swapping experiments of residues 149 to 175 of ANP32 protein were performed using a Q5 site-directed mutagenesis kit (New England Biolabs, MA, USA). All plasmid constructs were verified by DNA sequencing. For transient expression of the modified ANP32 protein, the constructed vector was transfected into DF-1 cells using Lipofectamine 2000 reagent (Thermo Fisher-Invitrogen). After 48 hours of transfection, expression of hANP32 protein in A_KO cells was verified by Western blot (FIG. 2A). Then, the transfected cells were infected with recombinant avian influenza viruses PR8-H5N8 PB2-627E and -627K for 24 hours to analyze virus replication and proliferation.

Figure 2B:
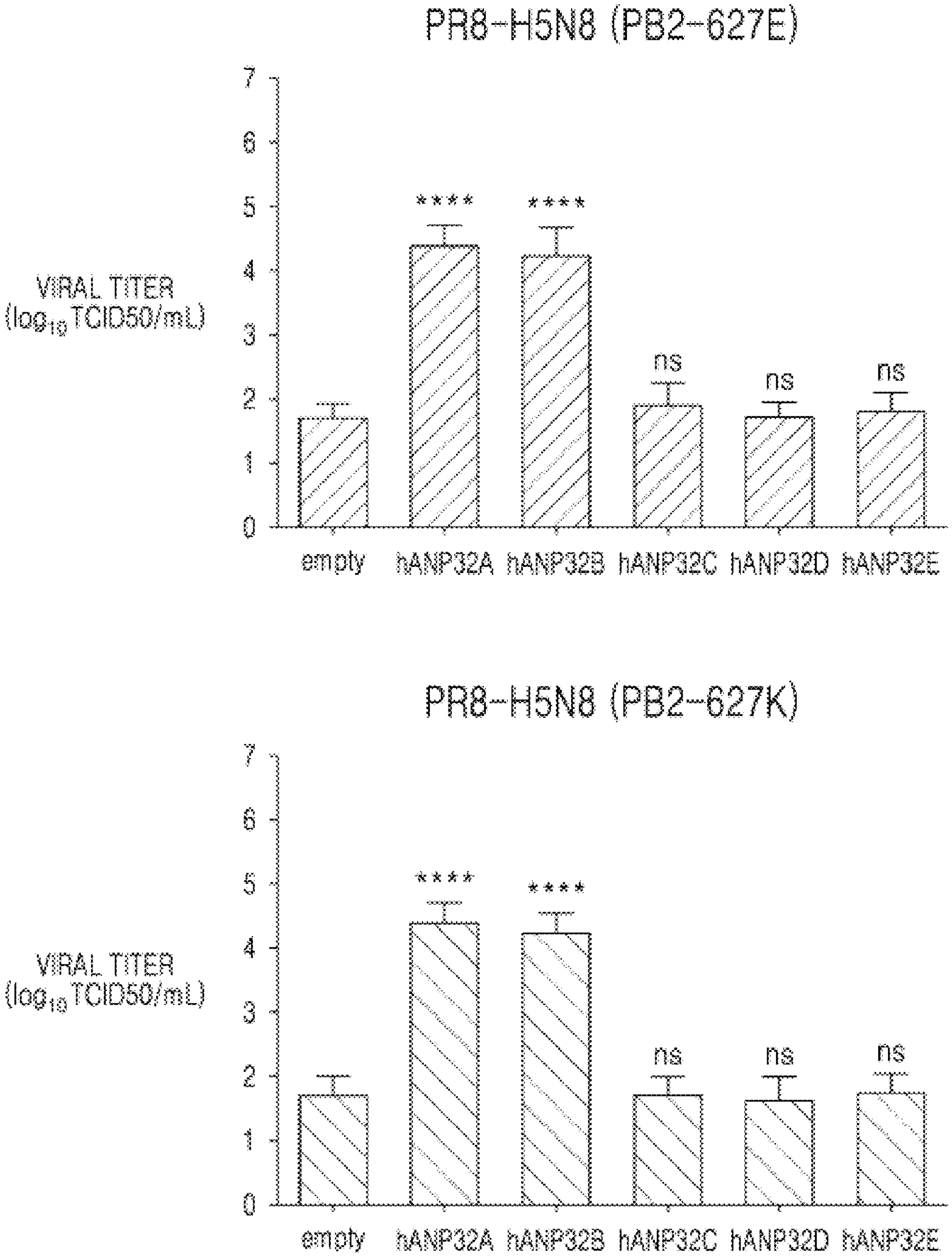

As a result, it was confirmed that hANP32C, hANP32D, or hANP32E overexpression did not contribute to virus replication, whereas hANP32A and hANP32B expression enabled virus replication in A_KO cells regardless of PB2-627 residue (FIG. 2B). The results show that hANP32C shares a higher sequence identity with hANP32A, as compared with ANP32B, however, unlike hANP32A and hANP32B, hANP32C does not efficiently participate in virus replication of AIV.

Figure 2C:
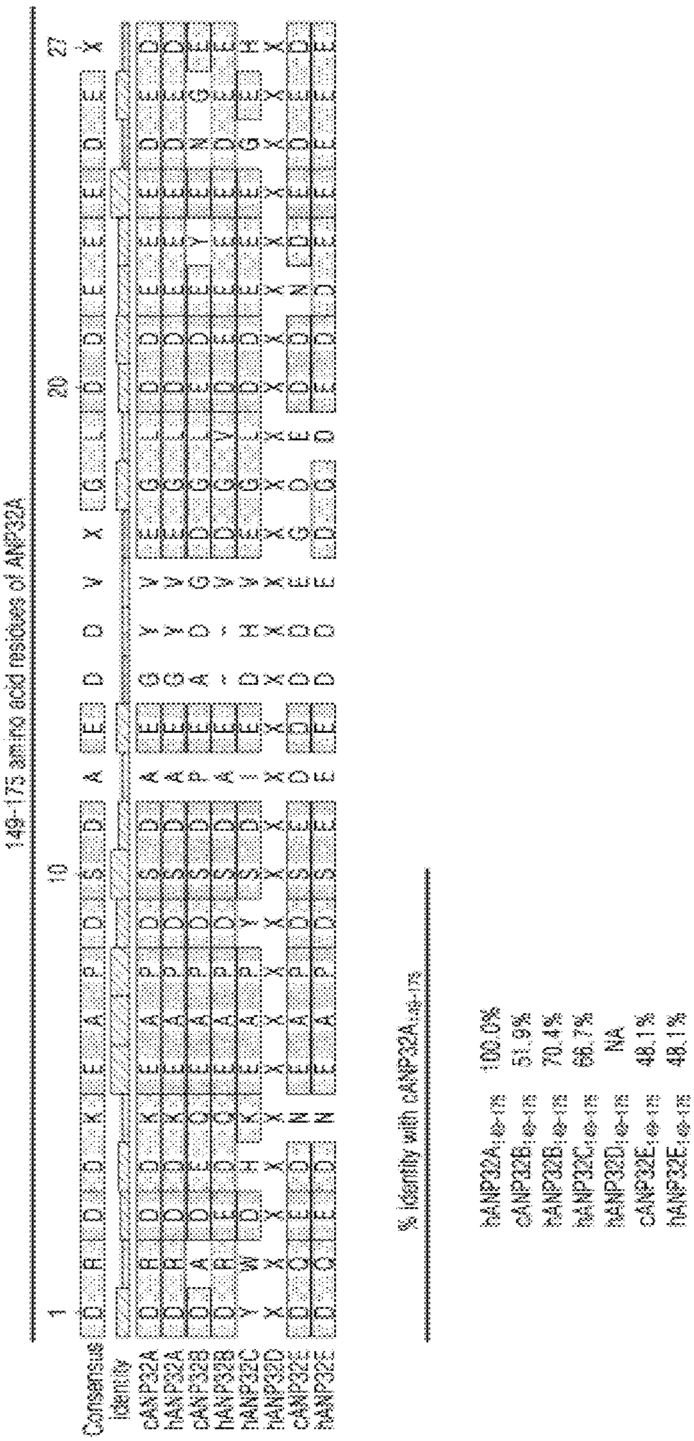

Next, to analyze functional significance of 27 residues for vPol activity, residues 149 to 175 of human and chicken ANP32 proteins were aligned. As a result, it was confirmed that the sequence identity of the 27 residues varied from 48.1% to 100% in the ANP32 family members of human and chicken. Specifically, the sequence identities between cANP32A and hANP32A, cANP32B, hANP32B, hANP32C, cANP32E, and hANP32E were 100%, 51.9%, 70.4%, 66.7%, 48.1%, and 48.1%, respectively (FIG. 2C).

Figure 2D:
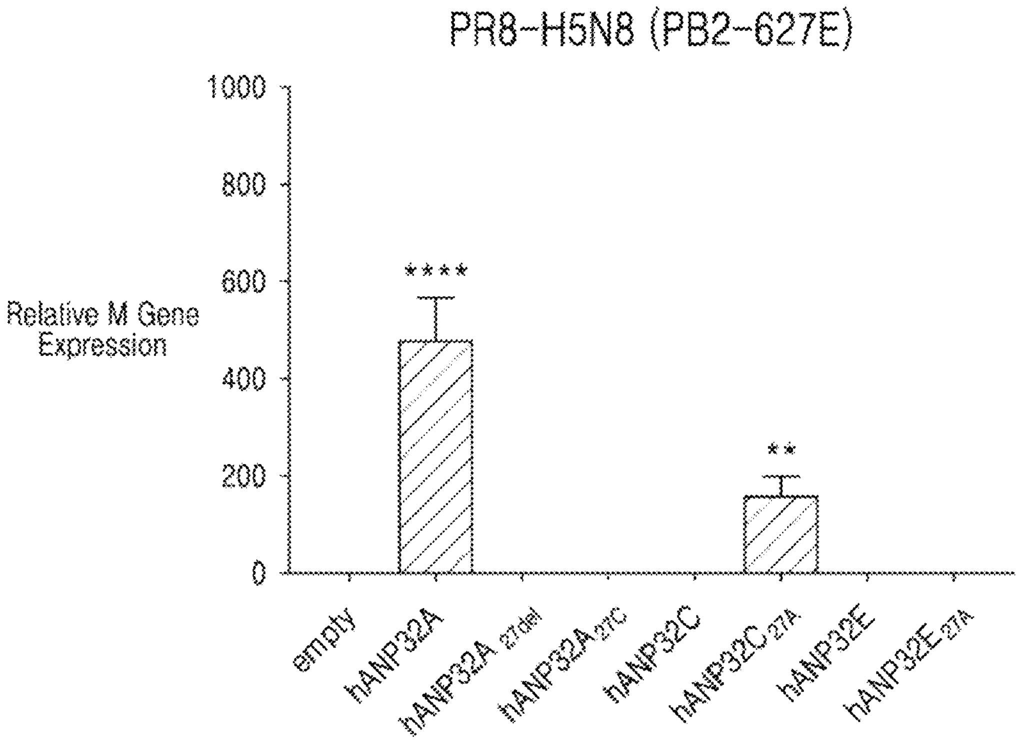

In this regard, an analysis was performed to identify whether different residues between hANP32A and hANP32C have a differential role in vPol activity and virus replication. First, a vector from which residues 149 to 175 of hANP32A were removed (hANP32A27del), a vector from which residues 149 to 175 of hANP32A were replaced with residues 149 to 175 of hANP32C (hANP32A27C), a vector from which residues 149 to 175 of hANP32C were replaced with residues 149 to 175 of hANP32A (hANP32C27A), or a vector from which residues 149 to 175 of hANP32E were replaced with residues 149 to 175 of hANP32A (hANP32E27A) was constructed. After transfecting the constructed vectors into A_KO cells, the cells were infected with H5N8-627E, and the expression level of the virus gene was analyzed using RT-qPCR. As a result, it was confirmed that overexpression of hANP32A27del, hANP32A27C, hANP32C, hANP32E, or hANP32E27A did not contribute to virus gene transcription, whereas overexpression of control hANP32A or hANP32C27A could contribute to virus gene transcription in A_KO cells. In particular, for hANP32C, it was shown that the vector (hANP32C27A) in which 27 residues of hANP32A were replaced may contribute to vPol activity, but hANP32E27A did not contribute to vPol activity. It was found that the remaining domains LRR and LCAR are also essential to vPol activity, in addition to the 27 residues (FIG. 2D).

Figure 3A:
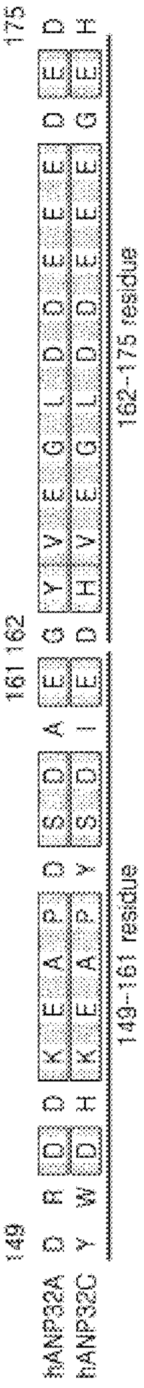
FIGS. 3A, 3B, 3C and 3D shows results of identifying key residues involved in influenza virus replication among amino acid residues 149 to 175 of ANP32A protein. (3A) shows results of pairwise sequence alignment of amino acid residues 149 to 175 of human ANP32A (hANP32A) and hANP32C. (3B) shows that viral titers measured after overexpression of hANP32A in which amino acid residues 149-161 or 162-175 of hANP32C were exchanged with the corresponding amino acid residues of hANP32A (149-161C and 162-175C, respectively) in ANP32A-deficient (A_KO) chicken DF-1 cells and infection of the cells with PR8-H5N8 (PB2-627E) influenza virus (MOI 0.1) for 24 hours. (3C) shows viral titers measured after overexpression of single amino acid-modified hANP32A containing D149Y, R150W, D152H, D157Y, and A160I in ANP32A-deficient (A_KO) chicken DF-1 cells and infection of the cells with PR8-H5N8 PB2-627E influenza virus (MOI 0.1) for 24 hours (upper image), and viral titers measured after overexpression of hANP32B or D149Y and D152H-modified hANP32B (hANP32BY149H152) in A_KO DF-1 cells and infection of the cells with PR8-H5N8 PB2-627E virus for 24 hours (lower image). (3D) shows results of pairwise sequence alignment of amino acid residues 149 to 161 of hANP32A and hANP32B. Data are expressed as mean±standard deviation (n=3). *P<0.05, P<0.01, *P<0.001, and ****P<0.0001. ns=non-significant.
Figure 3B:
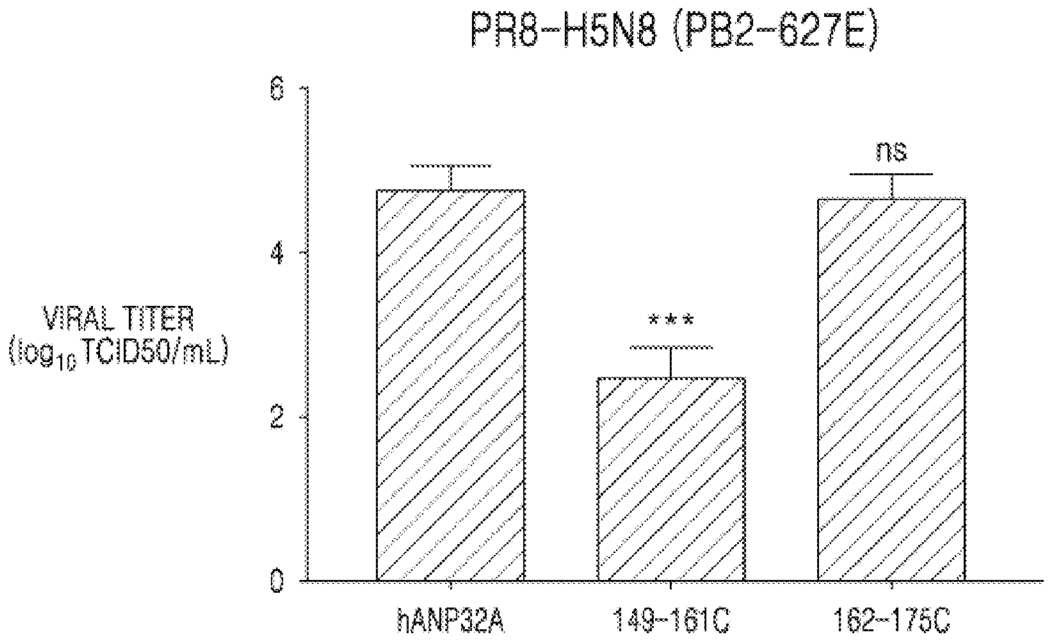

Example 6. Identification of Key Amino Acids of ANP32A Involved in vPol Activity In order to identify key amino acid residues among the 27 residues involved in vPol activity and virus proliferation, the ANP32A sequence was mutated. First, hANP32A residues 149 to 161 and 162 to 175 residues were replaced with 149 to 161C and 162 to 175C regions of hANP32C, respectively, to produce h32A (FIG. 3A). As a result, as compared with the expression of hANP32A in A_KO cells, it was confirmed that the expression of 149 to 161C in hANP32A showed a significant decrease in the virus titer of AIV, whereas the expression of 162 to 175C did not show a significant difference (FIG. 3B).

Figure 3C:
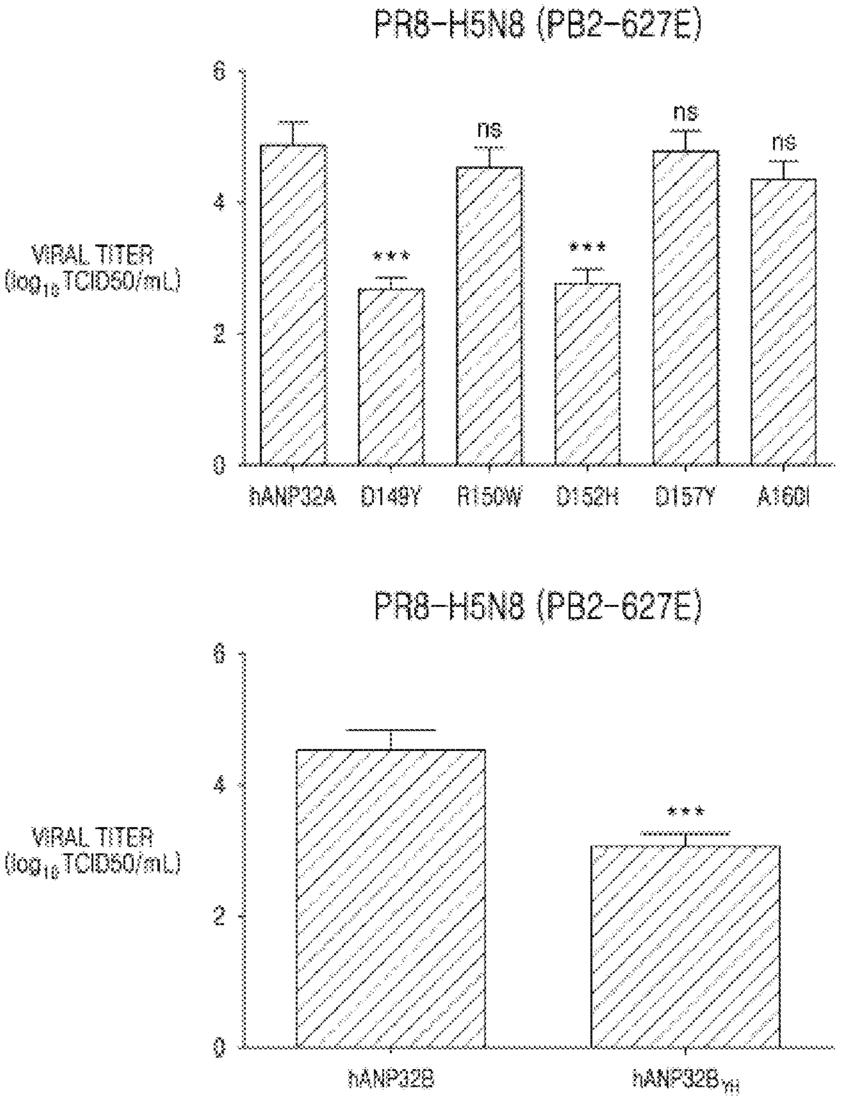

Next, through pairwise sequence comparison between hANP32C and hANP32A including D149Y, R150A, D152H, D156Y, and A161I substitutions, it was investigated whether single residue substitution may inhibit AIV replication. As a result, it was confirmed that substitution of D149Y and D152H in hANP32A significantly reduced the transcription level of the virus gene. From the results, Asp149 (D149) and Asp152 (D152) were found to be key amino acid residues involved in vPol activity and virus proliferation. Additionally, as a result of overexpressing hANP32B-modified protein in A_KO cells and analyzing the virus titer, it was confirmed that D149Y and D152H substitution (hANP32BD149Y/D152H) in hANP32B significantly reduced the virus titer of AIV, as compared with overexpression of wild-type hANP32B (FIG. 3C).

Figure 3D:
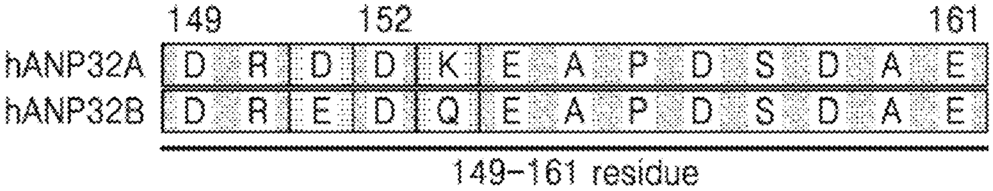

To confirm whether the functional roles of D149 and D152 are conserved in both hANP32A and hANP32B, pairwise sequence alignment of residues 149 to 161 was performed. As a result, it was confirmed that D149 and D152 were conserved in both hANP32A and hANP32B (FIG. 3D).

Example 7. Effect of Protein Interaction on vPol Activity

Figure 4A:
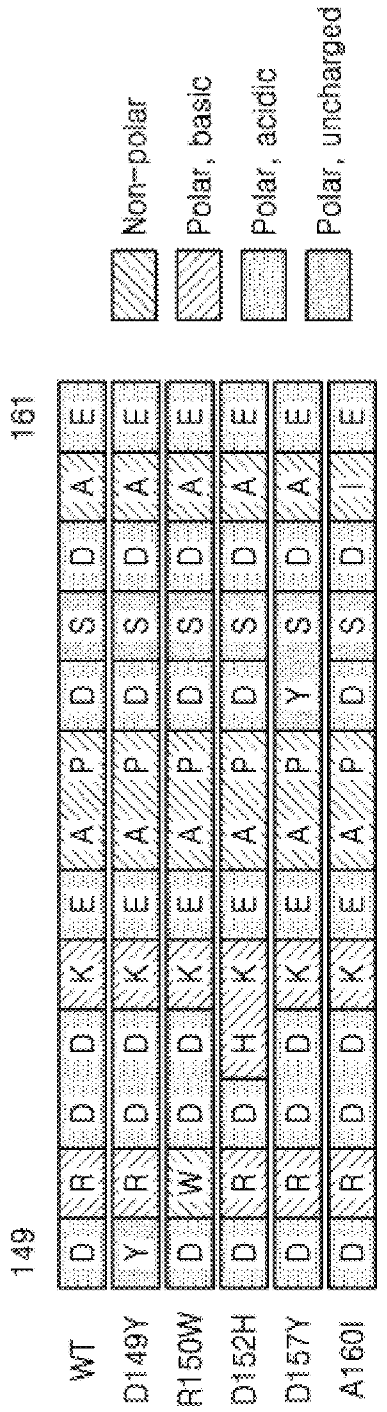
FIGS. 4A, 4B and 4C shows results of analysis of functional roles of D149 and D152 of ANP32A in relation to interactions with influenza virus PB2 proteins. (4A) is a schematic view of a polar mapping of D149Y and D152H substitution in human ANP32A (hANP32A). (4B) shows virus titer measurements after overexpression of single amino acid-modified hANP32A containing D149Y, D149A, D149E, D149N, D152H, D152A, D152E, or D152N in ANP32A-deficient (A_KO) chicken DF-1 cells and infection of the cells with PR8-H5N8 PB2-627E influenza virus (MOI 0.1) for 24 hours. Data are expressed as mean±standard deviation (n=3). *P<0.05, P<0.01, *P<0.001, and ****P<0.0001. ns=non-significant. (4C) shows results of co-immunoprecipitation analysis using a FLAG antibody on A_KO cells co-transfected with FLAG-tagged hANP32A wild-type (WT) or hANP32A_D149Y/D152H and a viral polymerase (PA, PB1 and PB2-627E or 627K) for 24 hours. Each cell lysate and FLAG-immunoprecipitated proteins (FLAG-IP) were analyzed by western blotting using the indicated antibody.
Figure 4B:
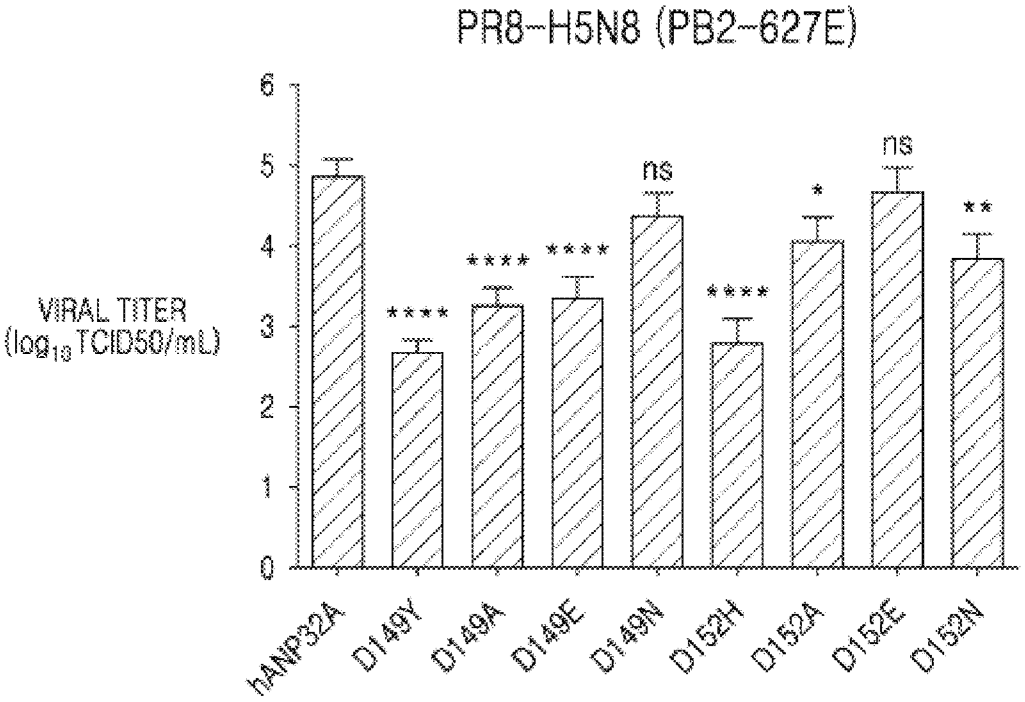

In consideration of a significant polarity difference at amino acid residues 149 and 152 between hANP32A and hANP32C, polarity mapping by the Geneious Program was used to focus on the polarity and charge of the residue to determine which molecular interactions were involved in the residue. (FIG. 4A). Then, residues 149 and 152 were substituted with representative non-polar alanine (A), polar acid glutamate (E), and polar non-charged asparagine (N), respectively. As a result of overexpressing the hANP32 mutant protein in A_KO cells, it was confirmed that D149Y, D149A and D149E significantly reduced the virus titer, whereas D149N showed no significant difference, as compared with wild-type hANP32A. In addition, while D152H, D152A, and D152N significantly reduced the virus titer, it was confirmed that D152E did not show a significant difference, as compared with wild-type hANP32A (FIG. 4B). From the results, it was found that residues D149 and D152 were involved in vPol activity through hydrogen bonding and electrostatic interaction, respectively.

Figure 4C:
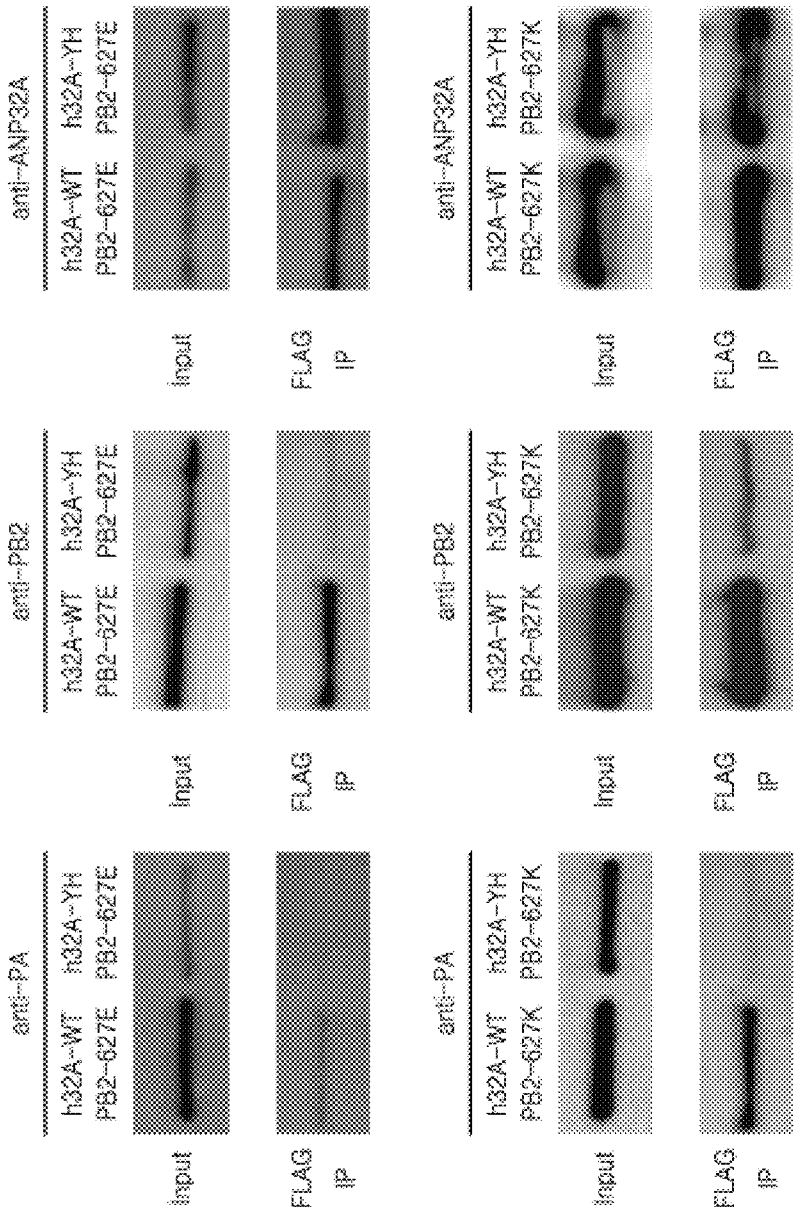

In order to confirm whether the mutation of the identified residue affects the protein interaction between ANP32A and vPol protein, additional immunoprecipitation analysis was performed. Specifically, the interaction between wild-type or mutant hANP32A and vPol protein in A_KO DF-1 clone was analyzed. As a result, viral PA and PB2 proteins were co-immunoprecipitated with wild-type hANP32A (hANP32Awt). On the other hand, it was confirmed that the hANP32AD149Y/D152H mutant exhibited reduced interaction with virus protein after anti-FLAG co-immunoprecipitation regardless of residue PB2-627 (FIG. 4C). Through the results, it was confirmed that mutations at residues D149 and D152 of hANP32A were involved in the interaction between ANP32A and vPol protein.

Example 8. Precise Gene Editing for Chicken ANP32A

Figure 5A:
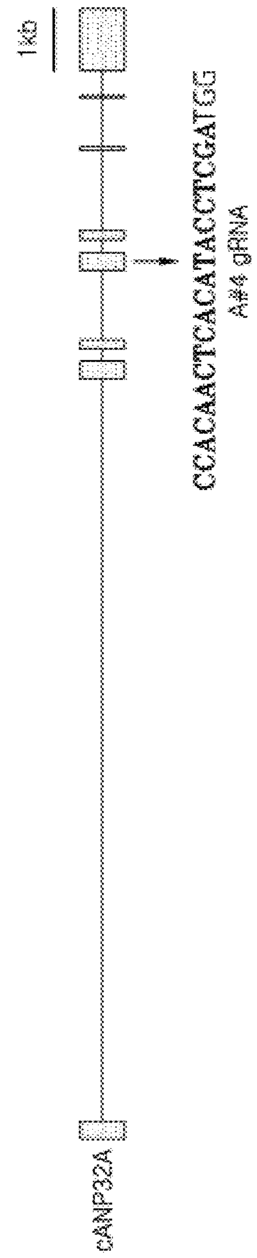
Figure 5B:
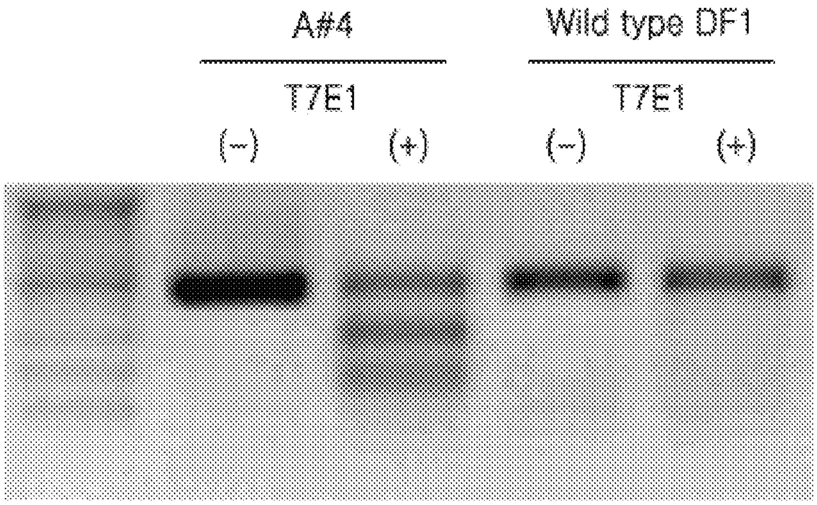

By using the CRISPR/Cas9 system, it was confirmed that precise substitution of amino acid residues for chicken ANP32A via homologous recombination significantly reduced virus replication in chicken cells. First, to target exon 4 of the cANP32A gene, DF-1 cells were transfected with CRISPR/Cas9 vector containing A #4 gRNA sequence, and it was confirmed that target efficiency was performed by T7E1 analysis and genomic DNA sequencing of transfected DF-1 cells. (FIGS. 5A, 5B, and 5C).

Figure 6:
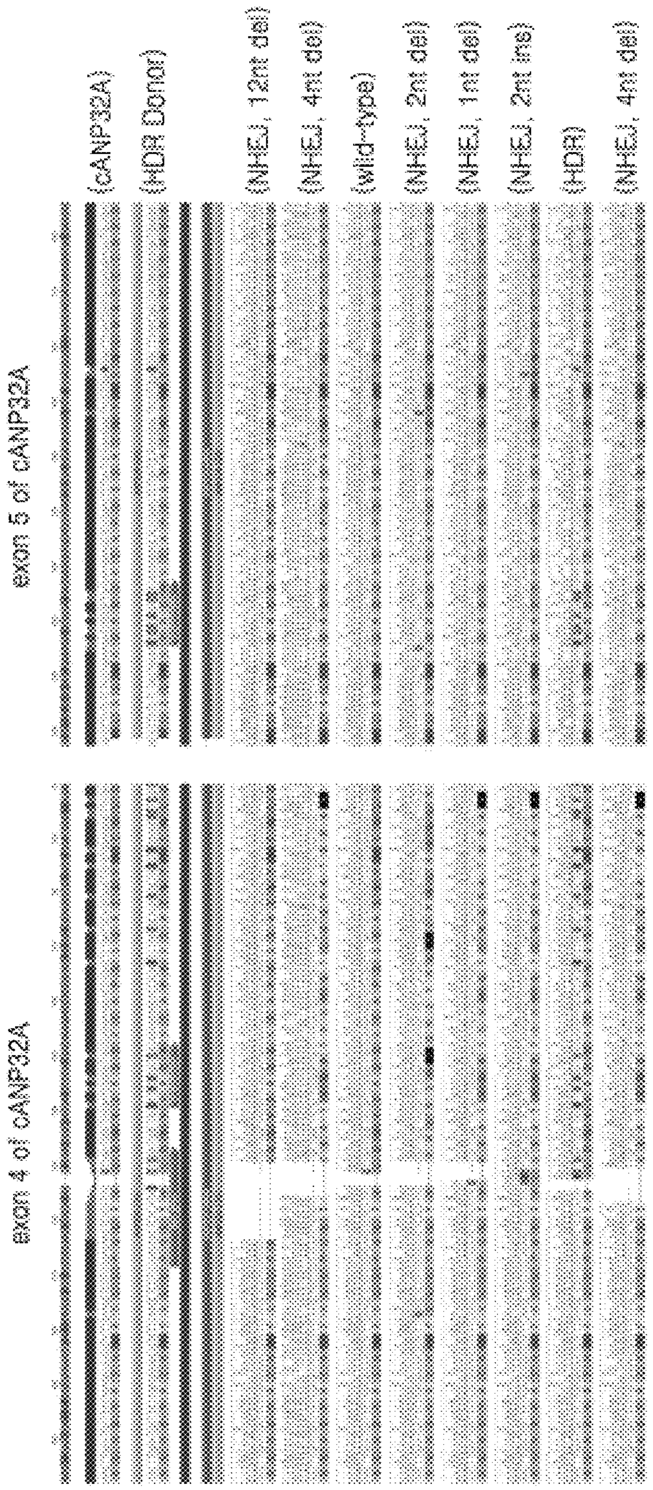
FIG. 6 shows results of HDR-mediated precise residue substitution of chicken ANP32A gene in DF-1 cells. The sequencing results of exons 4 and 5 of chicken ANP32A (cANP32A) obtained from transfected DF-1 cells are shown by using chromatography. cANP32A represents a wild-type sequence, and HDR donor represents an HDR donor plasmid sequence. In parentheses, non-homologous end joining (NHEJ) involving in-del or homology-directed repair (HDR) is indicated.
Figure 7A:
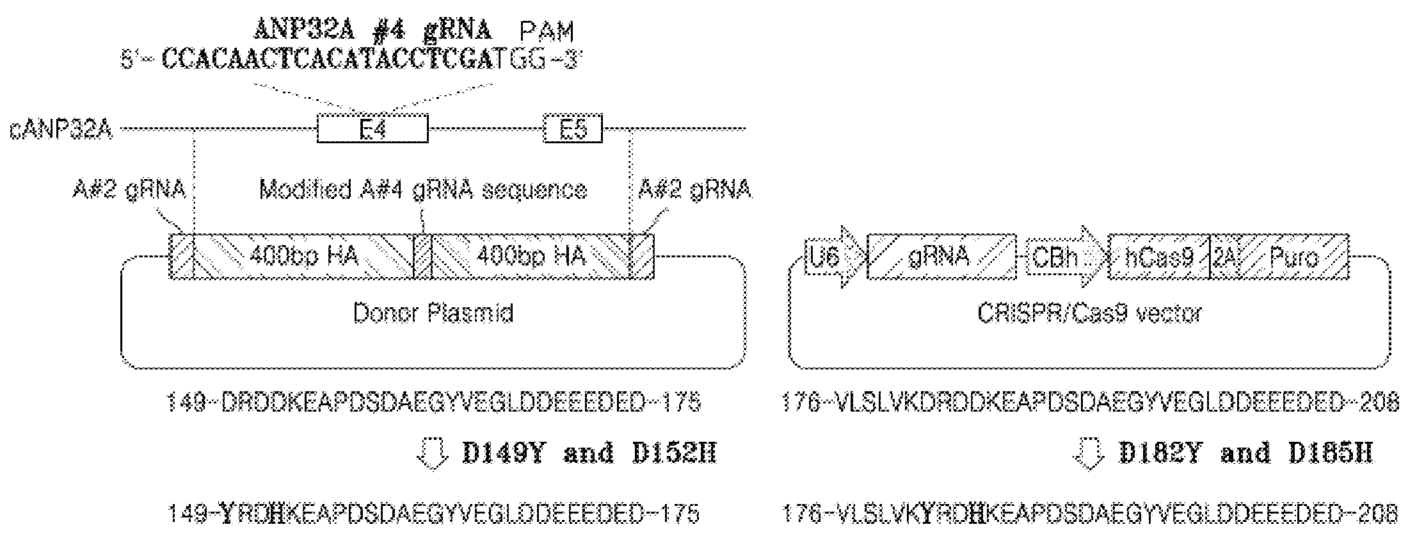

Because cANP32A has additionally cloned D182 and D185 residues, D149Y, D152H, D182Y, and D185H ($A_{YHYH}$) modifications were induced for the cANP32A gene using a double cut-mediated HDR system in the method as in the previous study (Zhang et al., Genome Biol, 2017; Park et al., J Infect Dis, 2019) (FIG. 7A). As a result of co-transfecting A #4 CRISPR/Cas9 vector and donor plasmid into DF-1 cells, it was confirmed that the HDR efficiency was about 11% (1/9) (FIG. 6).

Next, a DF-1 clone was established through single cell clone expansion of the transfected cell, and as a result of performing cDNA sequencing on the established clone, a clone ($A_{YHYH}$ 106) in which the target sequence was precisely substituted was confirmed (FIG. 7B). In addition, it was confirmed that $A_{YHYH}$ 101, $A_{YHYH}$ 102, $A_{YHYH}$ 104, $A_{YHYH}$ 105, and $A_{YHYH}$ 107 had a premature stop codon at exon 4.

Figure 7C:
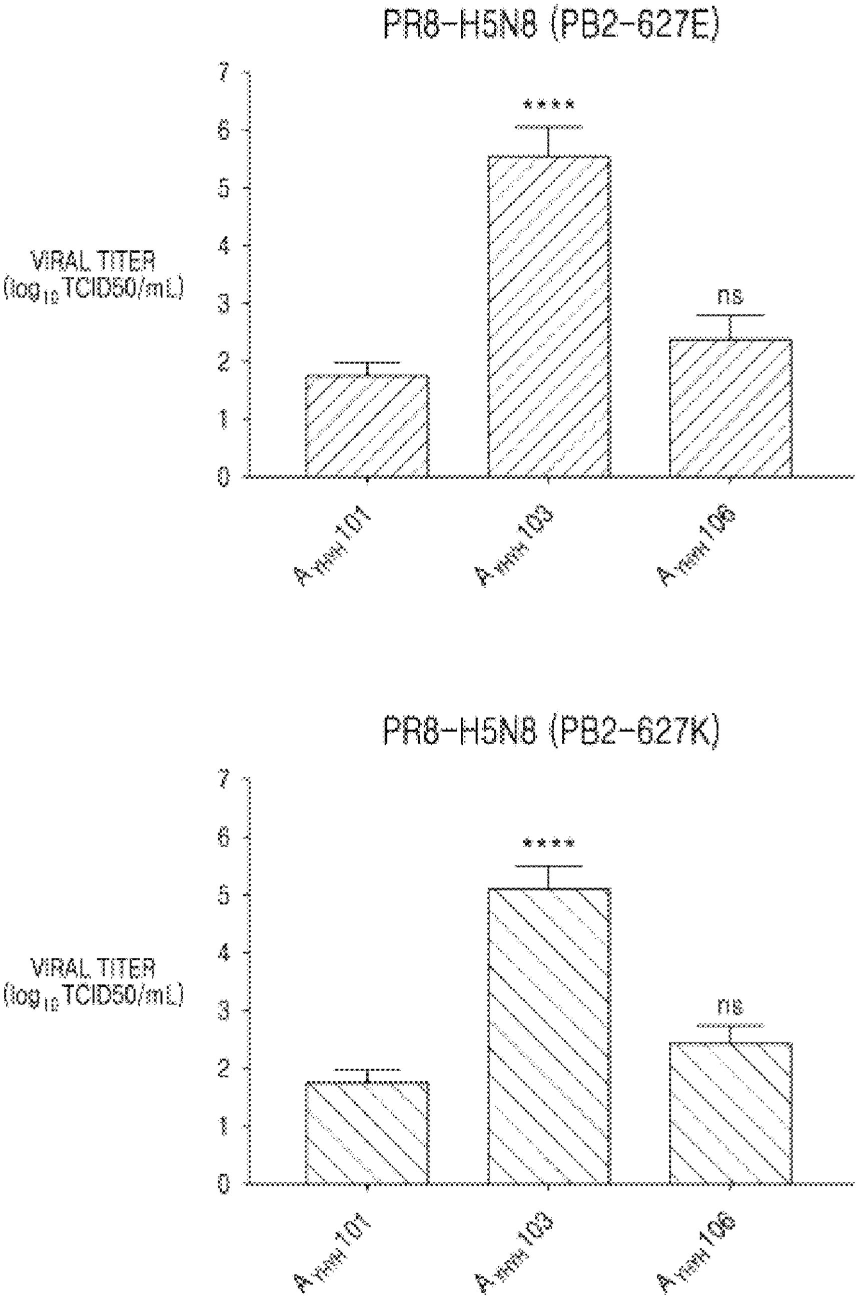

In order to evaluate the exact modification effect of cANP32A residue in DF-1, established cell clones including $A_{YHYH}$ 101 (premature stop codon), $A_{YHYH}$ 103 (wild-type), and $A_{YHYH}$ 106 (HDR) were used with MOI 0.1 PR8-H5N8 LPAI (PB2-627E or PB2-627K). As a result, it was confirmed that the virus titer in both $A_{YHYH}$ 101 and $A_{YHYH}$ 106 clones was significantly lower than in $A_{YHYH}$103 clone regardless of residue PB2-627 (FIG. 7C). From the results, it was confirmed that correct substitution with D149Y, D152H, D182Y, and D185H in cANP32A gene may significantly reduce AIV proliferation in chicken host cells.

Through the results, it was confirmed that the method according to one aspect may acquire resistance to avian influenza viruses (AIV) by inducing mutations in an ANP32A, which is involved in virus replication in host cells. In particular, by modifying only the key amino acid residue of ANP32A, it was confirmed that resistance to AIV may be acquired by precisely limiting only the interaction in the relationship with the AIV protein while maintaining the original function of the ANP32A gene. Therefore, the method according to one aspect may be widely applied to disease-resistant cell lines, disease-resistant poultry, and animal production.

As described above, specific parts of the present invention have been described in detail, and it will be apparent to of ordinary skill in the art that this specific description is only a preferred embodiment, and the scope of the present invention is not limited thereto. Accordingly, it will be said that the substantial scope of the present invention is defined by the appended claims and their equivalents.

This application contains references to amino acid sequences and/or nucleic acid sequences which have been submitted concurrently herewith as the sequence listing text file entitled "000009usnp_SequenceListing.TXT", file size 85 kilobytes (KB), created on 31 Mar. 2022. The aforementioned sequence listing is hereby incorporated by reference in its entirety pursuant to 37 C.F.R. § 1.52(e)(5).

What is claimed is:

1. A recombinant vector comprising a polynucleotide encoding a guide RNA (gRNA), wherein the guide RNA (gRNA) targets nucleotide sequences encoding amino acid residues of Asp149, Asp152, Asp182, and Asp185 in an Acidic Nuclear Phosphoprotein 32 Family Member A (ANP32A) gene to induce substitutions of the amino acid residues with Tyr149, His152, Tyr182 and His185, respectively.

2. The recombinant vector of claim 1, wherein the gRNA is represented by SEQ ID NO: 14.

3. The recombinant vector of claim 1, wherein the polynucleotide comprises a protospacer adjacent motif (PAM).

4. A genome-editing composition comprising the recombinant vector of claim 1 and at least one nuclease encoding sequence selected from the group consisting of CRISPR associated protein 9 (Cas9), CRISPR from *Prevotella* and *Francisella* 1 (Cpf1), a transcription activator-like effector nuclease (TALEN), and a zinc finger nuclease (ZFN), wherein the genome-editing composition induces nucleotide substitutions in the ANP32A gene that result in amino acid substitutions of D149Y, D152H, D182Y and D185H in the ANP32A protein.

5. The genome-editing composition of claim 4, wherein the composition is for inducing resistance to avian influenza viruses in host cells.

6. A transformed cell into which the recombinant vector of claim 1 is introduced.

7. The transformed cell of claim 6, wherein the cell is selected from the group consisting of stem cells, somatic cells, germ cells, and fertilized eggs, of a bird.

8. The transformed cell of claim 7, wherein the germ cells are primordial germ cells (PGCs).

9. The transformed cell of claim 6, wherein the transformed cell contains nucleotide substitutions in the ANP32A gene that result in amino acid substitutions of Asp149, Asp152, Asp182, and Asp185 in the ANP32A protein.

10. A method of producing a transformed cell, the method comprising introducing the recombinant vector of claim 1 into a bird somatic cell.

11. A method of producing a genome-edited bird comprising transplanting the transformed cell of claim 8 into an embryo of a bird.

12. The method of claim 11, wherein the bird is selected from the group consisting of chickens, ducks, geese, quails, pheasants, and turkeys.

13. The method of claim 11, wherein the genome-edited bird has resistance to avian influenza viruses.

14. A genome-edited bird having resistance to avian influenza viruses, produced according to the method of claim 11.

15. A transformed cell into which the genome-editing composition of claim 4 is introduced.

16. A method of producing a transformed cell, the method comprising introducing the genome-editing composition of claim 4 into a bird somatic cell.

* * * * *

SEQUENCE LISTING

<160> NUMBER OF SEQ ID NOS: 15

<210> SEQ ID NO 1
<211> LENGTH: 19259
<212> TYPE: DNA
<213> ORGANISM: Artificial Sequence
<220> FEATURE:
<223> OTHER INFORMATION: cANP32A

<400> SEQUENCE: 1
gagcccccac ctccgcagtt atcaggttag tgttcgccgc ggcgctgggg ctcgggattc 60
cgagcggcgc tggttgagcc ctcaaagtcc cttattaccg cgcgggctga gggggggtct 120
gcggcggtgt caccacacgg agcggagccg gggacagcga gcgcctcccg ccagccgcgg 180
ccatggacat gaagaaaagg atccacttag agctgcggaa caggacgccc tcagatgtaa 240
gcaaaaaaaa aaaaaaaaaa aaaaaaaaaa aaaaaaaaaa aaaaaaaaaa ggcagctcat 300
ctatctatat tttttatttt ttattaaagg gaaggggggg ccgccttcaa agctccgtgc 360
ccgagaagag ggccgcgggc cgggcgctgc ctcctgcgtg gggcgggggg ggggtcctca 420
cctcacgcct cgcacccggg gggcgacccc agcgcggggc cgggggggga acggccgagt 480
tgtggcgccg gtgggggggg cgagttgtgc cggggggggt ccggagcgcg gcgggtgtgt 540
gcgcggcggg cgggcgcgga ggctggggag ccatatttgt aactttgtgg tgctcatgaa 600
cgcgcccttt ctctctcctc ctctctccct cccgatgctg aggggggggaa agggtgaaag 660

-continued

```
ggttcggggg agcgccggcg tggcgatggg ggagcgggga attaaagaag gaagcggtaa    720
taaaaacaac gattgcgagg gagagaatgc gctccgcacc tctccatccc cgcacgctca    780
gaagggccgg gtgcgtgtgt atgtgtatgt gtctgtgtgt gcgtgttttc cccttttttc    840
ggattatttt taaccccat ccccgtacct cggggccgtg gttcagcctc tccccgagca    900
aagcggccga gaaactttgt caggacgaaa atagtcggcg cccggggggt gccccgaggc    960
gggcggcccc aaccccgagc cccgctccga gggtggcggc ggcggcggcg ggcttcgaac   1020
ccgcggcccc gagcgcggcg ccccccggcc tcctcctgcg cccgcggagg ctgagggcgg   1080
cggtggggtc cgcgccgagg gcgggggga gcgcggctga atggaacgta cctctcgggg   1140
aggagggcgg aggcggatgg atggatggaa gctgctcttt aaactttaaa aagtcctggg   1200
ccgggaggag gaggagggca cgcggcgcgg ccgtcccgcg gggctcattg tcccctctgc   1260
gggggcacaa agcgggcgga gagccgaacc gctccccgcg ccgctcccgg ggccgtctcc   1320
aggcgcgggc agcgcaagta ggacgcggcg ccatgttttt ttcccctccc gagctctgag   1380
ggaggaggag gaggaggaga aggagggcgg ttgggccctc cccgccgctc cgcgctcccc   1440
tccgtgccgg gcgggggttc ccctccgcga gggccgcctc ggagccctca cgctgctcgg   1500
ttgtggcggt ggcagtggga tggggaggtg gggggtgcgg gggggtctgg gcgcgccata   1560
gcggagcgcg gccctcccct cccctcaggg ggcgcggcgg gggcggccgg ggcgcggagg   1620
ggctcctcca tgacggaccg ccgccgtctg ccattttgtc gccgctgtcg ccgggcggga   1680
ggaggttcct ggcggcgaga cgcggcggcg ggacgagcgg agggtaaagc gcggcctgct   1740
cctctcccac accccttccc ctccggcttt accgttggga tcgttttttt gacctcagtc   1800
cctctggggg gtgttggggc gggcgggggg atgggctttg cgcagggccc ggcgcggctt   1860
tgtcgttttt tattgttacc atcgttatct tggaagtatt ttttgtcttt attttgtttc   1920
ggcttttttc gcgtttattt gttttagttt ttgcctcttg ctctaccgct cgtgctgctg   1980
gaggcttaaa ttcagcgttt tgtgtggact cagccttgat cccaagtgtg ctgggtgcag   2040
gctgggctct ccccctcata catagttggt tcagctcctg ctctgactga aggaaagttc   2100
acagagcccc cattgagtgg tggttcggtg ctctgggagc cccactttga tggtggttca   2160
ctgctctgag agccccagtt tggtgctgtt tcattgcata gagaacccca actcaccgct   2220
gtgttgttgc ccctccgcag ttcagcagtc ctcgctgctg taaaataatg cttgtttaac   2280
ctgacgtctt tttttttttt ttttaacctc ttaaccttta attctatcgc tgtgttccac   2340
ttcccaaggt aacaaatgag atcataatcc gttctatagg taaacagttg cgcctgcata   2400
caaaggggaa ctgccctttg ggagtgctgc tctgtttaca gtcactcctg caaaaccatt   2460
gatcacggat gcttccacgt gctcttgtgt tgtggggagc taagggtgca ggtttgaact   2520
ccgttcctct aaagttcctg ttagaagaaa atgcagctaa atccagccag tgctccagag   2580
aaaacgtttg aagctgagtt ttagtgcaaa tataatgcca gatgtcattg attcatggat   2640
tttagtaaga tgtggagcat gaacaagatg gttctggacg ttgtgttaat ctctgctctg   2700
ataggcagac ggtgtttctt gtgtgatcca tgatggatca ttattttcaa agctttaaat   2760
gtaacgtaga taaatgttgg tgaaaacaag ggcacaaatg gaagcgtatt tactctttct   2820
tggagctgtt actgtatatg tgctgaagtt tgcagtgcct ctcacatttg atctattctg   2880
ttatcggagc ttgcagaatc aaaactttct gtaaatcaag gtttgataaa ggaatgttga   2940
taaggtgttt aagctcagaa agcccctctt actattttat gctttgggct aatacagttg   3000
```

-continued

```
tgtcaaatac tatgtaatac tgtacagcta gctacttcag ctgctcagtt acataaccct   3060
gcaaggttac atgttagcca ataaaatgta atataaatgt ctaaaagtat agtagctatt   3120
tcttcctcag actctgctgc tgttttatat gaagtcaatg ttggtgagca gtctggggtt   3180
atagtgcctg aaatttggtg ggttttgtgt gtgtgtgtgt tggtgagaaa tctgtttgtg   3240
gtgcctgaaa tatgtttttc tttgttgtac agcctgagct gaggtctcac atctgccttg   3300
caggcatttc cacttttttt aacccattat gtttaatggt cacttacagc agtgcacatg   3360
ctgtggccta tgacgctttg ctgatcttac cactgtcatc ttctattata ttacataaaa   3420
atgcctacta gaaattggtg agatccaacc attttacatg ggttttctcc aggccatcag   3480
cccatagtgg tgtaactact gaccacatgg ggctgggtgt gtttgtgggt gttgctgctc   3540
attcctattg tttgtaaccc agctcatctg ttcacacagg ctgtgcagtg aggtcagtat   3600
gaagggggac ttctcaacca tgggacacag aggcagtgtt tagaagttat gcacaaaact   3660
catctttgat ggcttactgc taccatgcag ttcacttagt ctgaggattt agtgctgctt   3720
ttgagagaag ctttatcagc gcaaatttat gacagagata aagcactgcc tgcaacgttg   3780
ggtatttctt acagtttttc taactttctg tttcacttta aaacttactt gaattgtgat   3840
ttccctctag tttactgtag gttttaacat tgaggggaat tacagtgcag gtgtttatgt   3900
gaagcattct cttgtatgaa ggatataaat aagagctctt ttctcaagct agttagttgg   3960
tgtgatgctc acagtaacag taaagacttt aaagtgatgc acattgcttc aaaaacctgc   4020
atttgaaaaa gtttgtgtat tggtatttgg taagtgggcc aggatgcaca cgtttactca   4080
tcccacactg aatagcatgc aaatggaaca gggatatgct gtaggttagc agcagtggga   4140
caagttgggt gcactgtagt gtgcagcggc atgcgatgag catgtagaaa ctctgttaaa   4200
tgtccagttt agcatggatt tttgcagact tggatcactt aaccacttat gtagctaaca   4260
gcagggtgta aatgtaacaa agaagtagct gaggtttttt tgccagcttc ctgggtttgt   4320
ataatagctg cttttcaaga ctctgaattt tttgatgcaa acctctgaaa tctgggtaga   4380
tgaatgggtg ttcgtcttgg aggagcccag aaatcaggct tacaggacgg gtgtgatatg   4440
tgtgagctgt cctcactgaa atgtaggcta gcttctcagc tgacaactgg caaatcctct   4500
taacctggac caagttgaag catgtgagag gaacgacaaa tataaaatta aaaataaaaa   4560
aaaaaacaaa gcaaccacct gatgatatat aaacctgatg ggaagtttct cagcatcagt   4620
ctcctggggt gtaggtgctg tggccgaatt aagtgtaact actttatctg tccttgcagc   4680
agagtttgtg cattatatat caatggattg aatcagtgat gcatttttag atgttcattc   4740
aaatggtgtc ataaatctag tccagacagc tggtgttgag tgcatcttcc cattttgttc   4800
cttctatgga gtgctcattc ctcctcacca tcctcctgac ctaagggtac aggtgttgtt   4860
cacttggaga agcctaaact gaatctgcaa tatctaagta ggtgctctgt actgaatgtt   4920
tctaagtgaa ggaaaggtag agcagggctg gtgccctaaa gagccaggga tggcagcgtg   4980
gtgtgctggg ctgcgctcag cagcctttgt gggctgacag ctcacctgga tgggcccagt   5040
cctgctctgt gactgctgca ggttgcagag gggggtgggg agcagttgtg tttgttgtgc   5100
tcagagtgat ggatgcttct cagctatttg tatgacatca ctggacctgc atgtgtgatt   5160
ttttttgtct ctgtgcttgc tctgccaccc ttcagacgaa atagctagta gactcatagc   5220
ttgtgggttt tatcactgtt gctaaaatca gtcgtggagt ccttgcatgt gtaaggatgg   5280
tgttttgaaa taagagtcct cagtgtttgc cttcacatca ctgtgcaagt tgtgttctct   5340
atgggagtac ttgtttgtcc gttaacttgt tctgttgaac acttcccctc tgaagccata   5400
```

-continued

```
aaaatgctag gaaaagctta tcttctgtgt gatttgctaa tgcattctgt agcagctgac   5460
atctttagag actgctttct gtataaacta tgcagctctt gaaattagta ttaatttaaa   5520
tacagagctt cttctttatg taaatcagtc gtttgttgct gagggcagtt tgatgcagct   5580
gaacaaagtg aagcagttca gctaaatact ttcaacttct aactgcagag ttttcaaatt   5640
gaagttgaga tgtgatctgc cttttggttc tgttttattt aatagtagct ggcagtgact   5700
gaagagcacc ttggatatgc tgtcaggcat gatggctctc acacagggaa gctgggatgt   5760
ggagctgatg tgcccccctt gaagtcacct gccccagcca ggagcagagc agagtgcttg   5820
gccagtgaaa aaggagaaga aagcaacatc agtgtgaatt ttagaaagca tttaacatga   5880
agattgagca atataatcac ttacagattt gaagcagtca gtgtctaaat taaatatttg   5940
gagtctttag agttttgctg ctaatgctag aaatgaaaac tagttctgtg cttttgaacg   6000
aagcagcttt ctgtgtcccc aaagtgtgtt ctctatttat taattagtgt gctgcttatg   6060
catatggcta cattgacctt gtaaatgtgt gaaagtatct tgatgtgacc cacggggttt   6120
cttgctgggg tgctgtttct tgaggaaggc agcagtaggt tatttttttt tttctggagg   6180
ttttttgatt gtggagatgc ttcttaatta gatacaaagg tgtagtcaga atcgttaaga   6240
ctcttaaccc ttctactgct tatgtatttc acttgctcca ttaggtttct ctcaggtgca   6300
gtgtgaaggg gcgtaaagtt ggctggagcc gaatgtgttg ctcttgggtc ctgtagctgt   6360
ggtatgtgaa atgttagagg gtagaaaaag taaagatctc tgagctatgc gagcaggctt   6420
agactgcctc agaagagaga gtagctttga taacagatgc ataaaaaaaa cctgcaatgt   6480
tttcttatct ctcttctgct ccttcccttt tcctgaggta gcggtgatgc agagtcctgg   6540
tacgctcact ttctgaaaaa gagatgcaga agatgaactc aaatatgaaa gtttggggtt   6600
gcatcactag gaggaagcct agatgaattt caaagcccag tagtagtttc acatgacctt   6660
gttgcaagac tttggagttc cagctcagct gaacacgtac aaaatgggca gaattagcag   6720
aagtggaaca ggttgccatt ggaccagcct gcactggaca ccgttctgct caccatctgc   6780
gaactgcatt gtttcaaaag ggccagttgg agagtgctgg tggaagggac agctgtgtta   6840
ggatttggag agttttgtag ggaactctgc aaacttcagc ctcaactgct ctgaagctct   6900
gacatgcacc aactgtttgg caagggtgag ctctgctcag gtacctcctg tccataatga   6960
tacgcaatgc tcataatgac aagggccaca tattaattcc atcccatgtc ttcccagctg   7020
tcactcactg cctctggtga catgattctc aagtgctctg cctgctgtat gtcctgctgc   7080
atctcagggg cattggtttg tgttccatgg cccttttttg agcagtgttt ctccttattc   7140
caggctttgc agatttctgc ccaatgcagt aatgaccaga gcctgtgcaa ggtaaatggt   7200
agttggctaa ctaactttca ttaagacaat tcaagcaagt aaaatctatt catttattgc   7260
atctcagctg ctcatagtga aaccttgagg agatgcatca aaatccagtg tcaaaagttt   7320
ttctggtaag gaaaaaacaa ctttgctact gtcacctgca gctggtgcct gtaagctcta   7380
ttctggctgt ctttctatgt gtgtaagttg gcgggcaggt tggaagctgc tgatgttttg   7440
gaattttccc ttccctgtta aattgatggt agaaaaaaaa aaaagtagtt gtggctcaat   7500
gatcacctct gagcatccca ctgtccaccc ctcctctgta tcactgtgca tgggcagcac   7560
ggccagggca tgcggtgatc caatgagcct gggatagctg agcagctctt tgcgtgccag   7620
ttaaggcacc tagcagtcct gtgcagctct aatttgagct agattgttcc atgttcttcc   7680
atctcactgt tttcaatcag gaggtgaact gtgcagacaa gttttgctgt ttggctgtat   7740
```

-continued cacagggtac tttaaggtga ccgaagatct atcgtgtatg caagtggcaa atggcatgtg 7800
gtgctatctt tatttaaaag tatgtttgtt aaaaatcagt tctttgcatg ggttatgttt 7860
tggtgaccat cttggagcag aagttgcatc ctgtctatgg tcattgggag caacttcatt 7920
tccacaaggt actgagtatg ctgttttgtt caagcgtttt tggagctagt gacattctgg 7980
gtagcatctg aaatgaagat ttttgcagca tttaagtcct tccaaagtaa ccttgaggga 8040
accttgtaaa agttgttcat ggaaagcatc ataccacccc tgtgcagtta aaacagcagg 8100
ctctgcaggg acttgtgcaa gatcttgagc cttgttggac acattctgcc cccagcaatg 8160
agaacatcct gactgcagag ggctggttgc tcttcagctt tggggcacaa actgagttga 8220
acagaacccc aaagagatca atttctgctc aaggatcacc agctctacat gggtacagat 8280
ccaggaactg gaatgagcac agtctttgtt ggactggtta caacagacag caaaaatctc 8340
tctttgtctt tactgcagag agatgcaggg ctttgcacag actgtgtgtg cttctgggag 8400
caaaaagttt caaagaccca aacccaagtg tcttgaagaa atgtctgcac aactaggaga 8460
gaataaaact ctctgctttc acaagtaatt tgtgcatggc ttccacttac cacagctggc 8520
ttcccttgct ttcccctccg tactttcaat tctctgcctt gttccagatg aagtttccat 8580
tgggttaata ggtgtgaagg acttatctca atgttcccct ggcatttggc tgggagcaga 8640
gcaaggcaga gttaacaccc tcatcttttc ctgtttctgg ggggtcaaaa tgccacacac 8700
tgagatatcc ctatcctagg ggcaccatat acagcaaaca cttcaaaagc atctgatcca 8760
ttgtgctgaa aatgagatgt tacagtctta gcagttctgc ttgtgaagcc acagaatggt 8820
acttgtactt gtaaatttgc cttttatctt ttaaaaattg tattcacagc tgtgtcctgt 8880
tgctttgtta agccttcaat cacagacctg gattcaggag cttagtccca cttctgggtc 8940
tccgtgccca ggggctgtag ggaaagtctc tacttcagaa agcttttttt aaatgctcct 9000
gtggaaatgc agattaaggg ttaaggtgat accttgtgct gcatagtagc tgtctgtaac 9060
tatattccct tgattgtgca tttagagtat ggtcgcagga aaaggagtga gtgagctggg 9120
gatcctcttg ctagggctgc catgaaattc agtcactgct tacgcgtgac tgcctgtact 9180
tggcctagaa ataggtttga gtcttgcagt atgcatggct atgttaagaa taccatacag 9240
cttaacgtgg taaccatact aggaaagaga taagagtccc tggttatcag tagtgcagag 9300
tgtgatgtca tgaaagtcct gaagagatac agaggatgct gtaatctgca gccagcagcg 9360
cagcatgtgt taacagtagc atgatgtcgt cttctgaaag cctctgagac tgtcgcaaat 9420
agacactggc atggccacag gagaaaaggt ccaaggcaca ctgtctcagg atttgttgaa 9480
gaagctgcaa tctgcttatg tgcatgcata tgaaaaccaa ggactggtac cagcaaacca 9540
cagtgcagtg ctgcagtggc agtgcgcaac tgagcaggaa gcacctgctc gagcagctgg 9600
cacccactgg acagagcaag gaggtgcagg gctgaatgtg agctgaacaa gaaggcagag 9660
cagctggctg gctaaggagt tctgggcaga tgaagctgta gagcatccct acccaagtag 9720
gtgaaggtac cttaccgtgg gtgctgttga agacatggtt gtttgcttca ggacctaacc 9780
tagctacatg cacgttaggt tttctggtag atactcatct gtgagtgcct tcttagctgt 9840
tttaagtatc acagtgtcat ctgcagtggt tggttgccta tggcatgttg cacttctgct 9900
ctttcttgct atatagcagt actctgggga gagagaggaa gagacaagca aaggtctgcc 9960
ttgtgttagc actacctata ttggtcctca ctccaattag tatgttgagt agtttgtaca 10020
ttgtgatgtg tacaatagta aggttgacca catgcaactt ctgcaagttg agtcttcctg 10080
tctttgcaac taaacacaag ctggctcagg gcacttatta cacttattac ctgctgtctc 10140

-continued tccaaacagg ttcatgttat tgtccttagt tccaactgtt catctacatc catgctatta 10200
cacagactgc agtgtgacac agccaggtgg gttcagacca gttgaagcct actcatctgg 10260
ctcaggctta tagcagggct caggaagggt gcttacatca tcaagggctg attctgtgtt 10320
ttggtgacac agtatgagga aagagaaagg taaaattaca gtcttgctgt gtgctgtcag 10380
ggtgttcatg ggaagttggg tagatgtttg gagggtgact tggagtggaa ttttcatttc 10440
aaattttgaa gacttctgca aacaaataga agcgtaatcc ttctctcacg gtagcgagct 10500
gttttgtgtg caatgtagct ttcctaaggt caccttttgc ttctttcctg cattctggac 10560
ccagcaagga gaagagtgtt gcagttctca atcaaaacca aagttttctg aaagacagga 10620
aacagcagtc ctgctatgga cagagcagac tgaaaataga atccagttgg tcaccatact 10680
agaatggtca ccagttttat gccaccatac cgaagagttt tacgtacatg gctatttcct 10740
gctccctttc caatctctct gcactggagg aagctttgcc ctgatcccca tttgccgttt 10800
ctctatcctg cccttgggta ggatatgaag ggatgttcct gctttacaaa gcgaggataa 10860
atgatggttt tccctgttgg ggctcaggta ctgcttcact tcacttcatg ctttggtgtg 10920
catagcttag agctgtggct gacatcgagt gcagtgctgt gctggctgca ggctgcaagc 10980
attacccctc atgcactccc tcctgctttg cttcatcttt ctccttgtgc tctcaccaac 11040
ttcctcttct ggccttttgc aaagaggata acaccaagaa gacactgcat gggcagcagc 11100
gtgaaagggg gagggagaat tgctgctctt gtgcatgggt gggcactgac ccgcaaagat 11160
agcggggcag gcaaagggct ctgcaggctg ctgagcaagg ccacaaacag ataggcatgg 11220
ggtgcagctg ctggggttgg ggtggagcct ttcacttcac ttttttcttc ttttgttttt 11280
ttaaactttt tggcgggagc tctgtgtgcc tatgaaacag atgtctgaaa ctactgagtg 11340
tgtatgcact tgaaacggtc tcactgtagg accccgatag ttacatactg ttacagtaag 11400
aagatatgca tatatgcctt taaaactact ttcctgctgt ctgtatttta aagaaagtgg 11460 ggtttttttgt ttgtttgttt taattttttg gtggaatgga cgtatggggg atctggagca 11520
tttgacttgt tttttagttt cttctagcca gcctaaaatt cttctggaag agctttatgt 11580
agtcattccc tatcattctt ctaggaaaat tgtggagtct tggaaaacgt atttcctgtc 11640
taactctgat cctcctactc aatgaatcac ttgtactctt gtgttgcttt gggccgactt 11700
ccctattgac ttcagtgcct gggatttaat tagaaatcta gggatgttat ttggagctat 11760
aaaactacat agcattcttc tctgtgcagc aggactacag taattaaata tatatatata 11820
tatatatttg catattaact gtccttggtg tgaactgaat agttgcttca catttccatg 11880
tgcacccttt ttgcaaacta ccctttaaac caccctccta gtaaacagca gcaccccatc 11940
cttttacaaa cctctgaaca aaccccagag ctggaggcct ctctggctgc ctggtgcagg 12000
agggctctgt agggcacgca gagaggtgtg ctgttctgct gttccaggca tttgtatgtg 12060
gggacaaaat aacccccaga aattcttcat tggtgtgaaa atgtctgaat attctcccag 12120
tgggtgggac cttcctgtgg agacacagtc acagagagcc cagaaaagcc catttcatgt 12180
ttgctgctaa tggtcttgag tcctgtaagg ctgccctggc actagggtga aaagccttgt 12240
tcagggtggg gcacgttcag cttctctttt gcatgaatgc tgctgttcag tgtccattgg 12300
agatagcacc tgcaaaaaga gtggagatca gtttttcaga caaaagcaaa tacaacaacc 12360
ctttaccagg cagtcctgca ctgctcagga ctgtgggaca ttatctccac ccctcccatt 12420
gagctgctcg ctgcatcagg gtaggggaga taagagacaa agaggctgca gcagcagcaa 12480

-continued

```
tgctcgccaa acctcccctt ccagcatcac ctgcagcaca ccttgcagtt ccccaggatt  12540
taggtgccac tgtgaagcag atcttccccc agagcagccc gagggagaat ggatgagggt  12600
gggctctgac tgcatgggtt aggattgccg gagcccgcct ttaggtttcc agaacagaca  12660
ctgatctctc catgcttctt caataaccct tacgtgtaga aagaagctgt cttaataaac  12720
gatgacacat cattgtagca cactgtatgc agtgtcagtg tggtaggttc atttaaaaat  12780
gttcattttt ttatgatgat tattgcttac acttgccaaa aatagttcta acaaccaaat  12840
ctttcaagcc aggattaatg tttttgaatt ggttatgctt tttacagaac aatacaaagg  12900
tgaacagttg aagcaaagct gaatatctgt gtttttgaaa cactgcttaa ctggcatgct  12960
agcaaaattg gggatcaggc acagaaaata accttttgca tacttgccag cccgatggaa  13020
taactttcat tttttgcctg agctgtgttg tcctttgctt gtgagtgaac cctttatcct  13080
ccgtgcagaa ctgcttatgt gcattttgca ttgctctttt tccaggttaa ggaacttgtt  13140
cttgacaact gtaggtcata cgaaggcaaa attgaaggcc ttacagatga gtttgaagag  13200
ctggaattct tgagtacaat caacgtaggc ttagcctcag ttgcaaactt accaaagtta  13260
aacaaactta agaaggtaaa tatatccttt ctcttcctct ttgtaatatg ctgaatgtaa  13320
aatggttgtt tgcataaaaa tgtgatttat gactgaccga gctgctttgt gatgcatgtt  13380
tgcactagaa actcaaggtg tttttgtgcc ttttagctcg aactaagtga caacagagtc  13440
tcaggaggac tggaagtgtt ggcagaaaag tgtccaaacc tcacgcatct aaatctaagt  13500
ggcaacaaaa taaaagatct tggtacaata gaacctctgg taagttggtg gatagagcaa  13560
aataaaaact aattttgtga agagaagggg caaagcgctg gcttggcaga gacaacgctc  13620
tgggttttga cattctgaat ccactttcaa ttgaatgtct tcagccccgg tgcttatctt  13680
tacagcctgg tggcccttgc tatcgggctg acacctacag tgctccgccg gtgccgggcg  13740
tccccgcggg gagtgtgagc cgctgctccc ccctagcggc cagcgttccg cccggagcag  13800
cccggggcct gtccctgctc tgggcagtgt gggacagccc cacgccgggg atggtgtcac  13860
ctttggggtg cctcgtgaag cagagcagtg ctgcaccgtg gtgactcgag aggaagggag  13920
caaaagtcag ttctttgaga tgaatttcca gctctttcct gctggtttcc atcactgtct  13980
cttgctcact gctgatacat actccttatt tcagtgctga gttcaggttt atcaggttac  14040
tgttccaaaa accattcaac tattggttct aatagcgttt tttaaaccaa aaattaggaa  14100
atagtactgc gtgcccttta ttgtccagaa atgaaggctt tcaactcatg cccacttccc  14160
agatatttgt tcctaaatgt ctcgaagagc atttttcaag tgaatccttg gctctccttc  14220
cctccagcgg aaggggaaag cagaacagta aactcgtata gcaaacagat gagagaaagg  14280
attataagta tttccagttt cagacttgtt ttcttgatgt caccattgct gtacatgctg  14340
aactctggaa gagagatatt tcataagtct tgatacaaat ctttaactgc tctgcttgca  14400
cttttatagt tttactttga agtgctgctg gcaatgcaga cctcttatcc aaaacaaaac  14460
aaaaaaatcc cttttgggtt tctaagtcct tttttcattc ttccaaagtc aaatgtacaa  14520
tcatcaaaat ttttaaaatc tcttctagta aagttctggt gtctgaagtt tccttttcca  14580
ttgtaaaagg tagtccttct aggatagctc cctggtctgc tagttattct taacttggtc  14640
cctcacagct catgtgattt ttgtaccatt accttttttgc aaatcccagt cttccacttg  14700
caaggtgttt gacttaagaa aaagtatttt ccactcacag atactgcagc agcactgccc  14760
agacattaca gatttctgtt ctgccccaat ttggtaggca gaggctgaaa tgactccttt  14820
tgtcacgaga agctcttgaa cacattaacc agcctttgct aaactgtctg tcctgtagag  14880
```

```
gtttattgca acactgaact tcagagactt ttctttcctt gcagaaaaag ttagaaaacc  14940
tgaagagttt agatcttttc aattgcgagg taaccaactt gaatgattat agagaaaacg  15000
tattcaagct cctcccacaa ctcacatacc tcgatggcta cgatcgggat gacaaagaag  15060
caccagactc tgatgcagag ggctacgtgg agggcttaga cgatgaggag gaagatgaag  15120
atggtatgtg aattgtgcta cttagtgtgt gtaagttaaa agagcaatat gctgcctagt  15180
acatattgct tccagctctg acttgttggc aagagaaggg tgttctcagc agcttcttcc  15240
tgactgatgt aaaggagaag tacctcagtg tcctctgaag gaaggagggg aaaggaggtg  15300
gtcagggcct gaaagaacaa ctttctcagt cttatctcta gtgaaagatc gggatgacaa  15360
agaagcaccg gactctgatg cagagggcta cgtggaaggc ttagacgacg aggaggaaga  15420
tgaagacggt atgtgaattg tgctgcttgg tgtatataag ttggaagatt tatatgctgt  15480
gtggtatgtt ttgcttccag ctctgactta ttgctaagag aagggtgttc tcagcacctc  15540
ctagctgact gatgtaaagg agaagtactt cagtcctttg aaggagcgag gggaatggag  15600
atgggcaggg cctgaaagag ccttattctc aagcttattt cgtctgaaag atggggagtg  15660
aaaggatata gatgtaagag actggaagga ggaagacaag cattaaggac accggaacag  15720
ttaagggaac agttaacatc aggggatgag tatgtaaagg agaaacgtaa gaaaagatga  15780
gatgcacatc ctgcagtttt ccaggatcca tacaatcagg gaagtatgtg tggttgcgta  15840
gaccctggca gaggagggca gagcaggaaa cgtgagtgga cctagaaaag agtagctgag  15900
tcaagggatc aagtggagaa gctaaggcat tgctgggagg ttatagcttg tctttgagga  15960
caaactgaac tgattgggat caggcaaaag agaggagaat gtatgtattg aagcttgcct  16020
gggacaagct ctgtgaaaga cactaatgaa gcagcaagca actttttaat gataggaaaa  16080
tgaactgtgg gttccactgt gctgtaggtg ccattctgcc tccctggcag actgcactca  16140
gaggcatcag tgtgttggtt ggatgagtat caggctgact ttggggaatt tgctagactc  16200
ttcaaaccca gctgcacagc aaaagcagaa tagctggact tgcacttttc ccttgagtgc  16260
tgaatgtgag ccctggtgaa aggggtgaga gctgcagcaa tgccaggcag actggtgcat  16320
tcatccagca gcacaaaggt tcagcaagga caggttctct tcatcagagt acaagtctga  16380
gcctgtgttg aaatgcatga aaaagctccc aaaataccat tcctgcagca tgagaaacat  16440
tcctggcttg ttacttgggc tggttgcatt taagtccttt cctcttgaaa acaaattgca  16500
aatttgtatg gtggattgtg accccttttg tatggctgtt acagtatgaa ggcaaagtac  16560
ttcccctagg gagagttcct acttcatggt tggcttgtaa aaagttctac cccattcctg  16620
ttggaaaaag atggacactt gcagttgaaa agctgcaaag tgttccacaa gctttaaaac  16680
acatttcagt tctgggaact ggagcagctg aagcagtctt gaggctgctg tgacttgctg  16740
tcaaaggtcc tgcagccctc gagcagctcc atccatggag gcagctgcca tactacccag  16800
ttgtttggct aaagaggaac agaactgtgc ctatccctgt ccagcagcag gaaagctgtt  16860
tttgattccg tgttgcattt aagcaatgct ttgtttgctc cttgtgtcaa ttagaggtcc  16920
tgtgtctcat catggtgttg aaaaataaat ttaagtatct gagtaattaa tcttgtttaa  16980
ctgtatatag aagaggagta tgacgatgat gctcaggtag tagaagatga agaggatgag  17040
gaggaggaag aggaaggaga agaggaggac gtaagcggag aggaagaggt aaggatttat  17100
gcagttaata attggcatga agtgaacatt ccataactgg gaatagctgg gcaagaaatg  17160
gacagaagat tgcaggcttt ttccgtatag catttgcgtg ctttctgttt tcacctgaga  17220
```

-continued

```
agcatcacag tgggggtgtc tttgaggact gcctgtctgt gagccagctg ccatctagtg  17280
accactgaca tgaaatcatt ctggttttgc tgatgtcaaa agtactatca gaaatgtctg  17340
atggggcttc tgaagggatg agtttacaga caggagtggg gcatgagtta ctgaccctat  17400
ggtcttagtc caaggttctt ttctatatgc gtgtcttgtg attcttcagg ttgcttgaat  17460
tcttagtgta gtcctgctgc tgtgtgtagg gcgtaacaag ctggtcgcat tttgctgaga  17520
cttcactgtt aacagaacca ctgggaatgg ggctgaaatt tgtctgtggg aggccagcta  17580
ctcagaatct gtaggtgtct gtccatgttg taactttcct tacccatcaa acatgtgcct  17640
tctcctgttg agccatcata agtagcagtc atcaagtttt tctaaactca gggcatcata  17700
acaaaatttg cagctactta tcatctgaag tatgaaacca cttacttgct gaagagttga  17760
agctagaagt ggtgctatga ttttctgcaa tgaaacttgg gccggagtcc agttatgctg  17820
cagcaaaaaa cttccaacaa ctgcacttat ataagtgtgt gggaagtgtc tgccttttgt  17880
ttggtttcta agatgcttca aggactttct gtttggatat tgccaaattg tgaaaggttt  17940
tgagctgaaa ccaactttct cacctatttc tgatgttgtt tttctttctc tgcatccagg  18000
aggatgagga aggctataat gatggtgacg tagatgatga tgaagatgaa gaagaacccg  18060
gtatgatggc agtaatctac tttttccttg agatttttat atatatatat atatatatat  18120
atatatatat atatatatat atatgtataa actttctaaa aagcaggctc atgttttcat  18180
tcctgctcct ttggccactt gccagtagag tagaacttac tgaactcatc cagcatctca  18240
gccacttgtg gaagctctca tttcactaaa gttgtgtttt attttttaga tgaagaacgg  18300
ggacagaaga ggaaacgaga acccgaagac gaaggagatg aagatgacta aactgaataa  18360
cctattttga aaatttccta ttgtgatttg actgttttta ccctgtattt cccctcccca  18420
cacccccaac cttttttttt cttttttttt ttttcctgat tgtaatgttg ctgtgggaat  18480
gagagggaga agcagactgg gtgggcaagg gaataaaata ctatttttac tgccactcct  18540
cctcctattc atttaatata ttttattttc tttttgtccc tctcttagtc cctgtaactg  18600
caatagtaag tataaaccaa gtggtaattt gtttcttatt attggagtgg atagttgaca  18660
tccctaaaga aaaaaagttt taagatcagt ggatgatacc ccaaatacac atgctttgtt  18720
ctgagacagc tgaatatccc tggttgttgg agttttccac ctctgccagt cacaaaatac  18780
attgtaagca tttttggggg gtgctccaaa tctaggcaaa gcatccctct gcagcaacag  18840
gtgtgagaat ggcatattga taaagtgatt tctttgttgc ctgtccgtga atgactgcca  18900
ttttcagcca ttgctttccc tgcttttgta ggtacctttt cttttgctgt ttgtaaatag  18960
tgaccaaatg tttctggggg gtttttttggg gtgttccttt ggatctggtt tgtggggtga  19020
atttgcagtc cccttcctcg ccctgtgtgt tgtgttcttt ttttcctttc tgtttttttgg  19080
ttgggttgtt tttttttttt ttttggtttg tttttggcta gggtacagcc aatacactga  19140
aaatggcagg catttaaata tatatatata aatatatata aaaagtgttc ctaattcctg  19200
agttactagt gaaatgactt tgacaattgt aataaaaaaa atgtttcaac ccttttaaa   19259
```

<210> SEQ ID NO 2
<211> LENGTH: 42361
<212> TYPE: DNA
<213> ORGANISM: Artificial Sequence
<220> FEATURE:
<223> OTHER INFORMATION: hANP32A

<400> SEQUENCE: 2

```
agtgtgcgcc gcgggtgctg ggggctcgag aaccgagcgg agctggttga gccttcaaag     60
```

-continued

```
tcctaaaacg cgcggccgtg ggttcggggt ttattgattg aattccgccg gcgcgggagc    120
ctctgcagag agagagcgcg agagatggag atgggcagac ggattcattt agagctgcgg    180
aacaggacgc cctctgatgt gagcatttgc caaaaatatc tctgtcggtc cattctccta    240
ctttgtgtgt gtgtgtgtgt gtgcgcgctg gggggaggca ctttttttgg ggggggggcgc    300
ccgggaggtg cgggtttggg ggtcggactg caagcgaatt ggcaaggctg gggggttgca    360
atgccatccg agcatgttcc ggctgccgcc gccgctgccc ttggtgtgtg actacctgtg    420
cgtgtgctcc cgcgtgtgcg agtgtgggtg cgagagtgtg cgtgcgagtg tgcacccatc    480
gggggccggc gggcgcacgc gtttgggtcg gagagaatga ggcgaaatca ccctcggaga    540
tcgctgctcc cgtgactccg tctgggggga agattaacga gggaggagga ggagaggggc    600
tgcctcctgg atttaacaac aaaaaaaggg ggttttacat tttataaatg tatcccccct    660
tccgcccccc tcccgcgcct ccccccctccc tttctctcgc tcgctcgctc gcacacacaa    720
taagtttggg gcttcgcgag tccggtttag tttctgataa atgtgggccg aggcccccgg    780
ggagagcgcg tggggagggg gctgcagcgg agttgggaat ggctggagtt taaagtgcgt    840
cttcatttct ttgcagtgat gaggcgagag acgggggagc catatttgta actttgtagt    900
gttcgtgaac gcgccctttc tctccctccc tccctttctc tgcctccctt cctctcctcc    960
tctttctccc tcactctttc caccccacct tcgggccaga tgctgatgtt tcttcctttc   1020
cttccgaagg gaggataaat tagaaggagg gggagggatt ttcgaacgtg ctaaggcaca   1080
gataatcccc gcgtctccct gcctccagcg atcgctggtg caagttgccc aaaggctacg   1140
tcccggtgcc ccctcgcccc agctccttcc ggcttcccca agatgccagc ctttgggccc   1200
tggtgccccc cagctcgaac ccccggcccg tctttctcag tgctgggctt gtcggcagcc   1260
attcggcgcc tgcttaataa atgggcacgg gaaactttgt caggacgcga gctgcccgga   1320
gctggcgccc gtggtgggta ctggctgggt ccacgtttat gcgggcatgg caaacacgca   1380
gctctaggat gggagtttgc ccgctagccg ccgttattga ttgggcagcg gcgggagcac   1440
ggccggagga aacttacacg ggtgggaatc gcgaggctcg agcgaaagct tacccctgag   1500
gagggggaag gtgagggtgg gtgactcgaa cgctggtttt tatttctgcc tccctctcgc   1560
tttcaaacct gagtgttttc ggcgagttgg cggctctggg gcggagaccc tggccagctc   1620
ccctcttggc cccttggggg gaccggggac gcgctggcgg gaggacgccc ccagtctcgg   1680
tggcccgagc tccatggagt tgggagtttg ggcagcaccg tgcgctggcc tgtcgcccct   1740
ctagcccgtt aaacccgaat cccggcgaag gcaggcctcg cttcctcttt tccctagttc   1800
ctcccccaaa cctgagtgag acttttgaaa acaagatcct ttttgtctac cccctccccg   1860
ccttaacgca gctgtggact ggagacgtgc gagtgcctta tggcgcgcag ggcggggagg   1920
gggcggccgc gggagaggag ggggcgccgc cggtggaggc cggagtttcc gcgcactatt   1980
tgcgggcggt ttgcctctct ccggccgctt tcgtcccggc cgggacccgg cgcctagcgt   2040
ttgggggctg ggtgtggtga tgggggaggg ggccggggcc gcggtcttcc cgcgtacttt   2100
ccggaagccc cctgcgcgga gggggaaggg cgccaagcgc ggggccgggg tcgccgcggg   2160
tgggtgcggg ggcgcggctg gcctggcgaa cccgaccgac gctgccggcc ccccgggagc   2220
aagcaggaaa gcgggtcgaa ccggctcttt aaacttccac gagtgtgtgt gtgtgttggg   2280
gaggggagcg caccgcgccg tactgggagc gatttctcac gcttcgcccc ctcgcctccc   2340
agcctcgcgg cccacacgcc tgccccctgc ctggaggcgg ggtggggcgc gggtggcgga   2400
```

ggagggggca ctttctgcac atttgcgggg gagggggaga aagctagcga aagagggaca 2460
aaagggttgg gggaggagga actgtatttt tttaaacgtt cttaagacaa atggctcccg 2520
gagcgcgccc cctgcgcccc tccccgccgc gctgcccctg ggccccccac acacccacct 2580
tcggcacctc tcccaactgg gctccgggag ctggtggcca tgccgcgacg ccgaaatagg 2640
acgagcagcc atgtttcccg gggctcgcgc cgcacgcccc gcccctcctc cccggcgcgg 2700
ggcgcagggc tcggaatgcg ggctccgggc tccatgtggc gcggggcgct ggcaggcggg 2760
cggcgggggt gcagtacgcg cggggccggc cttgtggctt tctaggctgg ttttgagttc 2820
caggtgtttt atttatttat ttttatttat ttattttttt taacggctag gcccactcgg 2880
ggctgagccc gaagggcgcc gaggcgttac tgggggggcag gagccgcctc cagggccctg 2940
cgcgcctgtg gcacgactgc cgggcgccgg gctgccattt tgtcaccgtg gctgttgtcg 3000
ctgtgggggg cggggggagc ggagtcttgc gccatcaccc cgacggcctc ccgcgcggag 3060
gaggcagggg gagccggctt tggggacccc cagttgtgct atgagccccg atgggggttt 3120
ccgccccgcg ccaacggcct gaggctgtgc tggagagtca cggcggccgc ggcgccggga 3180
ggacgacgat cctctgtgca aatgcccccc cccacgcgct ccctgcctcc cccgcctcct 3240
ctccggggtt tcgccgttcc tcctgcaggc gctcagacgt agttaaatgt ggccttaagg 3300
actaaccgat cgctctggtg tttgctcttt cggcggaagt gatagagtaa ggggaacatt 3360
aaacatgagg ttcttttggc gggggtgagg ggtgtcgcgc acgcgactct agtggccctg 3420
actgaagcca aggacagcag cctgttcccc gggagggaag agttgtcgat ccgttgggga 3480
aacgccctcc cgggctgggc tctccgggaa ggtaggtcga gctccgtgtt tcaggtggat 3540
gttgcagcgc cctgcaggct aggggaaccc tcctcctcgg tctaaacctg ctccttcccc 3600
cttttatttt tgcctgggag aaggcagcta caatagtaat gagatcctaa agcgaaagag 3660
agggatgaag gtttgctttt gaaaaaagta aaccgccttt ctccggatgt tgacttagga 3720
gccaggcaat tcgtcgcgtc gggtcctccg atgctggcat ctctgagaat tttaaaaagc 3780
cgatataggt gctggttaag cacctcacga gctgaactct ggtatctgtg cagaaactaa 3840
ctttcatggc agtgtccagc agaggctgcc ttggaagcca gcttttactt tgacctttgg 3900
aatacatcgc atgatgtttt ccaggctgac ttactgccta attgggttca agtagcatga 3960
tattaactac agtttatgca agccaaccag gaactcgcag gcagaaaatt gagcctgagt 4020
tcccctgtgg tcatagtcag ttgagttctg ctgctgatag tagtttcgag tctgaggggc 4080
tccatgatga agatgggctt aggaattaca cagacctggg tttgaattcc tcctgccaca 4140
aggaggtagg atacgtttac ctgcccttgt gaccttgggc tggtgagctt aacctacctt 4200
tttgaagctt tgtttcttca cctgtaaaac ggaataatcc tatttaatca gtaaatgatg 4260
acaaaattgg tttgatatgg ccctcagtat atgctgtcta tatgacagtt ttagtctcgg 4320
agacatatca gggtgcttcc aggcattact ttgagctcct ccatggttta ggataataac 4380
aatattagct agtgcttaca tagcaaccac gctgtgtctg gcacatttct taagtggatt 4440
acatgtatca actaatttag tccccacaac agcactatga ggtaggtatt attattatca 4500
tcgtcattgt gcatatggaa attgaggcat acaggggtta tcatgtgacc agtgagtggc 4560
agaaccagga ttcaaactca gccagtctgc atactcaacc tctacactct actgcctcct 4620
ttgaaacacc cttttttttct taagatactg taaggaagag ctttttcttc tccagctttg 4680
gagtggtgcc accgtagaaa gagaatgagt tttctattat tgaagacgct gaaatgaaga 4740
gtggatagca tcctggttgg agatattaga gggccaggag gttcaggacc aggggctgtg 4800

-continued

```
gattatcatt ttatgaagcc ttgcactgag tttgctttag cacatcacag tgggttaggt   4860
tgaagtggat ctggccttca aggtgctggg ggacacattt tgagtaagga gaagacaagc   4920
aggagctgct caggcagtct gcatctgcag ccaaaaaaac tcaacataac tggcatgtct   4980
ttagtatctg ggacatagta tgctcatagc acctcatgga tcatctcact taatcatccc   5040
agcaactctt taagggtagg ccaagcagtg caatgccacc cctgttgtga ggatgaatca   5100
tctgattttt ggagaggttg agcaactggt aggtggcaca gccgggttct cgcactgcaa   5160
aaccacaggc ccctttggtg gacagagatt ccgaggattg gatagtccat tgggtccatg   5220
gcccattacc agaatcacgt gagaggcatg taaaatgcag attcctgggc tccaccccaa   5280
tcacaggagt accacagcaa tcaccaaact ataactgagc tcccaatttt tgtacagtca   5340
tgagctaaga attatttgta catataaacg ttgcagtcaa tttgatggta tggaacactc   5400
tttgaatccc aatgacttga aatgttattc tcccaaaaaa taagaaatcc acttgtctcg   5460
ttaacagatc tcgttacaaa aaaaaaattg tactcaatat attctgaact ttatcaataa   5520
aagaattgtg gaaatgtgtt agatttttct cttgttataa aagtccctat gtagtgttct   5580
taattttggc tcttgataaa gtttactatc tgccccettt gcagaagagg tttgctgaaa   5640
aggtggttca gtagattgga gggtgggccc cagggatcta gtgttttgct ttgtttaagc   5700
aaatggcaag ccatatattt gggtggtact ctcagggtct ttttaagtcc ttttatgtgt   5760
tctgtgccct gtaagtaatt ggtgcctagt ggaaatcagc ctcaacccag gaacctccat   5820
aggaagagaa attatccttg ttactggttt agtatgaagc acttctcgtc tagagttctg   5880
tatagccagc tgaaattctt cgttgtgtac tcagaacatg tcaaagcctt ctgtgtatct   5940
tgtagttgaa tggtcactct taggttctag atgtcatctc agagatagaa agagctttgg   6000
gttgcaacgg ttagagcttt gaggcttgaa ccaaaggcgg ggcagctgtg cacccagtgg   6060
ctcacatcag cctttcagag cccagatctt tgaaaatgac agataatcct ggaatctcta   6120
gtttttggcc tgctgctttt ctaccatgcg tgtttcctgg ggaatgaacc agcagcatag   6180
tggctttgag tttcagaagt tttccctct agcgtcttgt gcctgagcta atgaacggaa   6240
ggaatggtta taaaattggc caggtcaagg ggaggaggag ataaattcaa ggggacaaat   6300
cctagtcccc ataacagcag cctgtgttat gacagcacac cacagcccca attccctctt   6360
tcctgctgct gctgcaccac cagcctctca aggtggctta ctctagactt acacagttgg   6420
ccatctttct tttttttttt ctttccccat agcagtatga gacttgtttc ctttttttatt   6480
tatttatttt ataattttttg tagagacggg gttttgccgt gttgcccagg ctggtctcaa   6540
actcctggac tcaagtgatc tgcccacctt ggcatcccaa agcgctggga ttacaggtgt   6600
gagccagcgt gcctggcccc cttcttcaat accattggaa agacatctgc ttgagctttc   6660
agagctgtcc atcccagagc ttgggtccaa attaattaca tcacattgaa ataaaaaact   6720
tcctggaggc tgggtgcagt ggctcacgcc tgtaatccca gcactttggg aggccgaggc   6780
gggtggatca cgaggtcagg agatcaagac catcctggct aacacggtga aaccccgtct   6840
ctagtaaaaa tacaaaaaat tagccgggca tggtggcggg tgcctgtggt cccagctatt   6900
cgggaggctg aggcaggaga atgccgtgaa cccgggaggc agaacttgca gtgagcagag   6960
atcgtgccac tgcactccgg cctgggggac aaagcgagac tccgtctcaa aaaaaaaaaa   7020
aaaaaaactt cctggaaatt gtgtaggata ctctttagac atctcatgcc tttgctattt   7080
tggtgcagtc acttaggaaa ggagccggga gcttgttggt gattgggccc tggcccaatg   7140
```

-continued

```
aacgtggccc aattgtctgg cctgaattct aacttagttt aagaggaggc tcatagctct   7200
ggtgtctaga gaggcattcc tttagaaatg tttgccacca gcatccctcc tctttgtttt   7260
ggcagtccat cccttactct agctagttct ctggtctcct aggaactacc ctctcccagt   7320
cccccagcac cactgccttc aagtagagaa acatggacct gactctgaat cttctatagc   7380
tttgaaatag aattatacaa caaatgataa atacccaaca atgatgtttt cattaaagag   7440
atggagtctg gcagggacag agatttgtga aggcatctgt tattcagaac ttctcattta   7500
ataaaatttg ttgaaactag atgagcaaag caccatggcc ctgagccacc ttctcagaca   7560
tggaagcagc ctccttgtct agaactagtt gtcctgatga tatacagact ctaaggaaga   7620
taaaagtccc tttattctac cacaccaagc cctgtcctgg gcctgctggg ccacaccctg   7680
caacccagtg ctttccctca gatttatttt gttttagctc cacagctgcc ccctgaattc   7740
attcagctac tgtttccttt accaaaactt gctccaggca gcagatctaa aagatcagct   7800
tacttactac tccactgtta tttactctaa tgtggattaa agtcagcact gtttttccca   7860
gaggtattta catttggaga ttctggtttg gtgaggaaat taccagagaa ctattaaaga   7920
cttggatgct cttctcggct ttgctattaa gtaagttgga caagttgttt ggcttctttg   7980
agcctctgtt ttctccattc tgaaattcta aaatgggagt gttgaattag atcagtggct   8040
ttcgaacttt ctgctcctag tagtgagaaa tacattttac tccactccct ggtatgtaca   8100
cgcattcctg tgttttgtga aaaaccgaca ccatgctcct ccctcactac atgtaaaaca   8160
cttttattca ttaaaaagaa aactgactgg cttggaccta caaattagtt tcattatttg   8220
ttaatgtttg aaagccatta aaagatgaat attaaggttt ctttatactc aatacttgta   8280
gttttgtttg ggggaatgag aggatgccct tggtaccttt gtgaggcctc tccactgagg   8340
gtcaatcatg acttctgttt taaaccagcc catcccatct tctccagctg ctctccttat   8400
gtcttgcttc tctcccctcc aaccttctca gcataaggac tcaatcctag gctcctaccc   8460
cagacgggtg ccttccaacg ttcctggtgc cagtggcccc ccatcagcca tgttccccca   8520
gccccttctc cacactcttg tcacccaggg ccccatcctt cagtgcattg cacactttgc   8580
atgctgggtc agggaagatt gtggagagag gacagtgcac ctggtttccc ccacatagac   8640
tgcgtggggg tatgtcctgc ttccgccact tccaactgtg gcacttgggc acgcccctct   8700
cagggcacct tccctttttg tctccgcaaa atgaggttgt aatagtgcct gccgcactgt   8760
ctggcacaca gtaagctctc aagaaatgtt agctgttgtt gccgttagaa caccatagct   8820
agaataccat acctggcatt cacttaaaaa aaaaaaaaac aacttagggc caggcgcagt   8880
ggctcacgcc tgtacttcca gcactttggg aggccaagac aggcagagca cctgaggcca   8940
ggagttcaag aacaggctgg ccttgtctct actaaaaata caaaaaaaaa aatcagccgg   9000
gtgtcgtggc aggtgcctgt aattccagct actctggagg ctgaggcagg agaatcgctt   9060
gaacctggga gacggaggtt gcagtgtgag ccgatatcgt gccactgcat tccagcctgg   9120
gcaacgagcg aaactcggtc tcaaaaaaac ccaacttaca ttatccgcag acacattaca   9180
tacaaaagta accattttct ttcaatggga aaggaggttt agaagctaga gattcaaagt   9240
taccaggagt tactttttcc cactaggaat tcactacagt cctgacattg gactctaggt   9300
agtttctact gagggtaagt gactcgtccc tcttctgggc aactcttttt cttactgccc   9360
tcagcagcta tttcaggcct ccacccccttc cctcccggcc aggacgtcct cttcacagaa   9420
aatggaaacc tcctggtttc ttaagtagtt gtgaggctga acctgcctta atccctccca   9480
gttcagtggt cttcttgtct tgtccatccc tccctcagtt cccttgttcc tcctgggcac   9540
```

```
ctagccactc ctgtcctttg gattcttctc cagctgggga tgcttctccc atcttaaagc    9600
aaagactcta attgatcccg tgttgcgctg tagttactgc ccatccccact cttctcccta   9660
ctccctaaac tttctgaatt gtctatcttc tccatcctgt cacctctctt actccaccac    9720
gtgaagtctg gtttgcttcc taaatagtgc caagaatccc aacagccttc atttcttatc    9780
ttgcatgatg tctcagtggc gggattcagc attctttttt tttttttttt ttcccagaca    9840
gagtctcact ctgtggccca tgttggagtg cgcagtggct tgatctcagc tcactgcaac    9900
ctcgacctcc tgggttcaag cgattctcgt gcctcagcct cccgagtagc tgggattaca    9960
ggtgtccacc accacgcccg gataactttt ttatttttag tagagaaggg gtttcaccat   10020
gttggctagg ctgatctcga actcctgacc tcaagtgatc tgcctgcctc ggcctcccaa   10080
agtgctggga ttacaggcgt gagccactgc gcccggctgg gattcagcat tcttgacttt   10140
atgatagatg ctctcccttt ctctggtata tcttctacgg ctctagtcac tgctcagttt   10200
ctggtgtcct gttgctctcc tgtttagcca tgaagtattg acttagtcaa acttgggcgc   10260
tgggcattct tatcctgtat tctctccagt tggaaatttg tccttcctca ctgacagctg   10320
caggtactgc gtgctgctct ctgaggtttg aagtttactg cttgagtaag cttgagaccc   10380
acctgatgtc tccacctggg tgctccaaaa gtgccctact cttaagtcca aagggaaccc   10440
atgtcctctg tcccttgccc accactgccc acacacacac actcatgatc ctctttccat   10500
ccatcatcat cacaagtctt gtctgtttaa aacatgctct gttgcttgcc actgatctcc   10560
ctgtatcata gtctagtctt cttgaagcca tgctgtgacc ttcaactaga atgatcttat   10620
caaaacacac atgtaatgtc accccatact taaaattcac cattgttcct aggataaagt   10680
cccaaatctt taataagacc aacaaggtgc tgcatggtct ggccacttcc cgtcatctgt   10740
tcccttgccc cactctctct gggcctccct ggctgcctct cattcctgca aacctgtgcc   10800
acactgagat tgccactgta tccagttagc atctagtcat ctttaccatc tccagcctcc   10860
tccgtcaggt ttagatctag ttcttttgcc agaaaactct tacagaactt ttccctcaga   10920
gtgcttcagt ttgtaactac atattccaga ttatgagtgt ttaattagca tctctgtccc   10980
cttgcctaat gggtgcactg cacgatttga gggacttgct tttgctcatc attgtggtct   11040
tcagagctcc acactgtgcc tggcacatgg taagcattct agaagtactg atggagtgaa   11100
ggatctgtgg tacttatacc ttcttgtcac tttcatcacc taccggttgg tacatcaagc   11160
acgaagccac tgaaacgaag cgcacacctt cacacccgca cccccacgcc cgctggtgtg   11220
actttctgat ggagttgctc tgggtgggtg atgcacactt cttaggtcgc tggtcatcat   11280
gtttttctca ttatcacatc ccttatcagt aaacaatttg aacctgagcc ccagtatgtc   11340
taccttgcag ttatggatta ttcacataca ctacctataa atatggacat tataaaatgt   11400
aacgccaaaa atataaatta aaaaggatac atttaaacat ctaaaaagtc ctgaaattct   11460
tgcatcccag tggattggct tgggcagtcc acataagaga ctactgttct aattaattgc   11520
tcgttttatt ttaaattcag ttactaaagt tcactctgta aaagaaacgc tcataccttc   11580
ctagacactg cttgttaaga tctctccagc tctagtgtgt gatgagtagg ggtaggggac   11640
attcacagtc tccctttaat acaataagct agcttgcccg agatccttgg tgaatcaagg   11700
ctccactgcc gtgtgtcagc ttggtgctct ttgtttaggc tgtgtggaca gatccaccaa   11760
agtcccctcc agtcacccct ggggtcccac agaggtaaac ccccgggttc tctctgccca   11820
tgtcctgaga ggccaggaag tagctacgat aaggattcca tcagccatag actcagggtg   11880
```

-continued

```
ggtgggaagg tggctttctc ctagttatct tggagtgggg aacaagtaag aggcaggatg  11940
tgtgggctgg aagggcagag acagaggtgc acagtgaagc ttgaaagaga gaggcccgca  12000
gagtgtgttt gctgagagat ttcagcaaag ttgtgctgga actctgcagc cagcagtgcc  12060
cagtgctggg tttctggatt ctgctgcctc ctgtagaatt cgtgagaact acgtgtgtat  12120
gcatgtgcgt gtgcaggggg tgatagggtg gaggcaaggg cctgtcattc tcaatttaga  12180
ggaattactt tcagatttct tcagggacca tgcatctgga ggagggactc atcttcaatt  12240
tatgtaacca actgtcacct tagccattgg cttcatgggc aggcctaagt ggtgtaactg  12300
aatggacggg tgaggggagt ccactgatat ggcctgtgtg cccagcatcg ggaatgagac  12360
aaggagttgt ataaatgcta tgtaagtatt tttgtagcaa atttaatttc ttgaatccag  12420
tccttgcatc ctgggctggg taggagagaa gagagtggtt atagtggatg gtggtgcctg  12480
gctcctgtgg tggagctgga gtgatggagc atagcacata cactgcaggg aagaaggtgt  12540
gtggttagta aagccgattt caaccccagc tgtggatcag aactgccagg ggagcatctg  12600
aagcaatacc caggctctgc ctgaactgaa tcagtctctg agggtggtgc cccagtccgt  12660
gtatttttag aaagctctaa aggggactct aaagcacagt tgggaaccac cccatggagc  12720
agggtgcaga gcttcacagc aggtaggaag aagtaactaa gtggaaacta gaggaaaatg  12780
gagcagagaa accaggaaat aggaaagaag gatgcaggat ttaatctgct ggggttcagg  12840
gatccgctcc ttgacctgcc ccccacatcc ccaccaccat gggattgttc acacaaccac  12900
gttctgctca tcacacttgg aatttttcat ttacgtgtat ctcaggatgc tgctcctggg  12960
agtgtcaagt gggcattacc gatcaagact ggacttggcc catccttcat gtccagctct  13020
tgagaggccg tggacctttt gtaaaagggc gggggcccag gcgcagaccc aggcagtcag  13080
gtacagtggg cagtagtgct tgagaactgc tgagcctgag gatgttggca ggtcacctca  13140
ctgagcctca gttgccacat ctgtgaaacg gtgaataacc tgcttcccag agcttgttgt  13200
tagcacggaa agaaatatcg tttatgccag gtatgggttg tagacggacc ctgaaggtta  13260
gattctaccc gtcagggctt gaatgagctg tttggtcagc ggtgggggtg gggtggagtc  13320
agcccctctc cagaaggtgc ttgctggggt gggagcaagt ctgagaagag ctgtctcggc  13380
ctgccccagg aggaggcctc gcctggagct gtgaagcgga ggggaggggc agggaggctc  13440
tgggcaaagg agagactccc cccccccgt tttctgtgga ggtggggcgg gaggaatacc  13500
agccaagctg caggcatccc cttgccccgg gcctcttctg gggtgggggc tgtcgcgctg  13560
gctcaccttt cccatagcag ttgctccgtg accctagcct tcttgccttt aaactcccct  13620
ctggctgcag aagtctgggc cagcctctcc cagtccttta tctttcattc atacagctcc  13680
tgagaggtcc ccttttctgg gaagccctcc tcaactcact ggaagaaagg gagcaaactg  13740
tgtccaccta ggtgacataa aggtaaaagt cctggggact tccagggcac gcagcagcgt  13800
tcgcctctca gccaagtcca atagcactca cttaggtgtg catctgtggc tttctctctg  13860
tctggtcagt gctcctttat atgtccatac cccctgccag agggcagcat tgacggtgta  13920
cagagcccag tgtgactctc ctgcagctgg ggacatagaa gagctctgtg acgatggcag  13980
atgtggttct ccagcctctt gcctggctgc cagtgggagt agcctgtctg ttctggcaca  14040
gggggctgtt ccatatggag ggtcagaaac tggccttcac agccacccag gcgttccttc  14100
cacttctgca cgtcttcctt tccccatgaa gatttgggtg taccctggtt gtggtctctg  14160
aagactgggc aggcctgtac tttgtgaagc tttcagctgt ctctggtagg cctgatgaag  14220
cctatctgca gaggttggcc tgaagccata atgagcagtt ctgttctttt tagcccttgt  14280
```

-continued

```
ctagtttatg gctctgttgc agacatgcct ttctgtgtct tggttaaaag tactggtgtg  14340
tctttgcatt taggtgtggt ctgtgagtct gggaaggctt ctagaggaga gccctccagg  14400
gttgctcttt ggggtgggag tagtgggagc ggaaatggaa cgctgactgc cctcttaaag  14460
ccagaagggt acttcattca gggcaggcag ttggcatgtg taggcactca ggagtcttcc  14520
ttcagtttca gcggccggtg ttcatcatca ggagtggcag ggttggatat gggagtgaga  14580
atgtgcctct gagattgacc agtggccata gactccagca agatgtgcat cttggtctga  14640
gaggcaccca ctgtaccaga aaccagactt gtatcgacca atggcttatt agccccagga  14700
ggcttattac tgccacaaat gtccctgatg gtgagcagca cttggccact actgtctgat  14760
gttaaccaga gttatggggg tggtttctgc aaatacacaa tactgtggag gggttatgtg  14820
gcttacccag aggtgcccag atagcaaatg aaggtgtaag attggaatcc ctgtctttct  14880
ggttgaccct tggcttggct aatcattcat tcattcattc cacacacatt gatgaatgcc  14940
gactctgtac tgggttctgt tctaggaact agacagacac atcacctatg ctgctcttgt  15000
ggggcttctg ttccgctggg ggagacagtc agtagtaagc cttcaagcaa aggcatggct  15060
gctggtgtga tgagtgccat gaagacccat aaggctgcgt taaaggagat gggtggtcca  15120
ggaaggcctc tctgaggagg tggcatttga gcactcaagt gccttacact ggacttctga  15180
ccccatgagc tggaacttag gatatctgat ctagaagtac ctctagaagt cctcttccca  15240
ataaacaagc taaggcccag tgagcttaag gtgtgaattc atgggatgat tcatgggaaa  15300
gatgaaatta aacccaagaa ggacaagtat aatagccggc cactgctctg ctcacaccag  15360
ccttgggctc cagccctctg ccttttcatc ccagaatgtg ttttattatc ttcaagactc  15420
agccctttga aagatttaga cttccaaatt gcatttatta acaataatac atttattttc  15480
tcatggctgg gtgtggggag ggggtagaaa ttttaaacac atttgtgacg gttgatcagc  15540
cctccaggta aggcaacggc tgactgcctg gagctggtgt ttttcctgcc taggcggaga  15600
caccgcccaa ttttgtacca ccagctgccg tcactgtcag agtggaattt ccattggtgt  15660
ttctgaaata gcagtgtttc ctggaggacc cccatttgta ctttctggat tccatctgga  15720
cctggtttag ggggttagat gcttttgaat gggggctgga gagaccctac tgatgcctct  15780
gaccagagat ggtgaggcag gactcacagg gcccccaggg tttattttag ggagagagaa  15840
gcccacagtt aaatcagagg tcacaaatac agcagcagac ccccacctctc ccaaggacca  15900
gactgagcta taattggcca ataatttcat ctaaaagcag gaatcctaca tcaatttgaa  15960
aggagcttct ggctgaagta agactttatt aattagcctg ttaggaaaat agtttcccag  16020
tattatgagg gctggataat ttcatgccca ctgtttttct tgaagcttct caaaggcaga  16080
cacagccgcg tgcagcggct cacgcctaca atctcagcac gttgggaggt cgaggcaggt  16140
ggatcacgag gccaggagat cgagaccatc ctggccaaca tggtgaaacc ccatctctac  16200
aaaaatacaa aaattaattg ggcgtggtgg tgggcgcctg taatcccagc tactcaggag  16260
gctgaggcag gagaatcaga ggttgcagtg aaccgagatt gtgccactac actccagcct  16320
ggccacagag cgagactcag aaaacaaggg aagacactag attttcattt ttgtactaaa  16380
tagaaaaagt aatatctttt taaaaatgtg ttttgtttgt ttttaactgt ttgttcatgc  16440
caatgtgcca ggcaccatat ttattcttta atctatacag aaatgctgct ggatgaatgg  16500
aattatgctc actctgccaa tgagggaacc aaggctcaga aaggttaagt aaccaaccta  16560
aggtcaggta gtactgagga gctgtgcttg gatacaaaac caggtcatcc aacctggaat  16620
```

```
cttagctttg acccccaacc ttctcccggc aactttgatg ataatatgga aataccttag  16680
actcttgact tgactttact ttctcttctc tgttataaaa tctgctacat ttcttttcct  16740
gggaaagcga aatagattat gccaaaagtt ctgattttta aaaatgtttt attgtgggcc  16800
gggcgcagtg gctcatgcct gtaatcccag gactttggga ggccgaggtg ggtggatcat  16860
gaagtcagga gatcaagacc atcctggcca acacagtgaa accccatgtc tactaaaaat  16920
acaaaaatta actgggcttg gtggtgcacg cctgtaatcc cagctactca ggaggctgag  16980
gcaggagaat cccttgaacc tgggaggcgg aggttgtagt gagccgagat tgtgccactg  17040
cactccagcc tggcaacaga gcaagactcc gtctcaaaaa aaaaaaaaaa aaaaaaagtt  17100
tgtgaaatag agcacataaa accaaacaat atgtgtgaga tttaatgatt tttgtcctat  17160
tttttttcta tttattattt aatactttca ggggtatcct agtaaaagcg actttccatg  17220
tgcctgcctg tgcctttctg tgccagggtc ttaagaaatg tgtgtgggtt tcctctgtgg  17280
ctctgacact ccatcaaaca ccagggcttg tgcacgcagg tgagaagcat acccaggtgc  17340
ctcagagata ttgaagaggg tctggaatgt gggagagagg caaatggctt tccaataaaa  17400
gtaggctaag acataattag gggcttaggt gctgctttaa aaaataagta gcagtgtatt  17460
ccagactcct ctaagaaaag agaattgctc attgtggaac aggcatggca atgcagtgcc  17520
tttgcctgga acaccttgct gctgccatca ctaagaccca ttctgggaca agaggaggct  17580
taccccttat tgagtatctg ccatgagctt tgtgtggtcc ttgcttgcta ggtacttggc  17640
aagcattatc ttttttacct tttaaaacac ccctgaggtg taggtaaggc cacccatttc  17700
ctgacagaga ttggcctaca aaggtcagat ggcttccggg gcacactgag cggccccttgt  17760
gtgtcggaat gttcccttct gtttgtccct tccaggctgg acactttggg agcagaagtc  17820
aaagacacct ttatcattgt accctcagca cctggtgtag tgcctgggat ttagtagttc  17880
tgaggagcgt gtattgaatg aatggaggtt aagtaactta gacattagat agtaggactc  17940
tgggctgggc acaatggctc acgtctgtaa tcccagcact ttgggaggcc aaggtgggtg  18000
gatcacctga ggtcaggagt tcgagaccag cctgaccaac atggtgaaac cccgtctcta  18060
ccaaaaatat aaaaaattag ccgggcatga tggcacatac ctgtaatccc agctacttgg  18120
gaggctgagg caggagaatc acttgaacct gggaggtgga agttgcgctg agccgagatg  18180
gcgtcactgc ccgccagcct gggcgagaag aacaaaattc cgtctcaaat aaataaataa  18240
gataatagga ctctgaggct gtatgactgc caccctgtag gtcagaaatg ggatctgatt  18300
ccagctctta tccgtaagct aggtgaatgc aaactgacat gcccaagctt attgatattg  18360
caaaattatt tattacacaa aagattggaa gcaacccaga tactcatcaa taagagactg  18420
gttaagaaaa atgatgacac actatgtagt tgcaaagaag aaacgaagag ggtttttatg  18480
tactcttaca caaactccat gaaaaaaagg caaggcaatg attagtataa tatgctaggt  18540
ttttaataaa agagagaaga aataagattc tgaatttgct tgtatgtgtg tgaacattct  18600
agagagatgc ttagcaggtg gtatagttga ctgggcagac agaggataag ataggaggga  18660
gagttaactg tatatcttat atattttggt tttaaaacca tgagaatgaa tgtgttagtc  18720
aaaaaattga aaaggagaaa aaaaaagagg tgaccttgaa ccagcgagtc cactgacctg  18780
tgtgttagcc tccctatccg tatggtgagg cagttggacc agattgagac tccttagtct  18840
gaagtggaat gttgtgaata ttgtatttct caggctttca tggacttttc caggagatcc  18900
tgaccttgtg ctagggtaat ctgcagtccc ttccgttggt agcctggcct ggccctctca  18960
ggatgtttga gaaaggttgg gggcacagag agcaaggagc cttccccaga ggagtcaggc  19020
```

-continued

```
cttgttcctg tccccattcc tcagagttta tcctctgagc acacacctct ggtgtgactc  19080
agttggttct tcctccaaag tgaaggatta cagtgaagag agactgttct ggagcattct  19140
ggcaaagtgc tacagtttaa taggaaggaa aaaaatggca gaacattttc cgggttattt  19200
ttaatgcttt tcagttctgc aaacatttat tgaaagctaa gtgcaaggca gtgtggggga  19260
atcagttgca taatacctca cctctgcttt ctggggtgca aagtcttggg taagaaacat  19320
gcttataaaa tttatcatag taacctctag gacagcctgg cttacccatg atctcattgg  19380
gtcccatgga gacaggtggg attggtaggg actcgtccca ttttacaggt gaagaaactg  19440
aatctcagtg aagtcttgtc caaagccaca cagtttgtaa gcagtaaagc ctgaaaccaa  19500
accagatctt ccgactactt ctcatgtgtc caaacccccca taatcaaaac attctcccat  19560
aggagatgtc cggggtgtag attaggccca tttctacctg gaaacatggg gcaagcacaa  19620
tcctgattaa agcttcttct ccttcacttt tttcctttgc tttttttttt tttttcttc  19680
ttcttcttcc tttaaggcag agcaaggtaa ctcttaggct tatggccaga tctcaggtct  19740
taactacttt cctgtggtct aagcaattct tcttgcattg cctgtgaaac ccactatcct  19800
accaccagtt gcatgtggaa tgtcccctgt gggtaaaggt gtgtaaccta cagcagcctt  19860
ctctccaccc caatctcatg ctgccacctc ctttcttccc ttccacaaat tctctcgtac  19920
ccacctggct tcctagctgt tccccaataa ggccaagcat gccacccact caggatcttt  19980
gccctggctt ttccttcttt ctgtctggaa ggccctccta gttgttgact tggccttacg  20040
tctctgctga aagctcactt tggataggcc ttcctggtta ccctctctaa agtagtgtcc  20100
cttgtcacta ttgcttttct gtccttttct tttctttctt tttttttttt ttgagacgga  20160
gtctcgctgt gtcgcccagg ctggagcgca gtggcgggat ctcggctcac tgcaagctcc  20220
gcctccctgg ttcacgccat tctcctgcct cagcctccgg agtagctggg actacaggtg  20280
cccgccacca cacctggcta attttttgta tttttagtag agtcggggtt tcaccgtgtt  20340
agccagaatg gtcttgatct cctgacctca tgatccgcca gcctcggcct cccaaagtgc  20400
tgggattaca ggcgtgagcc accgcgcccg gtgccttttct gtcctttttt ttttttcttt  20460
gcagcattca tacacattat atacatgtgt atacatttat tggtttattc tttggctccc  20520
ctgctagaat gtagatctgt gagacaggca cctagttttg tttaccacgg tatctttaac  20580
acctagcata gtacctggca tggcatgtag taaatactct gtacggactg ttgaatgatt  20640
gtatcgggcc tgcatcctaa agcaagtaat gcttaagaag aaagaatcaa atcatagcat  20700
tttaagaggg gaaaagactc agagctctct ttgcagggct ttatcataca atattattaa  20760
ttcatctaat aagcatccag cactctttat gtatgaagct ctttgcccac ggtcacttaa  20820
cagccttgtg attcatacag ggacaggaag ctcccaagtt ttcagagcag cccattattt  20880
tgtgagacag ccataatgat ctagagacct tcttacaaag tacactgggg agaaagctgt  20940
ctctttatga ttcctgcact ctgatcttag ttcttgaacc actggaaaac acaataaacg  21000
tacatgacat tccttcaaat aagtggagag agatagtgat catggtctcc cctaccctca  21060
agcctaaaca tcactagttc cttcaattgt tcttctagta tcccagtttt cagatgcctt  21120
cctaccctgg ttgccttcct caaatttgtt ctttaaattt tggaatttca ggtctagtcc  21180
tgtcagtgca gagtgttttg ggaccctgac caaggagccc tggtccatcc cacgtgttcc  21240
tatcagcaca gccttcgatg gctcatctgt gttggctgcc atggtagaag cctccttcat  21300
gagcctctga tgaagactaa aatcattaag ttccttttta cattgtctcg agtcatgtgg  21360
```

```
accctccctg actctcttca tagttttttg gtttggggtt tgtttttgtt ttttagcatt  21420
ttgagattaa agcagccata gacttgtgaa caacaatgaa ctcaacctgc actcttttta  21480
aaaaacaaca agtgtaggta aggttctacc accaaaccca gatgaagagg atggaactct  21540
ggaagttcag caatacctgc caagcctcca actcctttct tccctcatcg tgtctttctc  21600
tgtctgtgtc tgtctctccc tctccccttc cttccagcag cccctcagtt ccccatagtt  21660
tccttgcttt ccctcattcc atttctttta ttaatcctcc ttccaattag aaatatggag  21720
ttaacatata ctgctagcat ttcttgcact tccttcacta ataatttttg ccatacatgt  21780
gtaattcaca gatttaagga agctgcacat ttcacacttg tctaagggag aaataactaa  21840
tgttaaattg cttcttatgt gtagcccctg gctaatttgt tttgtggcct tggatagaaa  21900
aaactttcag ccccagcctt aggttcttct gcatgattgg ttcccatttc tgcccaaatc  21960
agcgatttcc cattggtggt tggacaacag ggcttcagtg ccgaggcggc gtttgctctg  22020
cttctgtcat tgctgatgct gctgtcattt tgcatagagg tggcagggaa ggaggccaag  22080
gtcgaggttt cttctgtgag gccatttagc tttccctgcc tcttctccac ttgcagctct  22140
gcatggatgt gtggaaggtg gtggtgggga gagcaggggc tgagctcagg tctgggctct  22200
tcctaacagc taattttatt ttccaccttt ctttcctctt gcttcaagga ggatggagag  22260
tcctgtgact ttgagggtgt gggccctaag tttggagtct tgagagaatg gcctaaggtt  22320
cgattctaca gtggggtaac tgtgtagcct tgggtgagtc acagagttag tttccaccca  22380
gcttcatcaa ttgctaggga agttggatta gatacagtag ttccccaaaa gtggcattga  22440
tggggtcctt tagttctttg aagcattttt taaaagctat ctgaaaatgg ggcagacgct  22500
tacaccacgg ctgtgggatg cgtcctggcc tctgagtctg attggcatgt tttcttagat  22560
gggttatgct gggggctgga ataggcagaa actttgaatt gccagctcct gggtctctga  22620
atagtaacac tggagaaatg aattaacttc tattttgctg acagttcctc cactcggggt  22680
ccatcccgga ctccaaggca gaaaccctgg gctgctccct gaagactcca gtgggatttc  22740
ctaagcagac agctcccgca gtccacaagc ggtcccagcc aagctgggct tcaatctccc  22800
aatctgattt cagcagccag aattaaccgt atctgtcagc tgggacagtt gatttttcta  22860
agagtggttt tagtggggag ctttgcctca gaaagtgaat aaagggttag ccttctgtaa  22920
tctagattat tctccagagc cattccccac ccacacccca cccctcccct agcctgtttg  22980
gccattcagc aagcatttac tgaaagccag cccctctggg gagggcacta gggtgacact  23040
gagacctcag accttagcaa ggctgtgttg ggggagagat aggaggaaga atgactggcc  23100
ttcagcagca ttcagggccc tggtggacag gggcaggttg cctgggaggg acagaagggg  23160
taaaatttcc attgtctatg aggggagaag cactttgtaa accgtaacat gcaatgccaa  23220
gtgatgtcat tatttttgct gcacatcagg gaggctagca gagggctgag atgggaggaa  23280
gcacaggggt tttgccaggg agcactgatg ggtgggggtc tgggaatcgt actctggatt  23340
tgcacttgat ccctgtggcc attaaaagct tttggacagg ggagtaatga gacatgatgt  23400
gatgtgatca aagcagcgtt ttaggaagat tgagcaggat ttaccctctt tgctctctag  23460
gccttggtct tcattctctg tggcttttct gttgcatggg tgcagtgctg tggttctgta  23520
ataagatcac caagaacggc tgtggtttgt gttttgaatc actgaattgt cagctcatgg  23580
atctgagtag tgatgggtga tcctggtctc tcctctcctc ccaccccagg catcttggag  23640
gccactcaat gacctgtgag aggatagaca tcagatggga caatgctgga ctcccacatt  23700
cagaacccag cacccggggc ctctgggggg tgtttttata tcctgatgtg tggtttttaa  23760
```

-continued

```
aaacttgttg taattaattt tacaaattga tatagttgta cttattttgg gggtgctgat  23820
atgttttaag agattagatg attgagtttc ccatttcact tattacccag ggtaactgcc  23880
ccatgtccca gatttccttc ctggcatccc tcagtgatga atcctgggcc ccttgaccca  23940
tgaaattggc cacgttcttt ccggaacagt gactgagttt gaatgtgggg tgggcactca  24000
ggctcaaagt gtatgtaccg agagaatttt gaaactagag ggaccttatt tctgcactca  24060
ggctctattg tccagtgtat ggactagagg actaggagaa gcccagagag tggtagtgac  24120
ttcccgaagg tcacacagca agttagcggc aaggcggacc aaagcccagg tcatcagagt  24180
gcctgacaag cattctgtgc actacacctt ggtgcatctt ggccccttttt ccttctcttc  24240
cctggttact gttcacacac cacctgctgg gactctgctt ccagtgccta cctcttcagt  24300
cctccagcac ctacctcttc agtcttccag catccactga aggtaggagg ggaacaacca  24360
tgtagaaaga gtcgagtctg cggctgggtg tggtggctca tgcctgtaat cccaacactt  24420
tgggaggtgg agacaggtgg atcacatgag gtcaggagtt caagaccagc ctggccaaca  24480
tggtgaaacc ccgtctctac tgaacataca aaattagcca ggtgtgatgg tgggcgcctg  24540
taatcccagc actttgggag gcggaggcag gtggatcaca tgaggtcagg agttgaagac  24600
cagcctgacc aacatggtga aaccctgtct ctcctgaaaa tacaaaatca gccagacgtg  24660
gtggtgggcg cctgtaattc cagctacttg agaagctgag gcaagagaat cgcttgaatc  24720
tgggtggcag aggttgcagt gagccgagat cacgccactg cacgccagct taggtgacaa  24780
gaacgaaact gtctcaaaat aaaaagagtt gagtctgtaa gattttcact gggtcgtgta  24840
ccctgccagt tctaaaacct tcatctcccc ttttccacac tgcagctccc atcccccagc  24900
aaagctagac ccaaaacccc tccttccctt cttcagaccc caaaacagtt cctgctcctc  24960
tgtgaacact tttaagagct atacacgctc ttaaaccaga caggcctggg ctagaggctg  25020
ggcagtcagg gaaggcttcc tgcgggaggt agaactgaca ggtccttgat gtggagtcta  25080
taccagctgg aaggtaggaa ggaggtttaa gggggaggaa gcaaaggaac aatatcaggg  25140
aggggcccag ctaggattca ccagctaaac aggcccattt ggcaagccca aaactcaggt  25200
cctgcagcca ccccagcctg cggagtactg ccctgagtct gtgtttctgg ctggaggaac  25260
atctgcggtg gaaccagctc ctctgctttg gtgaagcaga aacccaagtc cctctcacac  25320
ccgcgggagg agacagagga agccggttcc aggcggtgca ggagcaagtc acagggttta  25380
tgttaatgcg ggccctcccc gcgccggcgg cttagcctat gagccggggc cctggcagac  25440
agcttaatta ccgctgcagc gcgcctcagc ttgtgttcct tggctcccta aaataataag  25500
gatggcgtca ccgacttccc cgggccatgt gctccccgcc tgccttcaga gctctattgt  25560
aggaaacaaa caacaaaaaa aatcagagac gtggatgctt ttttcttggg gagatttttt  25620
gtttgtttta aagtaatagg ggactctgcc cctagttaag gttttaaaag atcttctaga  25680
ggtgtggaga tctgggtcta ctactgttga ggctgcagaa tagcctcctg ttagcagaaa  25740
cttgaaagct acacgagtga tctgttaatt ccatggtctt ccactgggga tgtgagttct  25800
gatgcctggt ggtggtgtgt gctgcaggga aacgaatcgc ccagctcaca gtgactctgg  25860
ccccaacttt ggaccttgct tcttcctctg aaaaaagaga actgacctac accagagttt  25920
tgcagactgt aggtcacgtt acacatattt tgttctaagt aacataagaa agtaattgca  25980
agtgttaagt tttgttttca gttgtgtatg cctatacaca cacaaaaacg tgtgtactga  26040
gccacggtgt aaaatgtaga aagccactgg cctaggagat ccctaaggcc cttctagctt  26100
```

```
tcaaaatgtc taacttttct gtcagagctt tcacttttcc ccaacatgga acctgactga  26160
tttctgcagg ttttgccaca ctggctgttc agcaaaacca tcgattttat ggttaaaaca  26220
acaaaatcac aagcatctat caccccagtc taaaaccttg gtgtctcaga cagtttggcc  26280
ttctagctga aatgggatct gcaacagggg atggcccatt taaaagctga cctatttaaa  26340
acccacgagc accaaaaaac acagggtcaa tttgatatga gtcttctctt gtgtgcaaag  26400
actggaacct gaaaaccaaa ttagtcaggg actgacaagg ttgaaaccaa agctacaaat  26460
atgtattgaa ttcttgctcc gtgaaggaaa agaaaatcaa gggtggtcag ggttagtgtg  26520
aaaaacaaaa caaggtgtgg atgtaaaaat ccaaaggggt cggttttaag cacaccattc  26580
ctggttcccc aacaggttaa gaggcctcgt atttactata aggaagccgt acagacagct  26640
tagttgactc aaatctgcta acctgccctt cgtttccatt cttgtgcctt gactgtacgc  26700
aacagtaaag atagccatgg aaaaagggga aggcaagtgg ctttttccaa gctggggatg  26760
ctccaagtac attcttattt aatccaaccc taggtgatgg acattatagt cactaaagga  26820
aacggaagct cagaaaggta agctgggcta aaaagaagaa aaattgaact tgagccagtt  26880
ctctcggact cgagagcctg ccttctgtcc acctttcctt gttgcctcag gaagtactag  26940
aaaaagaagg agcagttctt actctaagct tccttctctc tggtcctgtc cttcaaaggg  27000
ctctgtttca ggcccaaact gtccacttta atcagggcca gcttcacagg catgtgaccc  27060
gtgcagcacg cacttggttt aatgcgctgc tgtcactgtc ttggaattct taatttttaa  27120
gcaaggggct ccgtgttttt cattttatgc tgggccctct aagccagtcc tggcttttga  27180
tatagtgtat ctcctccgtt ggtccttctg ggtccccctc atctgccttt agcatgcctg  27240
ttctatctgg tagaggcatt tgaagaatgc accctggccc ggccccagtc ctgctacctg  27300
gcacactgga ctggagttgt ttactggtgg ctgtctcctc ccagccggcc accacacctc  27360
ttgctggcaa ggaccccgac cttggcttac tgtttcttcc gtgtctcctc agccaacagt  27420
gtcgcaggtg tgccccatgt ggagagggct ggagacctgc atgcagagca ctgggtcatt  27480
caggtcaggg ggagtgtgca cagctgacct gcctctcagg ggcttatgct tgtcttgggc  27540
acaagaaaga ctccaaaaaa ccactggtgt ttataaaaga tagggttcat tcaacattta  27600
ttcgtcatac tgttgaatac gtttcatgac agtttgactc acctctatat tcccagcacc  27660
taatgttata cctggcgcaa taaacaggac atttgttaag cagttgctct ggtctccgct  27720
ccctggtagg ctgattacgg aggacagtcc ctgacctcta ggaggatcgg atgcttaata  27780
cacgagtaaa tgattcatgc agcagctgcc cttggtgccc caggatgcac agagctgggt  27840
tggagaaggc ttcctgggaa ggggaactgg atttgtaggg taagagtgag agattggggg  27900
tgctgaggtt ggataaagag gagggagctc caagaatgga gaaccttgga ggtcatgtgt  27960
aggaacttga atttttccca aggcagtgag aagccaggaa tgttttccag gctggagttt  28020
actctttata ggttaaacag atctcatcat cccctttcta cagaggcaga agcctgaggc  28080
ctgggggaga gagctgagat catggagcca gttgggtcga gccctctagg tcgaggcctg  28140
ttcccagtaa tccaggctgc ctcttgacca cttccatcct cacagtcata gagacctggt  28200
gtggaggcaa aagcaggctt gaagtgactc gaggtgacag tgaccagtgc tgcaacgttg  28260
ggaacagagg ggaaaggcca aatttgagag atctgtaaag acaagatttc agttttaaac  28320
aacaaattgt tccttagagt aataacgtat ttgtgtttat catggaattt tcaggtccca  28380
ttggtgaaaa atgactgaca ggtctttgct ttggggacaa gtttttcagg aagtacagga  28440
cccccagcaa tctgacatct tgggaacctt cattgcctcc tcactgacct ctcttatgaa  28500
```

```
tatgagggct ccttttaggt gttcacttga ggaatgaagc attgggtcct gtgtaggttt  28560
ctctttgggg tgttggaaaa gcttctgata caagcagagt aatttcagtt ccactaggta  28620
gggtaaccac atttggatat ttttaaatgg tcagtggaat tgggaaaaag tctacaaaag  28680
tacaaatttt cagtttaatt ttaactttgc gcttcactca cacccaggac ttggcagggg  28740
aagtgggcct tggttttttt tttttctttt taaagcagaa cacaccctgg gtggaaaagg  28800
gatgttctct ttgcatggaa gggttagaac caagtacaga ggaaatgggt tggtattgta  28860
gcaagagttc aggggtgggt ctaggctttg aaactagagc actaggaaag tgtggccctc  28920
atggaggcag gcagggaagg gaatgggatg tctttcacag gcagctgttg ggctgacatt  28980
tttgttttgt cctgtttggt gcatttcaga tacttcacag ctcacctgct gctctcactg  29040
ggacccctct tcatctcatg acaaagcagt gggtctttcc cccatgtggt ttgggctttt  29100
tggtggtatc agcaacctca ggtctaagcc ctgtcccctc cttcccctct gtgatctcac  29160
cctgcatggt gctgaaacca accagggagg aaatgcagaa acagtgggga ttctgaagac  29220
accaccttta aaacgatggg gatttcccaa gggagtggaa gcaacctctt gctatttggg  29280
gaagagcagg gtcccaggcc cctctctgta tccttgcccc ctcctgcagc gtcatctgag  29340
ccagggcagg gttaggctct gtgctttggt tgctaaggat gtgtaaccag agcagagacc  29400
tctaggggtg gtgcccacct ggctggtgga acagttagaa gaggagctga aaagaaacag  29460
ttacagctgt aggggcggga aggtgtgatc cctttcctta cccgtcgtaa gagtcatggc  29520
caacacttat aacaaaagaa aggctaacaa aagaagagcg taacaaattt atttaatcaa  29580
agttgtaagt gacatgagaa ccttcagaga agaagaacca aagacccagg gaaactgcct  29640
atttttatac ttaggtttga tgaagaatag acagccatga agaaatggga ctggacaaag  29700
gggtgtaggc tgagagggaa cccagcaagg cctgtctgtt cagattcttt gtggcctctc  29760
tgtgtagcat tccttcctcc tagatatggg gcaggacttc cctggcatga gggtcttcaa  29820
gggagaaggg acaggagaga gtaacctttc tcggctttgc tttgggagag aggaattcta  29880
gtttctgtga cccgccttgg ggaagagaag ttctggattc tgtgacttct ggggagagag  29940
ggtgagagac aggagggcaa gagaaattca cagagcttgc ttctgaggcc ttccaatctc  30000
ctttagttca aagtacccag cacgccaaag ccccttacat ttgggtattg tgttctgagc  30060
cccagcacag ccaagaactt gtagaattga cttgggggtc tggggagagt cccaagaagc  30120
caacaggggc ccctcctcat cttgtggcta acactagcca cctgagtgca gtagacaccc  30180
accctcctgt gaccttcttt tgggatttta ggataagcag ttcggacgtg cctttaaaac  30240
ggagagaaca caccccaagg agtggttatg gggattaaac gagactgtgt atgaagcacc  30300
tagagtgtgc ctagcgagtg cttgagaaag atatgacgat tatttttaat caaagcatta  30360
atagtgattg cttgagtatt gtcctccaga ggagcagcca ccagttttgg tgttgtggta  30420
ggagccaggg actggcctcg tcagggctcc gaaacctatg tctatctgta gcattcctag  30480
gcagcctacc ccagcagcag ccccttgggc tgtgggcagg ggtggcaggc agcactgttc  30540
ctctccagga aggagaccga cttcctggac gaattccctg ggctccccag cactgctctc  30600
tgaggccctc ctctcctcgg ccaacggcag taaggagaag ccattgaccc gtctagaaaa  30660
accgcatgtc tgcagtcttt gagggtagac tggaatctct tctcatattt gccttgcttt  30720
ggtggagctt caagaattcc caggccttcc aaggaaacca attactaaag aagactgtgg  30780
gccacgtgac tccagtgttt actgcaaacg aaggagatgg ctcccctccc ccaacacagt  30840
```

-continued

```
tactctccct ccatctgcac tggcccccta aggcctggct tcctggctct gcgatgcttt  30900
cctgccctag ggcagaaggc ctcacaggat ttattcccag gcactcttgc catgaccttg  30960
agaaggtggc ttgacctgga catctggatc tcagggactg agggggtggg aaaggactga  31020
gcctccccct cccagaccca acaggaaggt gggctttggt gaccatttcc taggctgaga  31080
gctccttagc tccaggagag ggctgcgctc cctggttctc ctgctctgtg ggctgtgcta  31140
gatgaaaccc acaaattgct gctgtcccgg gcggagtggc atgcctccac ccaccagtga  31200
agaatgaagg cagggcagtt gcagggccct gcaggactct gagatccaga tgtgtacccc  31260
agtgctcccc tgctctgccc actggcaaga gggggctgag gaggggcata gcaggcctca  31320
tgtggactct gtttccacct cctttccccc atatctctac ttggcccaga gatgcctgag  31380
taagaggggc acctagtcat tctgggccca gaaagaagaa gctaggcatg ttggcctgct  31440
caaaggagca ggagcagccc tggacaggga caggttagaa agcctggctg cttatccaag  31500
agaagaaaag gccctgaggg gcaggagcaa ccctttgaac aatgctggac tgctgttgag  31560
aaggaaggct tgtgccatgt gacccattgg tgagaaatca gggcctgtgc atggaagttc  31620
cagggaggga ggcaacaaat ccagttgaca ttggtaagtg tttcctggca cctgcaggga  31680
gcttgggctg ctgtgtcctg ggctgaaggg actctttgag ataccaggtg tgggcaggga  31740
tcacatttaa ggtgtcttcc agtccagaga ggccgggttt cccagaagct ggctgctctg  31800
gggcaggaag gagaactctg ggccagctgc ctggagggcc acacaccggg tctcctttgc  31860
ttactcccag ggtcatttca tgcctgcgac ctggttactt ttcctcggcc tgtctttcta  31920
ccttcttcat tagaacctgc agtttcacct tcagctaagt ctacctctta acaaccctgt  31980
gagagggtgg ctttttattc gttctttcta cctcattaga aataaaggat ttaggaccca  32040
aattgtgggt aagggagctg agtggggaaa aagacagggc cacagaggtg cctccaagca  32100
cagactttga gacagatctc agcatttcat tatgggccca tcctaagttt gtgggtttcc  32160
attctccttc cacgtctatg ctggaccgtg aagagcaaag tctagagctg tgctatccaa  32220
tatagtagtt acctgtgtct gtttacactt aaattaattg aaattaaata gaattaaaag  32280
ctctattcct tagtctcact ggccgcactc cgtggccaca tgtgactagt ggcccctgtc  32340
ttgaacagta cagaccgttt ccgtccttga aggaagttct gttggacagt gctgggctag  32400
aggtgggaga gctggaggag cccctggtct gctgcgcctg cctcaggaca ggccacatgg  32460
gtactgccat gtgaatgcca gctacagcgg caggctctgc tgtgatggca ggagtgggtg  32520
aaagcaactg ggcatgtggg ggtcttgtgg gggcattggg gtggcggggc aaggcccaga  32580
agtccctaac aatgctgtgg ctggtgcatg tgggttttgg gagaatgcga gagcagggtt  32640
ggaatgagac caccaacctt gcagaggcag cagggcttac tgggtttgtc ttctgcggta  32700
cagccaaggc ccctgtctgg agtggccccc tggttctgca gctcggctca ccacaggcct  32760
cctctcaccc agatgttgaa aaggcagaaa agtcagggtg ggcaaatcca tcctgtggtc  32820
gttggcagca cagtgatccg gaaagctaga agaagtgacg gagtgactga ctgcttcctg  32880
cgtctgtctc cctgttctct gaggagtcct ctaacaccct ccccctgctt cagccccatt  32940
cctcagcccc gctcacacgg tcgggccttc tttcaggtga aagaacttgt cctggacaac  33000
agtcggtcga atgaaggcaa actcgaaggc ctcacagatg aatttgaaga actggaattc  33060
ttaagtacaa tcaacgtagg cctcacctca atcgcaaact taccaaagtt aaacaaactt  33120
aagaaggtaa atagagtgga gtctgtgtgt gctgggaggc gggggtgggg agtgggaagg  33180
gttattacct atgtttagaa agagtaattg aagggaaagc cgggtgcttg caccaacatg  33240
```

ccagacaatt gcctgagact gctttccctt cttgcccgtc tggggaaagc cgggcagctc 33300
tgagccggta gccttcattt taaaagctgt ttctgctttt tctttccctg ccttatttag 33360
cttgaactaa gcgataacag agtctcaggg ggcctggaag tattggcaga aaagtgtccg 33420
aacctcacgc atctaaattt aagtggcaac aaaattaaag acctcagcac aatagagcca 33480
ctggtaagtc attcggaccc tcccctccct gcaggggtag gaggtgggag gaattggcat 33540
cagcaaatac tacttttgca tttgtccttt tcccacttaa tttttttgac tctcatgatg 33600
tgctatgaga tagaattgag ctattgtttc tgctgagtcc atagagaaac tgaggcccag 33660
agaagttaaa taccttgacc aaggtcacag acagaatggg cagctattgt acgggtagcg 33720
tagaacccta gtttcaattt ctggtctcct gcttttccac tcagtttctg ctcagctttg 33780
gaaacctgag ctgtaatgtc ttcaggttca gggcatggct tgttgcccct ttttgggaag 33840
ggaggagcaa tccaagaatt aaactggccc tggaggtgga ctccagtttt ctccttgggt 33900
cgctggcccc tgaactgtga gaaatgagtc agtcctgaca tagaaccctg gaatgactga 33960
gagccgtgtg gtgtgagagc ctcgtgcagg caggccttcc tcaacgtggt gtggagaaga 34020
gtgacccctg gtcaccagtc cttgttgcga tagtgaacag gctctcaggg gcctgggtag 34080
catttctggc tcctctgctc atccttgtag agatagacat cccctaagct tcactgattt 34140
accagccaga aaggggcagg tcatgttcag aacaacactt tctataatta ccaggatctg 34200
attcgctgta ttcctttgat tttaaggaaa tcagctgtaa gatgtgtcac tgaaaacaac 34260
tcttttggaa taggaaatac taccacatga agtaaataca cctgttgtga atatacatat 34320
aagagtcacc tcataaggcc gggcgtggta tctcacacct ttaatcccag cactttgaga 34380
gggcaaggca ggtggatcac ctgaggtcaa gagtttgaga ccagcctggc caacatggtg 34440
acaccccatc tgtactaaaa atacaaaaat tagcccggcg tggtggcaca cgcctgtagt 34500
cccagccact cgggaggccg aggcaggaga atctcttgaa cctggaaggc agaggttgca 34560
atgagctgag atcgcgtcac tgcactccag cctgggtgac agagtgagac tctgtctcca 34620
aaaaaaaaaa aaaaaaaaaa aaagcagcag cagcagcacc tcaggcatct tagaatcagg 34680
gaaaggccag gaggacaatt ggccacgttt gccaaatttc ccttctgggt ttatagggga 34740
ggttgggtat ccctcagatt gggctggagt tttcagggtt tctgtcccaa aaggcactcc 34800
ttgctctcca tggatgctca cgggacttgc tggtggccag tgtggcagaa gaggacactg 34860
gcatttcttt tccaagctct ttacctgtcc atcgatggca ttggggccaa ctagtagaat 34920
gtgcttccca cagaacttct tttcaggcct ttcactggtc tcctaggaaa aagccaaact 34980
attttgatct gtctggaagt cttgatttta taatgtcatt acaaaaggaa aaagtctttg 35040
aagttctgta tatgggtgag gtatggggat tgagtatata aaatccttgt aaaacattgt 35100
gattcagtca ccattagggg tcaggcactc aggcacgttc atgttcacac tctccactgc 35160
cccctgccca gatcacacgt gtctcagtgc tttctccgcc cctgcttgtc agtgtgtgtt 35220
gccttaccgt cctggggcgg gaagctgctt ttggtagcag gtgctgggct tgcccacaca 35280
gaccactgtc aagacttcct ccctgccctt ggcttctgct gagaatgacc caggtctcaa 35340
ctgcaaggtc atagagagag caacctagct cccgacattg actccaagga gcaatggttt 35400
cactcccttg ttagacctgg ccacctttgg aatggggact cagcctggga tgggattttt 35460
ttgtacctgg tgcctcaaag gtgggtgagg tgggaagtca aaatgtagct cagttacttg 35520
caagcagtat gacccttcac ttcctgggcc tcagtttcct ctaccatcaa acagggataa 35580

-continued

```
cattggctag aacccgtctg gtgtaaagct ttgacagagc acatcgtgtc aaataccatg  35640
gacagaattg ggtcctcca ttgctttttc tcttgtcctt ttttgacagg caatattcaa  35700
agagtaagag cacaggtctg aagttgggct gcctgatgaa ttaccaaatc ctgtgccctc  35760
catttccaca tatgtgaaat taactaataa ttatttctac cttacagggg ttgtgagata  35820
aagtgactca gtacatgaag tgccatgtta accgccctta tcatcatcat tatcagatgc  35880
agaaggagtt agtttgttag ttcaagttga cttttggttt ccctctggct ccttagtctc  35940
agggagaggc agtaaacctc ttggctcatg caccaagaaa gccccaggct aatttcaagt  36000
caatcactgt taagacagaa gctgtaattg cagaataaaa gtgttaacat tggataaggc  36060
ttcaaagatc ctccagtcca accccccatt ttccagatgg agacgccgag gcccacaaac  36120
tgcaggtgat atgtctgggc aaacactgtg gctaagcaga gccaaatcca agcttcctta  36180
tcacctggaa gtcatggtct gcgcatgcta tctcatggca tccttgcctg tttgctaggg  36240
ctgttcctcc accttcctcc cacaaatcac ttactgttgg cttcattttt ccgcttgcag  36300
aaaaagttag aaaacctcaa gagcttagac cttttcaatt gcgaggtaac caacctgaac  36360
gactaccgag aaaatgtgtt caagctcctc ccgcaactca catatctcga cggctatgac  36420
cgggacgaca aggaggcccc tgactcggat gctgagggct acgtggaggg cctggatgat  36480
gaggaggagg atgaggatgg tgggtgacag ggtgcggccc agggctgcag ggcccagct  36540
gaggccttgg ggctcgtcct tggctttgca gaggtgggtg ggctgggtgt tgggaggccc  36600
ccacccagct actgaaggct ggctgtctgt ctggtagcta ccaccttcca aagctatgga  36660
ggggagtagg gctgtctgct ttgttttcca tagtccctaa tctgtctcat tggttgactt  36720
ccctaaaaga acaaagcatg agtcccatgc tcatggaaat atcctgagat tctccaactg  36780
cataataact cctttaaaac catccaactg aatccccact tcaatttttg tccctttcc  36840
aaagccccca gggagtggga ttctacagtc tttctgtagt gtgacccgca cttagacact  36900
ctcccaggga gggagggagg ggatagagag agaagagtgt gtggcctgag gacccctctt  36960
tcccatctag gtattcagta gtggagagga ggtccagagc tagaggggtt gtggggcccc  37020
ctggtggttg cagcctacag ccccacacct aggggcacag gctcaggtgc tcaggagccc  37080
caggtgctca gaagtggagg actgcaggcc acttgttggg ttccctggca gtgtggtgtg  37140
tagtcgaggc ctacaggaag gaaggaggga aaagaaggga gtcctgttcc ctccccttct  37200
cccttgccac cagcacagtg cagctttccc atgcatcttc gtggccagat aaagttgaga  37260
atggagacac ttgcctgatt aattaattca gatacaggat tttggttttc tttgttcaat  37320
tgggagtgtt ttgcaagata ctcagagacc atgtttgcct tggtggggat cttgtgatat  37380
ggcagaaagg agccaaaact ggcagtcccg ggaccaggtc ccctaggccc agctcaacta  37440
gtgactcgat gcgtgacctt gaacaagtca gttctctctg tgcctcagat ctctcacctt  37500
taacctgagg agtttgattt gatcttgccg ctttcccggg ccctggaacc tgttgctgtg  37560
ctctgacaat ttcctggtgg tctcggtgtg agaggcctcc agaaggggcc tttcacatgc  37620
ataacacttg tgaggggggc ttatctttgg cacaacttca ggatgtgttt aattatgtca  37680
gcactgtttt catgagagtt agtgtgttcc atctttggac ttaggtgggt gtgggagggt  37740
catgagcccc acactgaaga cgctacaagg ggcctgtgct gtgtgggggg cggagccagc  37800
tcaccactag ttctgtttcc gttccccatt tcgattgcac agaggaggag tatgatgaag  37860
atgctcaggt agtggaagac gaggaggacg aggatgagga ggaggaaggt gaagaggagg  37920
acgtgagtgg agaggaggag gtaaggaggc tgggctgggc agggccaccg tctgcccctt  37980
```

tgaggcagtc ccactgactg cctctgtgat cagtcttggc agccccggag ccctggttag 38040
gaaagtcgct ccccgatggg tagtgaagtg agtccatttc agagcctttc actgggctgt 38100
ttctggggag acaagacttg cagtaagctc tggggaggct ggattagaag aggggaagag 38160
gattttagag gcagggactg aacctgctgg ggtaagcctg gccgttgttt ctatgtgaag 38220
aagtacagaa tgcatggccc cattttctgc tttttgcttt catatgctaa ttaagatatt 38280
cattgagcac ttaaactgtg ctagggaaaa ccaaagtctg ccttgaactg ataggtagca 38340
ggataacact gctggatccc aaatcagaga gtgacactat ggaaatagag caccaggagt 38400
tggccatttt cctaaagaga ttggctggtt cccagttttt taacaagatc tgtgaggggg 38460
tgagtcccag ctctaccact cgcaagctgt gtgtccccag acaatttacc tgacctttct 38520
gagcctattt cttcatctgt aaaataggga tcatgatagc tttctcacag ggttgttaag 38580
aggataaagt gaagtgtaag taaaatgctt aaggacagtg tctgacaagg ggtaagtgtc 38640
tgactgctta ttgtaggcgt tcacaccctc ctccaggttc ctggcactgt gttgggtttt 38700
gtgtttgtgt gttctgagtc tctctgtagc agagtcattt tctatgactt gctcagaatt 38760
ctaaatcaac tcttgctaat tgcaaaagtt agaactagag agttttaaag tgacaatagc 38820
atggacaagg cgcctgtgtc ccctcccaac tccccccgca gtttcctgtc tccctcaatg 38880
gaggatgcag acacatccgc ttgccacacg gactcactca gatagtgtct tccagttcca 38940
gccagccggc ccaggcttga gagacacagg ccaatgacaa tagaatcgcg gaggccaggc 39000
gcggtggctc acgcctgtaa tcctagcact ttgggaggcc gaggcgggcg gatcacttga 39060
ggtcaggaga tcgagaccag cctaggcaac atggcgagac tccatctcta ctaaaaatat 39120
aaaaattagc caggcatgtt gatggatgcc tataattcca gctacacagg aggctggggc 39180
acgcgaatcg cttgaacctg ggaggcagag gttgcagtga gccgagatgg caccgctgca 39240
ttccagcctg ggcaatagag cgagactcag ttaaaaaaaa aaaaaaaagc tggccagatg 39300
agcttggttt ctgtttagtt gtgctgctgg ctttgccttc tccctaggtc tagactctta 39360
ggctcatctc taaagaatat tgtattttaa aaataaagtc ttagtaaaac aggttcccct 39420
agaacagggc agtaagttgt attggctaat agctgttaca tcttcctctt cctgtcacag 39480
gagtgctgca tgtgaggttt ggggggtgg ggatgggga gggttgtgga ttttgttttt 39540
tgttttttgt tttttaaata atctcactga ccatctgcat atttccagct ttcagtaaag 39600
gagagcttat acatgcaaaa aaaaaccaga accttagcaa acagactgat gagggaactc 39660
tttggtgaca ttttaaaaga atgtttccct tgacaaaaaa gaagtctgtc accaagttct 39720
tttaaacttc aggaaccagg tttaacaagc agagattcaa cttgcatata ctttcaggag 39780
cagaggaaag caagggccct gtgttgagaa agaaagtcat acaccttgct gaatctcaag 39840
ccggttggga atgatgtcct cagggggtct tgaatttatc ttccccaacc cttccaggtg 39900
gtccaagttt gcaagctagg gaaggggctg ggtcaggtga cgttgaactt gcccacagaa 39960
tctggatttg cttaaactgg ggtcttctct tgaagccaaa actagattga ggacagatgc 40020
aagaaaggat ggcctacttt gcacgtcagg gagtctgctc gggaacttgt tctcctcaga 40080
gaatgtgcag actggagagc tgcctgcctt acagggactt cagatcagag ttcttaacct 40140
gggtcctgga atccataacc ccctgaaact gcttgcaaat attataaatg atacggacat 40200
tttctggaga aggagttcaa agctttctgc agatttccca atgagtcctt gatctgaaat 40260
aaattaagaa cctctgcttt acattcctcc cgagatgtca agtcttggtg ggggctctga 40320

-continued

```
gaggctgggg gtgaccccgg cctttttgtg ctctgtgtgg cttcctcagc atgtcccaag  40380
gcagggcatt tctaatgttc tggtgtctgt cctttctcct aggaggatga agaaggttat  40440
aacgatggag aggtagatga cgaggaagat gaagaagagc ttggtggtat ggcagccttt  40500
ttactctcag ctggtagcag cctggccctt tcactttggc cttagattgc ttagactcag  40560
aggcccctgg cagtgggcag gacactcctg tcagaggcct cagattcccc ttccagctgt  40620
gcagatgtct tgcctcggtt tccaaggatg gcacagcttg ctagtcatgg gtcccctgac  40680
ttctcactgg gtgggttgag ttaaagaggt gggattaata actaatctaa atgccgcttt  40740
cttacttttc cagaagaaga aaggggtcag aagcgaaaac gagaacctga agatgaggga  40800
gaagatgatg actaagtgga ataacctatt ttgaaaaatt cctattgtga tttgactgtt  40860
tttacccata tcccctctcc cccccccctc caatcctgcc ccctgaaact tatttttttc  40920
tgattgtaac gttgctgtgg gaacgagagg ggaagagtgt actgggggtt gcggggggag  40980
ggatggcggg tgggggtgga ataaaatact atttttactg ccactcttta tttttttccc  41040
ctactttttc tttgtgtccg gtttttgtcc ctgtaaatgc gatagctaag tacacactaa  41100
gtgagcattt gttcctgact ctcaaagagg atggtttgga gttctcttac gtttcctggt  41160
atttcccaag tctcttgggt tggttggaag gctgtggctg gtctcagttt ggttactcaa  41220
tgcccaggag gggctgagca ccagccatat cttttgcttt ggttcacatg atgatacctg  41280
cttttctcag gcctgctaga ggcatccaac gccctggttt gtaaatagca acctaaaggc  41340
gtattttggc actggtctgg ggacattccc catctctcat cccttttccc ccttcacaga  41400
tggtggtggg cttcgctcta caaagaggac tctgatgtta ctcttgagct tatgagccag  41460
agagctgaaa accgcaggct tgttgtgtta agttacaagg aaaatggatt tggtaattaa  41520
aattagaaga aacacacctt caaacttcaa cttctttaaa agaaaaaaaa aactgtccta  41580
tcttgttctg taaaatatta gaacgctttg ttttacaaaa aatgatgaga gaattcttcc  41640
acatgtactt ctgtgcttag aacattttta cggacctaag cgctggagac gttgctgcat  41700
gtcggctggg tttttttttt catacacccg agcacggaaa aactaacgca aaattgtatt  41760
ttcttaccta gtggaaatct gaaatgactg caaattccta gtgaatgtac aggtttgctt  41820
tcgtgtccct cttctggttg ctttagaagt gacgtgtaat ttctgaaccc atgtttcatc  41880
tgtataaaag aacatctgca ccagtttttc tcctgcccct cagaagagcc aaactttgag  41940
ttttatgtct gtttgtcatt gataaatttc aataaatctt tttatacaat ttttttgggg  42000
atggcttctt tgagtccaac aggccattga tcttttcaag atgcattcca gatgaactgc  42060
taggtgaggg ggaagcttca tttttgttac ctgatagaat agcttttctt atgagatata  42120
tataatgtga tactatgttt ggatattttt ggtcttaaag caagactcag tggtgtatct  42180
tcattaaaag cttcctttaa aaaagttaca gagttactaa aaaaacaagt acccaaacaa  42240
tcaagttggg ccaaccttgg aaccttgttt tgaatatctt tcattgtttt gtttgtcgta  42300
ttgtaaaaag aatgtatggt tgaaaactca ggaatgttta taaaacaaat tatttcacaa  42360
a                                                                  42361
```

<210> SEQ ID NO 3
<211> LENGTH: 281
<212> TYPE: PRT
<213> ORGANISM: Artificial Sequence
<220> FEATURE:
<223> OTHER INFORMATION: cANP32A

<400> SEQUENCE: 3

Met Asp Met Lys Lys Arg Ile His Leu Glu Leu Arg Asn Arg Thr Pro
1               5                   10                  15

Ser Asp Val Lys Glu Leu Val Leu Asp Asn Cys Arg Ser Tyr Glu Gly
            20                  25                  30

Lys Ile Glu Gly Leu Thr Asp Glu Phe Glu Glu Leu Glu Phe Leu Ser
        35                  40                  45

Thr Ile Asn Val Gly Leu Ala Ser Val Ala Asn Leu Pro Lys Leu Asn
    50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Gly Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Glu Asp Glu Asp Val
                165                 170                 175

Leu Ser Leu Val Lys Asp Arg Asp Asp Lys Glu Ala Pro Asp Ser Asp
            180                 185                 190

Ala Glu Gly Tyr Val Glu Gly Leu Asp Asp Glu Glu Glu Asp Glu Asp
        195                 200                 205

Glu Glu Glu Tyr Asp Asp Asp Ala Gln Val Val Glu Asp Glu Glu Asp
    210                 215                 220

Glu Glu Glu Glu Glu Glu Gly Glu Glu Glu Asp Val Ser Gly Glu Glu
225                 230                 235                 240

Glu Glu Asp Glu Glu Gly Tyr Asn Asp Gly Asp Val Asp Asp Asp Glu
                245                 250                 255

Asp Glu Glu Glu Pro Asp Glu Glu Arg Gly Gln Lys Arg Lys Arg Glu
            260                 265                 270

Pro Glu Asp Glu Gly Asp Glu Asp Asp
        275                 280

<210> SEQ ID NO 4
<211> LENGTH: 249
<212> TYPE: PRT
<213> ORGANISM: Artificial Sequence
<220> FEATURE:
<223> OTHER INFORMATION: hANP32A

<400> SEQUENCE: 4

Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Asp Asn Arg Val Ser Gly Gly Leu
65                  70                  75                  80

-continued

```
Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Glu Asp Glu Asp Glu
                165                 170                 175

Glu Glu Tyr Asp Glu Asp Ala Gln Val Val Glu Asp Glu Glu Asp Glu
            180                 185                 190

Asp Glu Glu Glu Glu Gly Glu Glu Glu Asp Val Ser Gly Glu Glu Glu
        195                 200                 205

Glu Asp Glu Glu Gly Tyr Asn Asp Gly Glu Val Asp Asp Glu Glu Asp
    210                 215                 220

Glu Glu Glu Leu Gly Glu Glu Glu Arg Gly Gln Lys Arg Lys Arg Glu
225                 230                 235                 240

Pro Glu Asp Glu Gly Glu Asp Asp Asp
                245
```

<210> SEQ ID NO 5
<211> LENGTH: 25
<212> TYPE: DNA
<213> ORGANISM: Artificial Sequence
<220> FEATURE:
<223> OTHER INFORMATION: ANP32A ex1-F

<400> SEQUENCE: 5
caccggcgac gatggacggg acgag 25

<210> SEQ ID NO 6
<211> LENGTH: 25
<212> TYPE: DNA
<213> ORGANISM: Artificial Sequence
<220> FEATURE:
<223> OTHER INFORMATION: ANP32A ex1-R

<400> SEQUENCE: 6
aaacctcgtc ccgtccatcg tcgcc 25

<210> SEQ ID NO 7
<211> LENGTH: 22
<212> TYPE: DNA
<213> ORGANISM: Artificial Sequence
<220> FEATURE:
<223> OTHER INFORMATION: ANP32A ex4/5-F

<400> SEQUENCE: 7
ctgtctgtcc tgtagaggtt ta 22

<210> SEQ ID NO 8
<211> LENGTH: 21
<212> TYPE: DNA
<213> ORGANISM: Artificial Sequence
<220> FEATURE:
<223> OTHER INFORMATION: ANP32A ex4/5-R

<400> SEQUENCE: 8
gtcttcctcc ttccagtctc t 21

<210> SEQ ID NO 9
<211> LENGTH: 20
<212> TYPE: DNA
<213> ORGANISM: Artificial Sequence
<220> FEATURE:
<223> OTHER INFORMATION: ACTB qRT-F

<400> SEQUENCE: 9
aggagatcac agccctggca 20

<210> SEQ ID NO 10
<211> LENGTH: 20
<212> TYPE: DNA
<213> ORGANISM: Artificial Sequence
<220> FEATURE:
<223> OTHER INFORMATION: ACTB qRT-R

<400> SEQUENCE: 10
caatggaggg tccggattca 20

<210> SEQ ID NO 11
<211> LENGTH: 20
<212> TYPE: DNA
<213> ORGANISM: Artificial Sequence
<220> FEATURE:
<223> OTHER INFORMATION: viral M qRT-F

<400> SEQUENCE: 11
aaccgaggtc gaaacgtacg 20

<210> SEQ ID NO 12
<211> LENGTH: 20
<212> TYPE: DNA
<213> ORGANISM: Artificial Sequence
<220> FEATURE:
<223> OTHER INFORMATION: viral M qRT-R

<400> SEQUENCE: 12
cggtgagcgt gaacacaaat 20

<210> SEQ ID NO 13
<211> LENGTH: 20
<212> TYPE: DNA
<213> ORGANISM: Artificial Sequence
<220> FEATURE:
<223> OTHER INFORMATION: A#1 gRNA

<400> SEQUENCE: 13
aaaggatcca cttagagctg 20

<210> SEQ ID NO 14
<211> LENGTH: 20
<212> TYPE: DNA
<213> ORGANISM: Artificial Sequence
<220> FEATURE:
<223> OTHER INFORMATION: A#4 gRNA

<400> SEQUENCE: 14
ccacaactca catacctcga 20

<210> SEQ ID NO 15
<211> LENGTH: 23
<212> TYPE: DNA

-continued

```
<213> ORGANISM: Artificial Sequence
<220> FEATURE:
<223> OTHER INFORMATION: modified A#4 gRNA

<400> SEQUENCE: 15

ccacaactca catacctcga tgg                                           23
```